US009487535B2

(12) United States Patent
Sun et al.

(10) Patent No.: US 9,487,535 B2
(45) Date of Patent: Nov. 8, 2016

(54) ASYMMETRIC SYNTHESES FOR SPIRO-OXINDOLE COMPOUNDS USEFUL AS THERAPEUTIC AGENTS

(71) Applicant: Xenon Pharmaceuticals Inc., Burnaby (CA)

(72) Inventors: Shaoyi Sun, Coquitlam (CA); Jianmin Fu, Coquitlam (CA); Sultan Chowdhury, Surrey (CA); Ivan William Hemeon, Surrey (CA); Michael Edward Grimwood, North Vancouver (CA); Tarek Suhayl Mansour, New City, NY (US)

(73) Assignee: Xenon Pharmaceuticals Inc., Burnaby (CA)

( * ) Notice: Subject to any disclaimer, the term of this patent is extended or adjusted under 35 U.S.C. 154(b) by 551 days.

(21) Appl. No.: 13/794,147

(22) Filed: Mar. 11, 2013

(65) Prior Publication Data

US 2013/0274483 A1 Oct. 17, 2013

Related U.S. Application Data

(60) Provisional application No. 61/623,336, filed on Apr. 12, 2012.

(51) Int. Cl.
C07D 491/20 (2006.01)
C07D 209/34 (2006.01)
C07D 405/10 (2006.01)
C07D 491/107 (2006.01)

(52) U.S. Cl.
CPC ............ *C07D 491/20* (2013.01); *C07D 209/34* (2013.01); *C07D 405/10* (2013.01); *C07D 491/107* (2013.01)

(58) Field of Classification Search
None
See application file for complete search history.

(56) References Cited

U.S. PATENT DOCUMENTS

| 3,723,459 A | 3/1973 | Paragamian |
| 4,886,788 A | 12/1989 | Skuballa et al. |
| 4,935,446 A | 6/1990 | Imaki et al. |
| 6,110,969 A | 8/2000 | Tani et al. |
| 6,225,347 B1 | 5/2001 | Buchmann et al. |
| 6,235,780 B1 | 5/2001 | Ohuchida et al. |
| 6,262,293 B1 | 7/2001 | Tani et al. |
| 6,288,119 B1 | 9/2001 | Ohuchida et al. |
| 6,355,627 B1 | 3/2002 | Ishida et al. |
| 7,700,641 B2 | 4/2010 | Chafeev et al. |
| 7,799,798 B2 | 9/2010 | Chafeev et al. |
| 7,935,721 B2 | 5/2011 | Sun et al. |
| 8,101,647 B2 | 1/2012 | Chafeev et al. |
| 8,106,087 B2 | 1/2012 | Chafeev et al. |
| 8,263,606 B2 | 9/2012 | Chafeev et al. |
| 8,415,370 B2 | 4/2013 | Chafeev et al. |
| 8,445,696 B2 | 5/2013 | Cadieux et al. |
| 8,450,358 B2 | 5/2013 | Chafeev et al. |
| 8,466,188 B2 | 6/2013 | Chafeev et al. |
| 2007/0049609 A1 | 3/2007 | Broka et al. |
| 2011/0086899 A1 | 4/2011 | Winters et al. |
| 2011/0237567 A9 | 9/2011 | Chafeev et al. |
| 2011/0269788 A1 | 11/2011 | Cadieux et al. |
| 2011/0294842 A9 | 12/2011 | Cadieux et al. |
| 2012/0035199 A9 | 2/2012 | Chafeev et al. |
| 2012/0122909 A9 | 5/2012 | Chafeev et al. |
| 2013/0072537 A1 | 3/2013 | Chafeev et al. |
| 2013/0072686 A1 | 3/2013 | Cadieux et al. |
| 2013/0143941 A1 | 6/2013 | Winters et al. |
| 2014/0336390 A1 | 11/2014 | Cadieux et al. |

FOREIGN PATENT DOCUMENTS

| WO | WO 93/23083 A1 | 11/1993 |
| WO | JP 7-508976 A | 10/1995 |
| WO | WO 00/42044 A1 | 7/2000 |
| WO | WO 2005/035498 A1 | 4/2005 |
| WO | WO 2005/105753 A2 | 11/2005 |
| WO | WO 2006/110654 A1 | 10/2006 |
| WO | WO 2006/110917 A2 | 10/2006 |
| WO | WO 2007/025925 A1 | 3/2007 |
| WO | WO 2008/046087 A2 | 4/2008 |
| WO | WO 2008/060789 A2 | 5/2008 |
| WO | WO 2008/110741 A2 | 9/2008 |
| WO | WO 2010/045197 A1 | 4/2010 |
| WO | WO 2010/045251 A2 | 4/2010 |
| WO | WO 2011/002708 A1 | 1/2011 |
| WO | WO 2011/047173 A9 | 4/2011 |
| WO | WO 2011/047174 A1 | 4/2011 |
| WO | WO 2011/106729 A2 | 9/2011 |
| WO | WO 2013/154712 A1 | 10/2013 |

OTHER PUBLICATIONS

U.S. Appl. No. 13/787,558.
U.S. Appl. No. 13/909,964.
Corey and Noe, "Preparation of O-Allyl-N-(9-Anthracenylmethyl)Cinchonidinium Bromide as a Phase Transfer Catalyst for the Enantioselective Alkylation of Glycine Benzophenone Imine tert-Butyl Ester: (4S)-2-(Benzhydrylidenamino)Pentanedioic Acid, 1-tert-Butyl Ester-5-Methyl Ester [[Cinchonanium, 1-(9-anthracenylmethyl)-9-(2-propenyloxy)-, bromide, (8a,9R)-and L-Glutamic acid, N-(diphenylmethylene)-, 1-(1,1-dimethylethyl) 5-methyl ester]]," *Organic Syntheses*80(11): 38-45, 2003; Col. vol. 11: 404-409.
Dehmlow et al., "Monodeazacinchona Alkaloid Derivatives: Synthesis and Preliminary Applications as Phase-Transfer Catalysts," *Eur. J. Org. Chem.*13: 2087-2093, 2002.
Guillaumet et al., "Synthese d'un analogue dioxinique du psoralene," *Tetrahedron Letters* 29(22): 2665-2666, 1988.
Klugbauer et al., "Structure and functional expression of a new member of the tetrodotoxin-sensitive voltage-activated sodium channel family from human neuroendocrine cells," *EMBO J.* 14(6): 1084-1090, 1995.

(Continued)

*Primary Examiner* — Michael Barker

(74) *Attorney, Agent, or Firm* — Seed IP Law Group PLLC

(57) ABSTRACT

This invention is directed to asymmetric syntheses of certain spiro-oxindole derivatives, which are useful for the treatment and/or prevention of sodium channel-mediated diseases or conditions, such as pain.

26 Claims, No Drawings

(56) References Cited

OTHER PUBLICATIONS

Lossin et al., "Molecular Basis of an Inherited Epilepsy," *Neuron* 34: 877-884, Jun. 13, 2002.
Ooi and Maruoka, "Recent Advances in Asymmetric Phase-Transfer Catalysis," *Angew. Chem. Int. Ed.* 46: 4222-4266, 2007.
Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.
Swamy et al., "Mitsunobu and Related Reactions: Advances and Applications," *Chem. Rev.* 109: 2551-2651, 2009.
International Search Report and Written Opinion, mailed Apr. 1, 2011, for PCTAN PCT/US2010/052704, 12 pages.
International Preliminary Report on Patentability, mailed Apr. 17, 2012, for PCTAN PCT/US2010/052704, 6 pages.
Response to Official Action from European Patent Office, dated Dec. 14, 2012, for Patent Application No. 10 771 606.0, 25 pages.
Official Action from New Zealand Intellectual Property Office, dated Dec. 6, 2012, for Patent Application No. 599334, 2 pages.
Cadieux et al., entitled Synthetic Methods for Spiro-Oxindole Compounds, Restriction Requirement mailed May 7, 2012, for U.S. Appl. No. 12/904,880, 7 pages.
Cadieux et al., entitled Synthetic Methods for Spiro-Oxindole Compounds, Response to Restriction Requirement mailed Jun. 7, 2012, for U.S. Appl. No. 12/904,880, 1 page.
Cadieux et al., entitled Synthetic Methods for Spiro-Oxindole Compounds, Office Action mailed Aug. 16, 2012, for U.S. Appl. No. 12/904,880, 40 pages.
Cadieux et al., entitled Synthetic Methods for Spiro-Oxindole Compounds, Amendment mailed Nov. 16, 2012, for U.S. Appl. No. 12/904,880, 15 pages.
Cadieux et al., entitled Synthetic Methods for Spiro-Oxindole Compounds, Notice of Allowance mailed Jan. 24, 2013, for U.S. Appl. No. 12/904,880, 11 pages.
Cadieux et al., entitled Synthetic Methods for Spiro-Oxindole Compounds, Office Action mailed Feb. 1, 2013, for U.S. Appl. No. 13/620,391, 42 pages.
Cadieux et al., entitled Synthetic Methods for Spiro-Oxindole Compounds, Amendment filed May 1, 2013, for U.S. Appl. No. 13/620,391, 7 pages.
International Search Report and Written Opinion, mailed Jun. 28, 2013, for PCTAN PCT/US2013/030219, 17 pages.
Official Action from Intellectual Property Australia, dated Aug. 14, 2015, for Patent Application No. 2010306768, 3 pages.
Translation of Official Action from Ministry of Scientific Research Academy of scientific Research & Technology Patent Office, dated Aug. 15, 2014, for Patent Application No. PCT/2012.671, 6 pages.
Translation of Official Action from Ministry of Scientific Research Academy of scientific Research & Technology Patent Office, dated Apr. 22, 2015, for Patent Application No. PCT/2012.671, 7 pages.
Official Action from European Patent Office re extended European search report, dated Apr. 9, 2014, for Patent Application No. 14000519.0, 9 pages.
Response to Official Action from European Patent Office, dated Apr. 24, 2015, for Patent Application No. 14000519.0, 10 pages.
Translation of Official Action from Japanese Patent Office, dated Oct. 31, 2014, for Patent Application No. 2012-534362, 6 pages.
Official Action from New Zealand Intellectual Property Office, dated Mar. 13, 2014, for Patent Application No. 622072, 2 pages.
Response to Official Action from New Zealand Intellectual Property Office, mailed Jun. 9, 2015, for Patent Application No. 622072, 22 pages.
Official Action from New Zealand Intellectual Property Office, dated Jun. 22, 2015, for Patent Application No. 622072, 2 pages.
Translation of Official Action from Intellectual Property Office of Russia, dated Jul. 14, 2014, for Patent Application No. 2012119550, 2 pages.
Official Action from Intellectual Property Office of Singapore, dated Aug. 14, 2014, for Patent Application No. 2012025391, 14 pages.
Cadieux et al., entitled Synthetic Methods for Spiro-Oxindole Compounds, Preliminary Amendment dated Jul. 22, 2014, for U.S. Appl. No. 14/272,297, 5 pages.
Cadieux et al., entitled Synthetic Methods for Spiro-Oxindole Compounds, Office Action mailed Mar. 11, 2015, for U.S. Appl. No. 14/272,297, 48 pages.
Cadieux et al., entitled Synthetic Methods for Spiro-Oxindole Compounds, Amendment filed Jun. 29, 2015, for U.S. Appl. No. 14/272,297, 11 pages.
Cadieux et al., entitled Synthetic Methods for Spiro-Oxindole Compounds, Office Action mailed Jul. 31, 2013, for U.S. Appl. No. 13/620,391, 6 pages.
Cadieux et al., entitled Synthetic Methods for Spiro-Oxindole Compounds, Amendment filed Oct. 31, 2013, for U.S. Appl. No. 13/620,391, 8 pages.
Cadieux et al., entitled Synthetic Methods for Spiro-Oxindole Compounds, Notice of Allowance mailed Jan. 22, 2014, for U.S. Appl. No. 13/620,391, 12 pages.
Invitation to Pay Additional Fees, mailed May 3, 2013, for PCTAN PCT/US2013/030219, 5 pages.
International Preliminary Report on Patentability, mailed Oct. 14, 2014, for PCTAN PCT/US2013/030219, 10 pages.
Translation of Official Action from Eurasian Patent Office, dated Sep. 29, 2015, for Patent Application No. 201491854/28, 5 pages.
Official Action from European Patent Office, dated Jan. 27, 2015, for Patent Application No. 13710961.7, 2 pages.
Response to Official Action from European Patent Office, mailed Aug. 5, 2015, for Patent Application No. 13710961.7, 8 pages.
Official Action from Intellectual Property Office of New Zealand, mailed Jul. 9, 2015, for Patent Application No. 630189, 2 pages.
Bennett and Xie, "A peripheral mononeuropathy in rat that produces disorders of pain sensation like those seen in man," *Pain* 33: 87-107, 1988.
Goldberg et al., "Loss-of-function mutations in the $Na_v1.7$ gene underlie congenital indifference to pain in multiple human populations," *Clin. Genet.* 71: 311-319, 2007.
Ikoma et al., "The neurobiology of itch," *Nature Reviews Neuroscience* 7: 535-547, Jul. 2006.
MacNicol, "Clathrates and Molecular Inclusion Phenomena," *Chemical Society Reviews* 7(1): 65-87, 1978.
Saenger, "Cyclodextrin Inclusion Compounds in Research and Industry," *Angew. Chem. Int. Ed.* Engl 19: 344-362, 1980.
Saishin Souyaku-Kagaku, 1st volume, Chapter 21, Yakubutsu no Sayou no Rittai-Kagaku II: Enantiomer, Ken-ichiro Otsuka, Technomics Corporation, 1998, 1st edition, pp. 475-501, 28 pages.
Shin-Jikkenn Kagaku Koza I, Kihon-sosa, 1975, pp. 325-327, 4 pages.
Sircar et al., "Synthesis and Sar of N-Benzoyl-l-Biphenylalanine Derivatives: Discovery of TR-14035, A Dual $\alpha_4\beta_7/\alpha_4\beta_1$ Integrin Antagonist," *Bioorganic & Medicinal Chemistry Letters* 10: 2051-2066, 2002.
Weber and Czugler, "Functional Group Assisted Clathrate Formation—Scissor-Like and Roof-Shaped Host Molecules," *Topics in Current Chemistry* 149: 45-135, 1988.
Translation of Official Action from Japanese Patent Office, dated Oct. 15, 2015, for Patent Application No. 2015-039888, 5 pages.
Official Action from New Zealand Intellectual Property Office, dated Oct. 5, 2015, for Patent Application No. 712378, 2 pages.
International Search Report and Written Opinion, mailed Jun. 9, 2011, for PCTAN PCT/US2011/026359, 14 pages.
International Preliminary Report on Patentability, mailed Nov. 1, 2012, for PCTAN PCT/US2011/026359, 10 pages.
Official Action from Intellectual Property Australia, dated Sep. 30, 2015, for Patent Application No. 2011220396, 3 pages.
Translation of Official Action from State Intellectual Property Office of China, dated Sep. 18, 2013, for Patent Application No. 201180010245.7, 7 pages.
Translation of Official Action from State Intellectual Property Office of China, dated Jul. 17, 2014, for Patent Application No. 201180010245.7, 6 pages.
Translation of Official Action from State Intellectual Property Office of China, dated Mar. 18, 2015, for Patent Application No. 201180010245.7, 7 pages.

(56) References Cited

OTHER PUBLICATIONS

Official Action from European Patent Office, dated Jul. 19, 2013, for Patent Application No. 11 707 750.3, 7 pages.
Translation of Official Action from Patent Office of Japan, dated Jan. 27, 2015, for Patent Application No. 2012-555199, 4 pages.
Translation of Official Action from Patent Office of Japan, dated Dec. 22, 2015, for Patent Application No. 2012-555199, 6 pages.
Official Action from Intellectual Property Office of New Zealand, mailed May 7, 2013, for New Zealand Patent Application No. 601667, 2 pages.
Response to Official Action from Intellectual Property Office of New Zealand, mailed Jul. 30, 2014, for Patent Application No. 601667, 55 pages.
Official Action from Intellectual Property Office of New Zealand, mailed Aug. 12, 2014, for New Zealand Patent Application No. 601667, 2 pages.
Translation of Official Action from Patent Office of Russia, dated Feb. 19, 2015, for Patent Application No. 2012140955, 4 pages.
Official Action from Intellectual Property Office of Singapore, mailed Jul. 11, 2014, for Singapore Patent Application No. 2012056909, 13 pages.
Winters et al., entitled Pharmaceutical Compositions of Spiro-Oxindole Compound for Topical Administration and Their Use as Therapeutic Agents, Preliminary Amendment dated Oct. 30, 2012, for U.S. Appl. No. 13/580,129, 7 pages.
Winters et al., entitled Pharmaceutical Compositions of Spiro-Oxindole Compound for Topical Administration and Their Use as Therapeutic Agents, Restriction Requirement mailed Nov. 19, 2013, for U.S. Appl. No. 13/580,129, 7 pages.
Winters et al., entitled Pharmaceutical Compositions of Spiro-Oxindole Compound for Topical Administration and Their Use as Therapeutic Agents, Response to Requirement for Unity of Invention dated Feb. 19, 2014, for U.S. Appl. No. 13/580,129, 3 pages.
Winters et al., entitled Pharmaceutical Compositions of Spiro-Oxindole Compound for Topical Administration and Their Use as Therapeutic Agents, Office Action mailed May 7, 2014, for U.S. Appl. No. 13/580,129, 52 pages.
Winters et al., entitled Pharmaceutical Compositions of Spiro-Oxindole Compound for Topical Administration and Their Use as Therapeutic Agents, Amendment dated Aug. 7, 2014, for U.S. Appl. No. 13/580,129, 10 pages.
Winters et al., entitled Pharmaceutical Compositions of Spiro-Oxindole Compound for Topical Administration and Their Use as Therapeutic Agents, Office Action mailed Oct. 31, 2014, for U.S. Appl. No. 13/580,129, 16 pages.
Winters et al., entitled Pharmaceutical Compositions of Spiro-Oxindole Compound for Topical Administration and Their Use as Therapeutic Agents, Amendment dated Feb. 2, 2015, for U.S. Appl. No. 13/580,129, 8 pages.
Winters et al., entitled Pharmaceutical Compositions of Spiro-Oxindole Compound for Topical Administration and Their Use as Therapeutic Agents, Office Action mailed Apr. 6, 2015, for U.S. Appl. No. 13/580,129, 14 pages.
Winters et al., entitled Pharmaceutical Compositions of Spiro-Oxindole Compound for Topical Administration and Their Use as Therapeutic Agents, Amendment dated Oct. 6, 2015, for U.S. Appl. No. 13/580,129, 8 pages.
Translation of Official Action from State Intellectual Property Office of China, dated Sep. 21, 2015, for Patent Application No. 201380030552.0, 13 pages.

ASYMMETRIC SYNTHESES FOR SPIRO-OXINDOLE COMPOUNDS USEFUL AS THERAPEUTIC AGENTS

CROSS-REFERENCE TO RELATED APPLICATION

This application claims the benefit under 35 U.S.C. §119 (e) of U.S. Provisional Patent Application No. 61/623,336, filed Apr. 12, 2012. This application is incorporated herein by reference in its entirety.

FIELD OF THE INVENTION

The present invention is directed to improved methods of preparing certain spiro-oxindole compounds as well as various intermediates involved therein. In particular, this invention is directed to asymmetric syntheses of certain spiro-oxindole compounds, and their pharmaceutically acceptable salts, which are useful in treating sodium channel-mediated diseases or conditions, such as pain, as well as other diseases and conditions associated with the mediation of sodium channels.

BACKGROUND OF THE INVENTION

Sodium channels play a diverse set of roles in maintaining normal and pathological states, including the long recognized role that voltage gated sodium channels play in the generation of abnormal neuronal activity and neuropathic or pathological pain. Damage to peripheral nerves following trauma or disease can result in changes to sodium channel activity and the development of abnormal afferent activity including ectopic discharges from axotomised afferents and spontaneous activity of sensitized intact nociceptors. These changes can produce long-lasting abnormal hypersensitivity to normally innocuous stimuli, or allodynia. Examples of neuropathic pain include, but are not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

There have been some advances in treating neuropathic pain symptoms by using medications, such as gabapentin, and more recently pregabalin, as short-term, first-line treatments. However, pharmacotherapy for neuropathic pain has generally had limited success with little response to commonly used pain reducing drugs, such as NSAIDS and opiates. Consequently, there is still a considerable need to explore novel treatment modalities.

There remain a limited number of potent effective sodium channel blockers with a minimum of adverse events in the clinic. There is also an unmet medical need to treat neuropathic pain and other sodium channel associated pathological states effectively and without adverse side effects.

PCT Published Patent Application No. WO 2006/110917, PCT Published Patent Application No. WO 2010/045251, PCT Published Patent Application No. WO 2010/045197, PCT Published Patent Application No. WO 2011/047174 and PCT Published Patent Application No. WO 2011/002708 discloses certain spiro-oxindole compounds. These compounds are disclosed therein as being useful for the treatment of sodium channel-mediated diseases, preferably diseases related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome; neuroprotection against stroke, neural trauma and multiple sclerosis; and channelopathies such as erythromelalgia and familial rectal pain syndrome.

Methods of preparing these compounds and pharmaceutical compositions containing them are also disclosed in PCT Published Patent Application No. WO 2006/110917, PCT Published Patent Application No. WO 2010/045251, PCT Published Patent Application No. WO 2010/045197, PCT Published Patent Application No. WO 2011/047174 and PCT Published Patent Application No. WO 2011/002708.

There exists, therefore, a need for additional methods of preparing certain spiro-oxindole compounds.

SUMMARY OF THE INVENTION

The present invention is directed to asymmetric syntheses of certain spiro-oxindole compounds as enantiomers, or as pharmaceutically acceptable salts thereof. These compounds, which are disclosed in PCT Published Patent Application No. WO 2006/110917, PCT Published Patent Application No. WO 2010/045251, PCT Published Patent Application No. WO 2011/047174, PCT Published Patent Application No. WO 2011/002708, PCT Published Patent Application No. WO 2011/047173, and/or PCT Published Patent Application No. WO 2011/106729, are useful in treating sodium channel-mediated diseases and conditions, such as pain.

Accordingly, in one aspect, this invention is directed to methods of preparing a compound of formula (I):

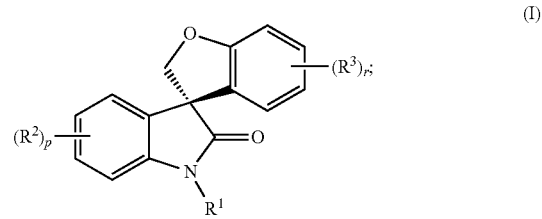

as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

wherein:

p and r are each independently 1, 2, 3 or 4;

$R^1$ is hydrogen, alkyl, alkenyl, alkynyl, haloalkyl, aryl, cycloalkyl, cycloalkylalkyl, heteroaryl, heterocyclyl, $-R^8-C(O)R^5$, $-R^8-C(O)OR^5$, $-R^8-C(O)N(R^4)R^5$, $-S(O)_2-R^5$, $-R^9-S(O)_m-R^5$ (where m is 0, 1 or 2), $-R^8-OR^5$, $-R^8-CN$, $-R^9-P(O)(OR^5)_2$, or $-R^9-O-R^9-OR^5$;

or $R^1$ is aralkyl substituted by $-C(O)N(R^6)R^7$ where:
  $R^6$ is hydrogen, alkyl, aryl or aralkyl; and
  $R^7$ is hydrogen, alkyl, haloalkyl, $-R^9-CN$, $-R^9-OR^5$, $-R^9-N(R^4)R^5$, aryl, aralkyl, cycloalkyl, cycloalkylalkyl, heterocyclyl, heterocyclylalkyl, heteroaryl or heteroarylalkyl;
  or $R^6$ and $R^7$, together with the nitrogen to which they are attached, form a N-heterocyclyl or a N-heteroaryl;

and wherein each aryl, aralkyl, cycloalkyl, cycloalkylalkyl, heterocyclyl, heterocyclylalkyl, heteroaryl and heteroarylalkyl groups for $R^6$ and $R^7$ may be optionally substituted by one or more substituents selected from the group consisting of alkyl, cycloalkyl, aryl, aralkyl, halo, haloalkyl, $-R^8-CN$, $-R^8-OR^5$, heterocyclyl and heteroaryl;

or $R^1$ is aralkyl optionally substituted by one or more substituents selected from the group consisting of $-R^8-OR^5$, $-C(O)OR^5$, halo, haloalkyl, alkyl, nitro, cyano, aryl, aralkyl, heterocyclyl and heteroaryl;

or $R^1$ is $-R^9-N(R^{10})R^{11}$, $-R^9-N(R^{12})C(O)R^{11}$ or $-R^9-N(R^{10})C(O)N(R^{10})R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, $-R^9-OC(O)R^5$, $-R^9-C(O)OR^5$, $-R^9-C(O)N(R^4)R^5$, $-R^9-C(O)R^5$, $-R^9-N(R^4)R^5$, $-R^9-OR^5$, or $-R^9-CN$; and $R^{12}$ is hydrogen, alkyl, aryl, aralkyl or $-C(O)R^5$;

and wherein each aryl, aralkyl, cycloalkyl, cycloalkylalkyl, heterocyclyl, heterocyclylalkyl, heteroaryl and heteroarylalkyl for $R^{10}$ and $R^{11}$ may be optionally substituted by one or more substituents selected from the group consisting of alkyl, cycloalkyl, aryl, aralkyl, halo, haloalkyl, nitro, $-R^8-CN$, $-R^8-OR^5$, $-R^8-C(O)R^5$, heterocyclyl and heteroaryl;

or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, $-R^8-OR^5$, $-R^8-C(O)OR^5$, $-R^8-N(R^4)R^5$, $-R^8-C(O)N(R^4)R^5$, $-R^8-N(R^5)C(O)R^4$, $-R^8-S(O)_mR^4$ (where m is 0, 1 or 2), $-R^8-CN$, or $-R^8-NO_2$;

each $R^2$ is independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $-R^8-CN$, $-R^8-NO_2$, $-R^8-OR^5$, $-R^8-N(R^4)R^5$, $-N=C(R^4)R^5$, $-S(O)_mR^4$, $-OS(O)_2CF_3$, $-R^8-C(O)R^4$, $-C(S)R^4$, $-C(R^4)_2C(O)R^5$, $-R^8-C(O)OR^4$, $-C(S)OR^4$, $-R^8-C(O)N(R^4)R^5$, $-C(S)N(R^4)R^5$, $-N(R^5)C(O)R^4$, $-N(R^5)C(S)R^4$, $-N(R^5)C(O)OR^4$, $-N(R^5)C(S)OR^4$, $-N(R^5)C(O)N(R^4)R^5$, $-N(R^5)C(S)N(R^4)R^5$, $-N(R^5)S(O)_nR^4$, $-N(R^5)S(O)_nN(R^4)R^5$, $-R^8-S(O)_nN(R^4)R^5$, $-N(R^5)C(=NR^5)N(R^4)R^5$, and $-N(R^5)C(=N-CN)N(R^4)R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^2$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $-R^8-CN$, $-R^8-NO_2$, $-R^8-OR^5$, $-R^5-N(R^4)R^5$, $-S(O)_mR^4$, $-R^8-S(O)_nN(R^4)R^5$, $-R^8-C(O)R^4$, $-R^8-C(O)OR^4$, $-R^8-C(O)N(R^4)R^5$, $-N(R^5)C(O)R^4$, and $-N(R^5)S(O)_nR^4$, wherein each m is independently 0, 1, or 2 and each n is independently 1 or 2;

or any two adjacent $R^2$'s, together with the adjacent carbon ring atoms to which they are directly attached, may form a fused ring selected from cycloalkyl, aryl, heterocyclyl and heteroaryl, and the other $R^2$'s, if present, are as defined above;

each $R^3$ is independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $-R^8-CN$, $-R^8-NO_2$, $-R^8-OR^5$, $-R^8-N(R^4)R^5$, $-N=C(R^4)R^5$, $-S(O)_mR^4$, $-OS(O)_2CF_3$, $-R^8-C(O)R^4$, $-C(S)R^4$, $-C(R^4)_2C(O)R^5$, $-R^8-C(O)OR^4$, $-C(S)OR^4$, $-R^8-C(O)N(R^4)R^5$, $-C(S)N(R^4)R^5$, $-N(R^5)C(O)R^4$, $-N(R^5)C(S)R^4$, $-N(R^5)C(O)OR^4$, $-N(R^5)C(S)OR^4$, $-N(R^5)C(O)N(R^4)R^5$, $-N(R^5)C(S)N(R^4)R^5$, $-N(R^5)S(O)_nR^4$, $-N(R^5)S(O)_nN(R^4)R^5$, $-R^8-S(O)_nN(R^4)R^5$, $-N(R^5)C(=NR^5)N(R^4)R^5$, and $-N(R^5)C(N=C(R^4)R^5)N(R^4)R^5$, wherein each m is independently 0, 1, or 2 and each n is independently 1 or 2;

or any two adjacent $R^3$'s, together with the adjacent carbon ring atoms to which they are directly attached, may form a fused ring selected from cycloalkyl, heterocyclyl, aryl or heteroaryl, and the other $R^3$'s, if present, are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a N-heterocyclyl or a N-heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain;

or a pharmaceutically acceptable salt thereof.

One method of preparing the compound of formula (I), as described above, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof; comprises treating a compound of formula (13):

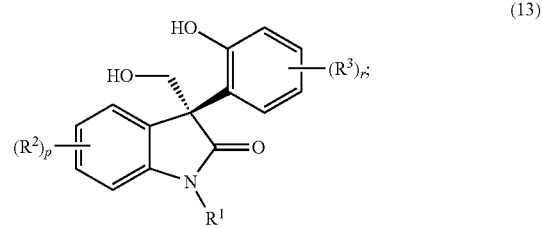

(13)

where p, r, $R^1$, $R^2$ and $R^3$ are as defined above for the compound of formula (I), as an isolated (S)-enantiomer, or as a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, under suitable Mitsunobu reaction conditions to provide the compound of formula (I), as described above.

Another method of preparing the compound of formula (I), as described above, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof; comprises treating a compound of formula (22):

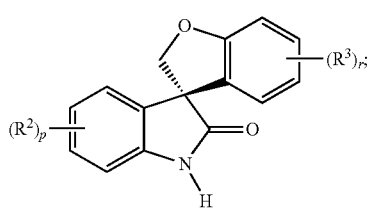

(22)

where p, r, $R^2$ and $R^3$ are as described above for the compound of formula (I), as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, with a compound of formula (2):

X—$R^1$ (2);

where X is halo, typically iodo, bromo or chloro, preferably bromo or chloro, and $R^1$ is as described above for the compound of formula (I), or a pharmaceutically acceptable salt thereof, under suitable N-alkylation conditions to provide a compound of formula (I), as described above.

Another method of preparing the compound of formula (I), as described above, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof; comprises the following steps:

(a) treating a compound of formula (1):

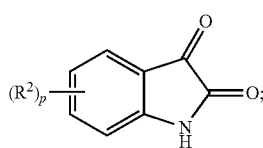

(1)

where p and $R^2$ are as described above for the compound of formula (I), or a pharmaceutically acceptable salt thereof, with a compound of formula (2):

X—$R^1$ (2);

where $R^1$ is a defined above for the compound of formula (I) and X is halo, typically iodo, bromo or chloro, preferably bromo or chloro, under suitable N-alkylation conditions to provide a compound of formula (3):

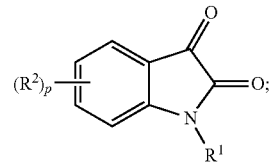

(3)

where p, $R^1$ and $R^2$ are as described above for the compound of formula (I), or a pharmaceutically acceptable salt thereof;

(b) treating a compound of formula (3) under suitable Grignard reaction conditions with an intermediate product formed from the treatment of a compound of formula (4):

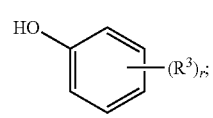

(4)

where r and $R^3$ are as defined above for the compound of formula (I), with a Grignard reagent of formula (5):

RMgX (5);

where R is alkyl and X is iodo, bromo or chloro, under suitable conditions to form a compound of formula (6):

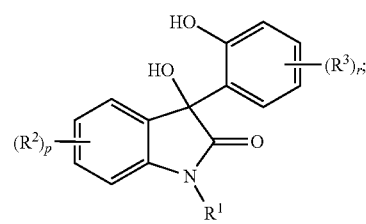

(6)

where p, r, $R^1$, $R^2$ and $R^3$ are as defined above for the compound of formula (I), as a racemic mixture of enantiomers or as a non-racemic mixture of enantiomers, or a pharmaceutically acceptable salt thereof;

(c) treating a compound of formula (6) with a compound of formula (7):

$Pg^1$X (7);

where X is halo, typically iodo, bromo or chloro, preferably bromo or chloro, and $Pg^1$ is an oxygen protecting group under suitable protecting conditions to provide a compound of formula (8):

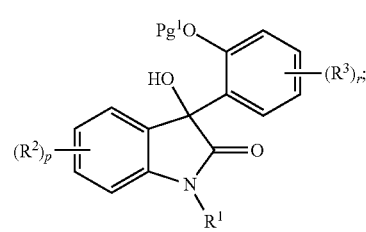

(8)

where p, r, $R^1$, $R^2$ and $R^3$ are as defined above for the compound of formula (I) and $Pg^1$ is an oxygen protecting group, as a racemic mixture of enantiomers or as a non-racemic mixture of enantiomers, or a pharmaceutically acceptable salt thereof;

(d) treating a compound of formula (8) under suitable dehydroxylation conditions to provide a compound of formula (9):

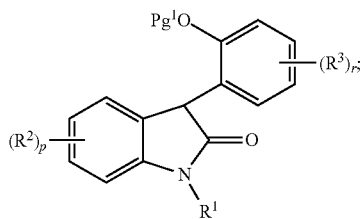

(9)

where p, r, $R^1$, $R^2$ and $R^3$ are as defined above for the compound of formula (I) and $Pg^1$ is an oxygen protecting group, as a racemic mixture of enantiomers or as a non-racemic mixture of enantiomers, or a pharmaceutically acceptable salt thereof;

(e) treating a compound of formula (9) with a compound of formula (10):

$$Pg^2OCH_2X \quad (10);$$

where $Pg^2$ is an oxygen protecting group and X is halo, typically iodo, bromo or chloro, preferably bromo or chloro, under suitable C-alkylation conditions comprising the presence of a phase transfer catalyst to provide a compound of formula (11):

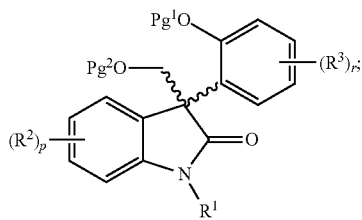

(11)

where p, r, $R^1$, $R^2$ and $R^3$ are each as defined above for the compound of formula (I) and $Pg^1$ and $Pg^2$ are each independently an oxygen protecting group, as a racemic mixture of enantiomers or as a non-racemic mixture of enantiomers, or a pharmaceutically acceptable salt thereof;

(f) treating a compound of formula (11) under suitable recrystallization conditions to provide a compound of formula (12):

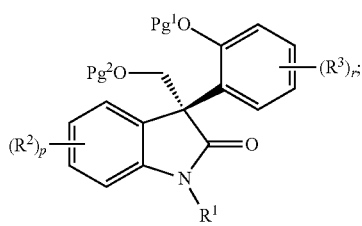

(12)

where p, r, $R^1$, $R^2$ and $R^3$ are as defined above for the compounds of formula (I) and $Pg^1$ and $Pg^2$ are each independently an oxygen protecting group, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(g) treating a compound of formula (12) under suitable deprotecting conditions to provide a compound of formula (13):

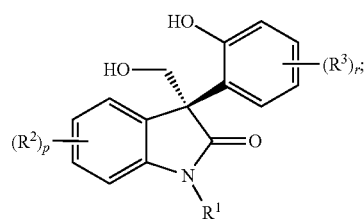

(13)

where p, r, $R^1$, $R^2$ and $R^3$ are as defined above for the compounds of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(h) treating a compound of formula (13) under suitable Mitsunobu reaction conditions to provide the compound of formula (I), as described above, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Another method of preparing the compound of formula (I), as described above, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof; comprises the following steps:

(a) treating a compound of formula (1):

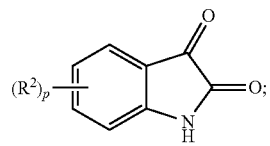

(1)

where p and $R^2$ are each as defined above for the compound of formula (I), or a pharmaceutically acceptable salt thereof, with a compound of formula (14):

$$X\text{-}Pg^3 \quad (14);$$

where halo, typically iodo, bromo or chloro, preferably bromo or chloro, and $Pg^3$ is a nitrogen protecting group, under suitable nitrogen protecting conditions to provide a compound of formula (15):

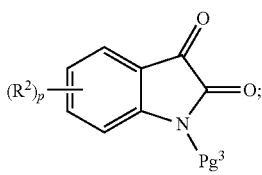

(15)

where p and R² are each as described above for the compound of formula (I), and Pg³ is a nitrogen protecting group, or a pharmaceutically acceptable salt thereof;

(b) treating a compound of formula (15) under suitable Grignard reaction conditions with an intermediate product formed from the treatment of a compound of formula (4):

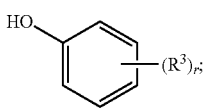

(4)

where r and R³ are each as defined above for the compound of formula (I), with a Grignard reagent of formula (5):

RMgX (5);

where R is alkyl and X is iodo, bromo or chloro, preferably bromo or chloro, under suitable conditions to provide a compound of formula (16):

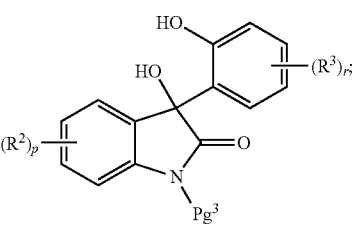

(16)

where p, r, R² and R³ are each as described above for the compound of formula (I) and Pg³ is a nitrogen protecting group, as a racemic mixture of enantiomers or as a non-racemic mixture of enantiomers, or a pharmaceutically acceptable salt thereof;

(c) treating a compound of formula (16) with a compound of formula (7):

Pg¹X (7);

where X is halo, typically iodo, bromo or chloro, preferably bromo or chloro, and Pg¹ is an oxygen protecting group under suitable protecting conditions to provide a compound of formula (17):

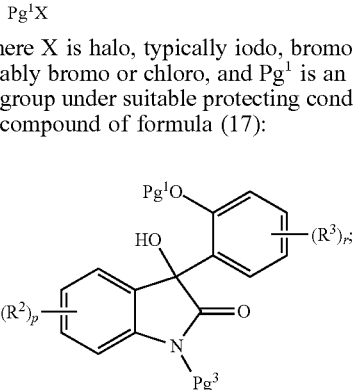

(17)

where p, r, R² and R³ are each as described above for the compound of formula (I), Pg¹ is an oxygen protecting group and Pg³ is a nitrogen protecting group, as a racemic mixture of enantiomers or as a non-racemic mixture of enantiomers, or a pharmaceutically acceptable salt thereof;

(d) treating a compound of formula (17) under suitable dehydroxylation conditions to provide a compound of formula (18):

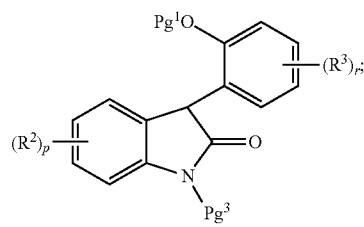

(18)

where p, r, R² and R³ are each as described above for the compound of formula (I), Pg¹ is an oxygen protecting group and Pg³ is a nitrogen protecting group, as a racemic mixture of enantiomers or as a non-racemic mixture of enantiomers, or a pharmaceutically acceptable salt thereof;

(e) treating a compound of formula (18) with a compound of formula (10):

Pg²OCH₂X (10);

where Pg² is an oxygen protecting group and X is halo, typically iodo, bromo or chloro, preferably bromo or chloro, under suitable C-alkylation conditions comprising the presence of a phase transfer catalyst to provide a compound of formula (19):

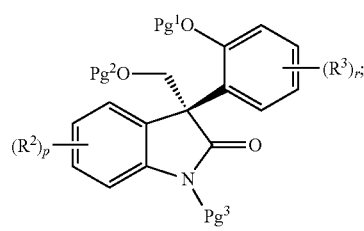

(19)

where p, r, R² and R³ are each as described above for the compound of formula (I), Pg¹ and Pg² are each independently an oxygen protecting group and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(f) treating a compound of formula (19) under suitable deprotection conditions to provide a compound of formula (20):

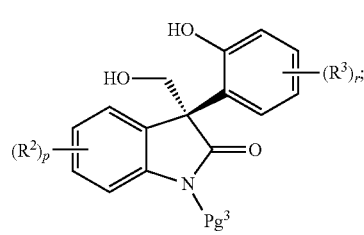

(20)

where p, r, R² and R³ are each as described above for the compound of formula (I), and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(g) treating a compound of formula (20) under suitable Mitsunobu reaction conditions to provide the compound of formula (21):

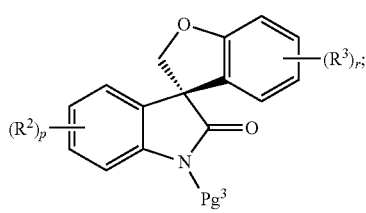

(21)

where p, r, R² and R³ are each as described above for the compound of formula (I), and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(h) treating a compound of formula (21) under suitable nitrogen deprotecting conditions to provide a compound of formula (22):

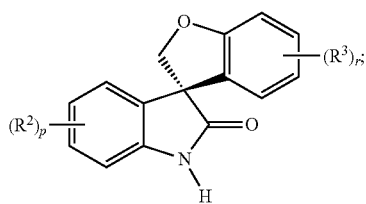

(22)

where p, r, R² and R³ are each as described above for the compound of formula (I), as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof; and (i) treating a compound of formula (22) with a compound of formula (2):

X—R¹   (2);

where X is halo, typically iodo, bromo or chloro, preferably bromo or chloro, and R¹ is as described above for the compound of formula (I), or a pharmaceutically acceptable salt thereof, under suitable N-alkylation conditions to provide a compound of formula (I), as described above, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Another aspect of this invention is a compound of formula (11):

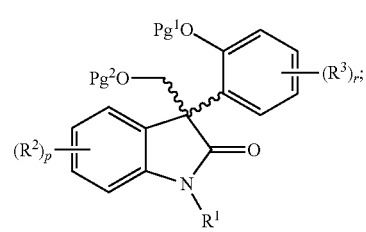

(11)

wherein p, r, R¹, R² and R³ are each as described above for the compounds of formula (I) and Pg¹ and Pg² are each independently an oxygen protecting group; as a racemic mixture of enantiomers or as a non-racemic mixture of enantiomers, or a pharmaceutically acceptable salt thereof.

Another aspect of this invention is a compound of formula (12) or a compound of formula (13):

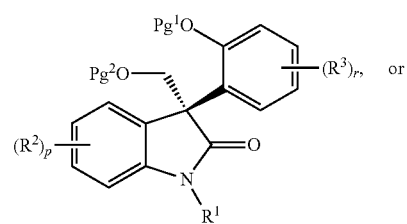

(12)

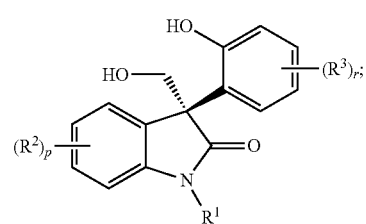

(13)

wherein each p, r, R¹, R² and R³ is as described above for the compounds of formula (I) and Pg¹ and Pg² are each independently an oxygen protecting group; as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Another aspect of this invention is a compound of formula (19), a compound of formula (20), a compound of formula (21) or a compound of formula (22):

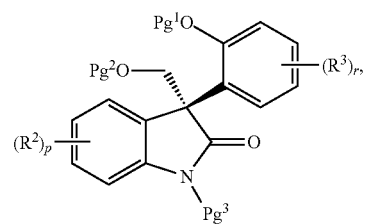

(19)

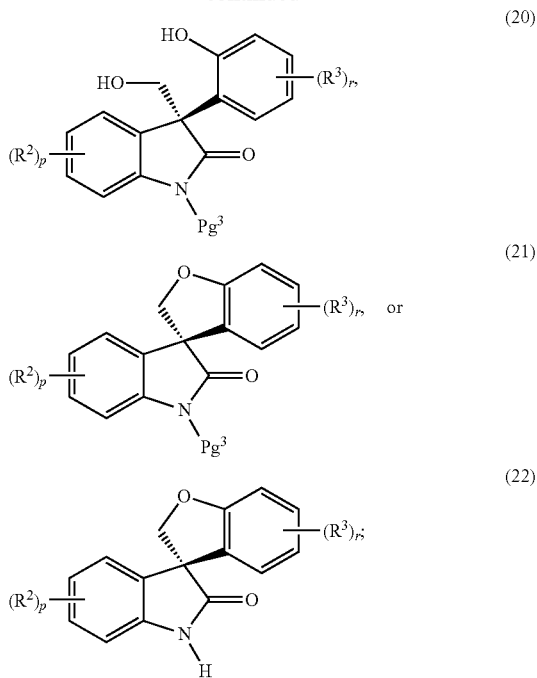

wherein each p, r, R$^1$, R$^2$ and R$^3$ is as described above for the compounds of formula (I), each Pg$^1$ and each Pg$^2$ is independently an oxygen protecting group, and each Pg$^3$ is a nitrogen protecting group; as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

These aspects of the invention and others are described in more detail below.

DETAILED DESCRIPTION OF THE INVENTION

Definitions

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_t$R$^{22}$ (where t is 1 to 2), —S(O)$_t$OR$^{22}$ (where t is 1 to 2), —S(O)$_p$R$^{22}$ (where p is 0 to 2), and —S(O)$_t$N(R$^{20}$)$_2$ (where t is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_t$R$^{22}$ (where t is 1 to 2), —S(O)$_t$OR$^{22}$ (where t is 1 to 2), —S(O)$_p$R$^{22}$ (where p is 0 to 2), and —S(O)$_t$N(R$^{20}$)$_2$ (where t is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms, preferably one to eight carbon atoms and which is attached to the rest of the molecule by a single bond, e.g., ethynyl, propynyl, butynyl, pentynyl, hexynyl, and the like. When specifically stated in the specification, an alkynyl group is optionally substituted by one or more of the following groups: alkyl, alkenyl, halo, haloalkenyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_t$R$^{22}$ (where t is 1 to 2), —S(O)$_t$OR$^{22}$ (where t is 1 to 2), —S(O)$_p$R$^{22}$ (where p is 0 to 2), or —S(O)$_t$N(R$^{20}$)$_2$ (where t is 1 to 2), where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. When specifically stated in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_t$R$^{22}$ (where t is 1 to 2), —S(O)$_t$OR$^{22}$ (where t is 1 to 2), —S(O)$_p$R$^{22}$ (where p is 0 to 2), and —S(O)$_t$N(R$^{20}$)$_2$ (where t is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. When specifically stated in the specification, an alkenylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —N($R^{20}$)$_2$, C(O)$R^{20}$, —C(O)O$R^{20}$, —C(O)N($R^{20}$)$_2$, —N($R^{20}$)C(O)O$R^{22}$, —N($R^{20}$)C(O)$R^{22}$, —N($R^{20}$)S(O)$_t$$R^{22}$ (where t is 1 to 2), —S(O)$_t$O$R^{22}$ (where t is 1 to 2), —S(O)$_p$$R^{22}$ (where p is 0 to 2), and —S(O)$_t$N($R^{20}$)$_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, e.g., propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. When specifically stated in the specification, an alkynylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—C(O)$R^{20}$, —N($R^{20}$)$_2$, —C(O)$R^{20}$, —C(O)O$R^{20}$, —C(O)N($R^{20}$)$_2$, —N($R^{20}$)C(O)O$R^{22}$, —N($R^{20}$)C(O)$R^{22}$, —N($R^{20}$)S(O)$_t$$R^{22}$ (where t is 1 to 2), —S(O)$_t$O$R^{22}$ (where t is 1 to 2), —S(O)$_p$$R^{22}$ (where p is 0 to 2), and —S(O)$_t$N($R^{20}$)$_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)O$R^{20}$, —$R^{21}$—C(O)N($R^{20}$)$_2$, —$R^{21}$—N($R^{20}$)C(O)O$R^{22}$, —$R^{21}$—N($R^{20}$)C(O)$R^{22}$, —$R^{21}$—N($R^{20}$)S(O)$_t$$R^{22}$ (where t is 1 to 2), —$R^{21}$—N=C(O$R^{20}$)$R^{20}$, —$R^{21}$—S(O)$_t$O$R^{22}$ (where t is 1 to 2), —$R^{21}$—S(O)$_p$$R^{22}$ (where p is 0 to 2), and —$R^{21}$—S(O)$_t$N($R^{20}$)$_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. When specifically stated in the specification, the alkylene chain part of the aralkyl radical may be optionally substituted as described above for an optionally substituted alkylene chain. When specifically stated in the specification, the aryl part of the aralkyl radical may be optionally substituted as described above for an optionally substituted aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptly, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)O$R^{20}$, —$R^{21}$—C(O)N($R^{20}$)$_2$, —$R^{21}$—N($R^{20}$)C(O)O$R^{22}$, —$R^{21}$—N($R^{20}$)C(O)$R^{22}$, —$R^{21}$—N($R^{20}$)S(O)$_t$$R^{22}$ (where t is 1 to 2), —$R^{21}$—N=C(O$R^{20}$)$R^{20}$, —$R^{21}$—S(O)$_t$O$R^{22}$ (where t is 1 to 2), —$R^{21}$—S(O)$_p$$R^{22}$ (where p is 0 to 2), and —$R^{21}$—S(O)$_t$N($R^{20}$)$_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_b$$R_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{22}$, —$R^{21}$—$N(R^{20})C(O)R^{22}$, —$R^{21}$—$N(R^{20})S(O)_tR^{22}$ (where t is 1 to 2), —$R^{21}$—$N=C(OR^{20})R^{20}$, —$R^{21}$—$S(O)_tOR^{22}$ (where t is 1 to 2), —$R^{21}$—$S(O)_pR^{22}$ (where p is 0 to 2), and —$R^{21}$—$S(O)_tN(R^{20})_2$ (where t is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. When specifically stated in the specification, an N-heterocyclyl radical may be optionally substituted as described above for an optionally substituted heterocyclyl radicals.

"Heterocyclylalkyl" refers to a radical of the formula —$R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkyene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-c]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{22}$, —$R^{21}$—$N(R^{20})C(O)R^{22}$, —$R^{21}$—$N(R^{20})S(O)_tR^{22}$ (where t is 1 to 2), —$R^{21}$—$N=C(OR^{20})R^{20}$, —$R^{21}$—$S(O)_tOR^{22}$ (where t is 1 to 2), —$R^{21}$—$S(O)_pR^{22}$ (where p is 0 to 2), and —$R^{21}$—$S(O)_tN(R^{20})_2$ (where t is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen and where the point of attachment of the heteroaryl radical to the rest of the molecule is through a nitrogen atom in the heteroaryl radical. When specifically stated in the specification, an N-heteroaryl radical may be optionally substituted as described above for an optionally substituted heteroaryl radicals.

"Heteroarylalkyl" refers to a radical of the formula —$R_bR_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Stable compound" and "stable structure" are meant to indicate a compound that is sufficiently robust to survive isolation to a useful degree of purity from a reaction mixture, and formulation into an efficacious therapeutic agent.

The compounds prepared herein may contain one or more asymmetric centres and may thus give rise to enantiomers that may be defined, in terms of absolute stereochemistry, as (R)- or (S)- or, as (D)- or (L)- for amino acids. The present invention is meant to include all such possible enantiomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation, or by the techniques disclosed herein. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

The designations "R" and "S" are used to denote the three-dimensional arrangement of atoms (or the configuration) of the stereogenic center of an enantiomer. The designations may appear as a prefix or as a suffix herein; they may or may not be separated from the enantiomer name by a hyphen; they may or may not be hyphenated; and they may or may not be surrounded by parentheses. The designations or prefixes "(+) and (−)" may be employed herein to designate the sign of rotation of plane-polarized light by the compound, with (−) meaning that the compound is levorotatory (rotates to the left). A compound prefixed with (+) is dextrorotatory (rotates to the right).

"Resolution" or "resolving" when used in reference to a racemic compound or mixture refers to the separation of a racemate into its two enantiomeric forms (i.e., (+) and (−); (R) and (S) forms).

"Enantiomeric excess" or "ee" refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this invention, a compound prepared by the methods disclosed herein may exist as an isolated (S)-enantiomer or a non-racemic mixture where the (S)-enantiomer is present in enantiomeric excess of greater than 80%, preferably greater than 90%, more preferably greater than 95% and most preferably greater than 99% of the (R)-enantiomer.

The chemical naming protocol and structure diagrams used herein are a modified form of the I.U.P.A.C. nomenclature system, using the ACD/Name Version 9.07 software program. For complex chemical names employed herein, a substituent group is named before the group to which it attaches. For example, cyclopropylethyl comprises an ethyl backbone with cyclopropyl substituent. In the chemical structure diagrams herein all bonds are identified, except for some carbon atoms, which are assumed to be bonded to sufficient hydrogen atoms to complete the valency. Stereochemistry is designated herein through the use of the conventional solid wedge bonds and dashed wedge bonds, i.e., a solid wedge bond indicates that the bond is above the plane of the paper and a dashed wedge bond indicates that the bond is below the plane of the paper. Wavy bonds are intended to indicate that the bonds are either above the plane of the paper or below the plane of the paper. Straight bonds are intended to include all possible stereochemical configurations.

Thus, for example, a compound of formula (I) herein, i.e., the compound of formula (Ia1):

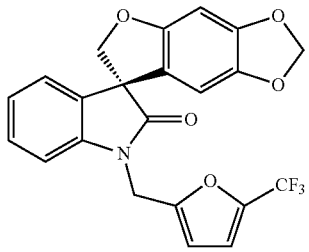
(Ia1)

is named herein as (S)-1'-{[5-(trifluoromethyl)furan-2-yl]methyl}spiro[furo[2,3-f][1,3]benzodioxole-7,3'-indol]-2'(1'H)-one.

EMBODIMENTS OF THE INVENTION

Of the various aspects of the invention disclosed above in the Summary of the Invention, certain embodiments are preferred.

One aspect of the invention described herein is a method of preparing a compound of formula (I), as described above in the Summary of the Invention; as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, wherein the method comprises treating a compound of formula (13):

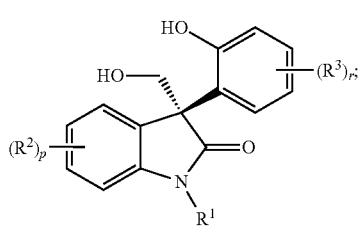
(13)

where p, r, $R^1$, $R^2$ and $R^3$ are as described above in the Summary of the Invention for the compound of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, under suitable Mitsunobu reaction conditions to provide the compound of formula (I), as described above in the Summary of the Invention. The compound of formula (I) is preferably a compound of formula (Ia):

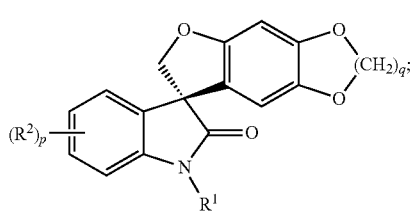
(Ia)

where q is 1 or 2 and p, $R^1$ and $R^2$ are each as described above in the Summary of the Invention for the compound of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably the compound of formula (I) is a compound of formula (Ia1):

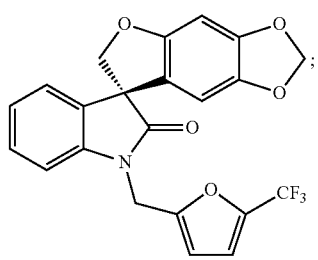
(Ia1)

as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

The compound of formula (13) is preferably a compound of formula (13a):

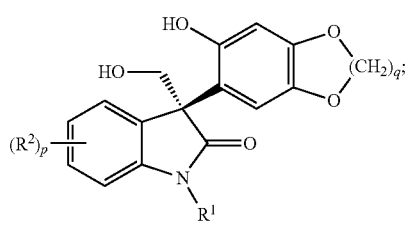
(13a)

where q is 1 or 2 and p, $R^1$ and $R^2$ are each as described above in the Summary of the Invention for the compounds of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (13a) is a compound of formula (13a1):

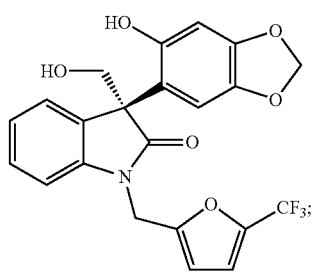
(13a1)

as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

The method described above for treating the compound of formula (13) under standard Mitsunobu reaction conditions to form the compound of formula (I) may further comprise a deprotection step prior to treating the compound of formula (13), wherein the deprotection step comprises treating a compound of formula (12):

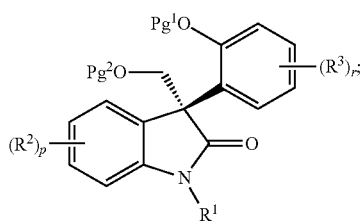

(12)

wherein p, r, $R^1$, $R^2$ and $R^3$ are each as described above in the Summary of the Invention for the compounds of formula (I) and $Pg^1$ and $Pg^2$ are each independently an oxygen protecting group, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, under suitable deprotecting conditions to provide a compound of formula (13), as described above. Preferably, the compound of formula (12) is a compound of formula (12a):

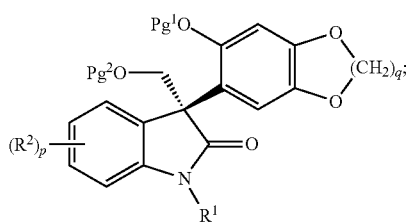

(12a)

where q is 1 or 2, $Pg^1$ and $Pg^2$ are each independently an oxygen protecting group and p, $R^1$ and $R^2$ are each as described above in the Summary of the Invention for the compounds of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (I2a) is a compound of formula (12a1):

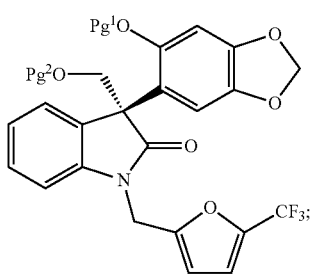

(12a1)

where $Pg^1$ and $Pg^2$ are each independently an oxygen protecting group, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

The method described above for treating a compound of formula (12) under suitable deprotecting conditions to provide a compound of formula (13) may further comprise a recrystallization step prior to treating the compound of formula (12), wherein the recrystallization step comprises treating a compound of formula (11):

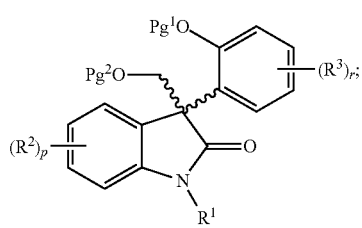

(11)

wherein p, r, $R^1$, $R^2$ and $R^3$ are each as described above in the Summary of the Invention for the compounds of formula (I) and $Pg^1$ and $Pg^2$ are each independently an oxygen protecting group, as a racemic mixture of enantiomers or as a non-racemic mixture of enantiomers, or a pharmaceutically acceptable salt thereof, under suitable recrystallization conditions to provide a compound of formula (12), as described above. Preferably, the compound of formula (11) is a compound of formula (11a):

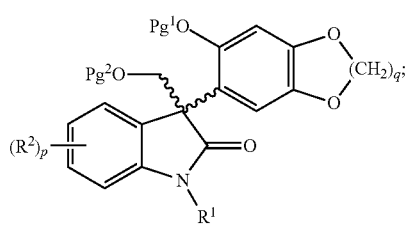

(11a)

where q is 1 or 2, p, $R^1$ and $R^2$ are each as described above in the Summary of the Invention for the compounds of formula (I) and $Pg^1$ and $Pg^2$ are each independently an oxygen protecting group, as a racemic mixture of enantiomers or as a non-racemic mixture of enantiomers, or a pharmaceutically acceptable salt thereof. More preferably, the compound of formula (11a) is a compound of formula (11a1):

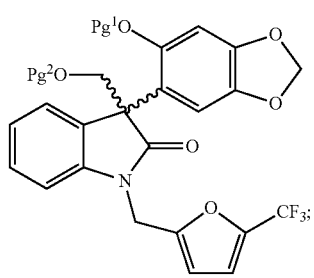

(11a1)

where $Pg^1$ and $Pg^2$ are each independently an oxygen protecting group, as a racemic mixture of enantiomers or as a non-racemic mixture of enantiomers, or a pharmaceutically acceptable salt thereof.

The method described above for treating a compound of formula (11) under suitable recrystallization conditions to provide a compound of formula (12) may further comprise a C-alkylation step prior to treating the compound of formula (11), wherein the C-alkylation step comprises treating a compound of formula (9):

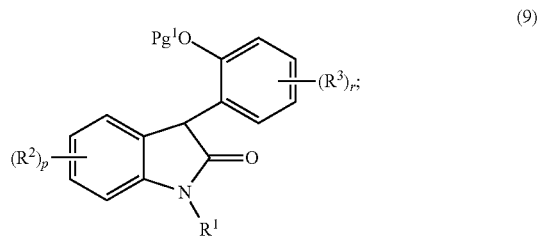

(9)

where p, r, $R^1$, $R^2$ and $R^3$ are each as described above in the Summary of the Invention for the compounds of formula (I) and $Pg^1$ is an oxygen protecting group, as a racemic mixture of enantiomers or as a non-racemic mixture of enantiomers, or a pharmaceutically acceptable salt thereof, with a compound of formula (10):

$Pg^2OCH_2X$ (10);

under suitable C-alkylation conditions comprising the presence of a phase transfer catalyst to provide a compound of formula (11), as described above. Preferably, the compound of formula (9) is a compound of formula (9a):

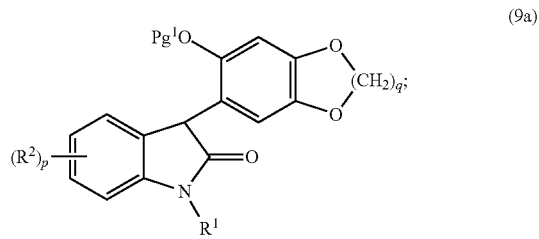

(9a)

where q is 1 or 2, p, $R^1$ and $R^2$ are each as described above in the Summary of the Invention for the compounds of formula (I) and $Pg^1$ is an oxygen protecting group, as a racemic mixture of enantiomers or as a non-racemic mixture of enantiomers, or a pharmaceutically acceptable salt thereof. More preferably, the compound of formula (9a) is a compound of formula (9a1):

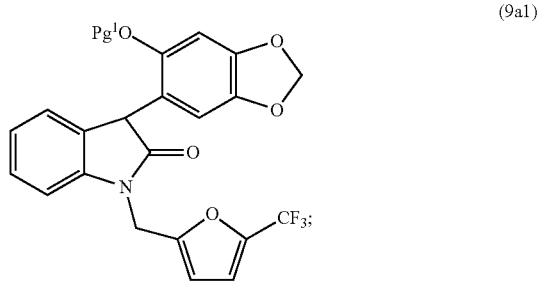

(9a1)

where $Pg^1$ is an oxygen protecting group, as a racemic mixture of enantiomers or as a non-racemic mixture of enantiomers, or a pharmaceutically acceptable salt thereof.

Preferably the phase transfer catalyst used in the C-alkylation step described above is a quaternary ammonium salt of quinidine or a quaternary ammonium salt of cinchonine.

The method described above for treating a compound of formula (9) with a compound of formula (10) under suitable C-alkylation conditions to provide a compound of formula (II) may further comprise a dehydroxylation step prior to treating the compound of formula (9), wherein the dehydroxylation step comprises treating a compound of formula (8):

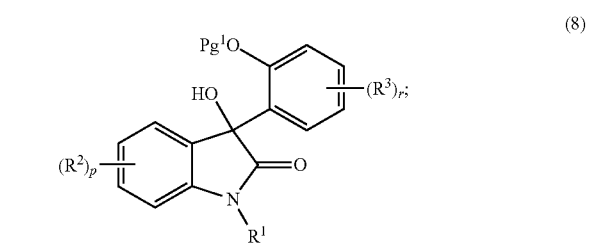

(8)

where p, r, $R^1$, $R^2$ and $R^3$ are each as described above in the Summary of the Invention for the compounds of formula (I) and $Pg^1$ is an oxygen protecting group, as a racemic mixture of enantiomers or as a non-racemic mixture of enantiomers, or a pharmaceutically acceptable salt thereof, under suitable dehydroxylation conditions to provide a compound of formula (9), as described above. Preferably, the compound of formula (8) is a compound of formula (8a):

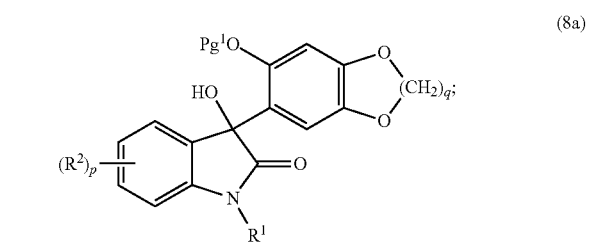

(8a)

where q is 1 or 2, p, $R^1$ and $R^2$ are each as described above in the Summary of the Invention for the compounds of formula (I) and $Pg^1$ is an oxygen protecting group, as a racemic mixture of enantiomers or as a non-racemic mixture of enantiomers, or a pharmaceutically acceptable salt thereof. More preferably, the compound of formula (8a) is a compound of formula (8a1):

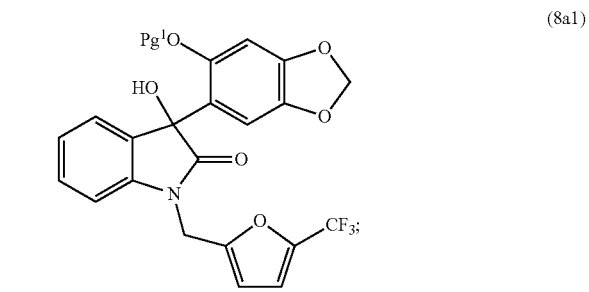

(8a1)

where $Pg^1$ is an oxygen protecting group, as a racemic mixture of enantiomers or as a non-racemic mixture of enantiomers, or a pharmaceutically acceptable salt thereof.

The method described above for treating a compound of formula (8) under suitable dehydroxylation conditions to provide a compound of formula (9) may further comprise a protecting step prior to treating the compound of formula (8), wherein the protecting step comprises treating a compound of formula (6):

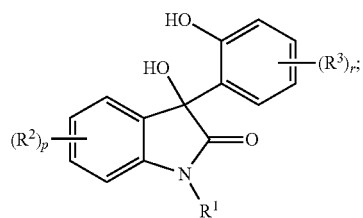

where p, r, $R^1$, $R^2$ and $R^3$ are each as described above in the Summary of the Invention for the compounds of formula (I), as a racemic mixture of enantiomers or as a non-racemic mixture of enantiomers, or a pharmaceutically acceptable salt thereof, with a compound of formula (7):

where X is halo, typically iodo, bromo or chloro, preferably bromo or chloro, and $Pg^1$ is an oxygen protecting group under suitable protecting conditions to provide a compound of formula (8), as described above. Preferably the compound of formula (6) is a compound of formula (6a):

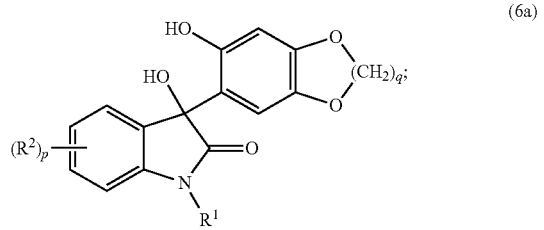

where q is 1 or 2 and p, $R^1$ and $R^2$ are each as described above in the Summary of the Invention for the compounds of formula (I), as a racemic mixture of enantiomers or as a non-racemic mixture of enantiomers, or a pharmaceutically acceptable salt thereof. More preferably, the compound of formula (6a) is a compound of formula (6a1):

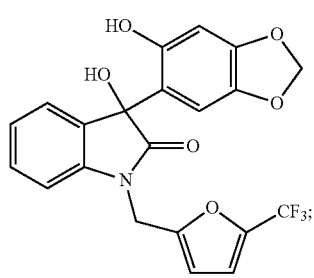

as a racemic mixture of enantiomers or as a non-racemic mixture of enantiomers, or a pharmaceutically acceptable salt thereof.

The method described above for treating a compound of formula (6) with a compound of formula (7) under suitable protecting conditions to provide a compound of formula (8) may further comprise a Grignard addition step, wherein the Grignard addition step comprises first treating a compound of formula (4):

where r and $R^3$ are as described above for the compound of formula (I), with a Grignard reagent of formula (5):

where X is iodo, bromo or chloro, preferably bromo or chloro, and R is alkyl, under suitable conditions to form an intermediate Grignard addition product; and then treating a compound of formula (3):

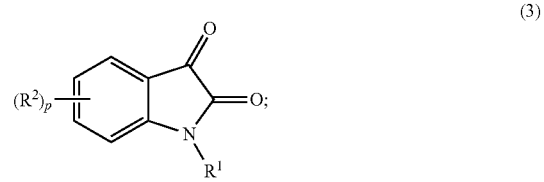

where p, $R^1$ and $R^2$ are each as described above in the Summary of the Invention for the compounds of formula (I), or a pharmaceutically acceptable salt thereof, with the intermediate Grignard addition product formed above under suitable Grignard reaction conditions to provide a compound of formula (6), as described above. Preferably the compound of formula (3) is a compound of formula (3a):

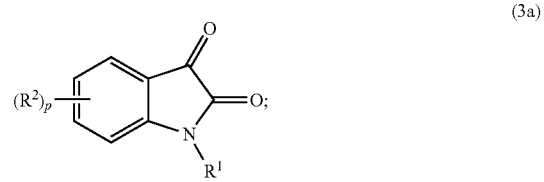

where p, $R^1$ and $R^2$ are each as described above in the Summary of the Invention for the compounds of formula (I), or a pharmaceutically acceptable salt thereof. More preferably the compound of formula (3a) is a compound of formula (3a1):

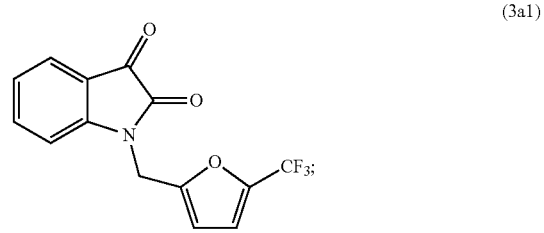 [SMILES: O=C1C(=O)N(Cc2ccc(C(F)(F)F)o2)c2ccccc21]

or a pharmaceutically acceptable salt thereof. Preferably the compound of formula (4) is a compound of formula (4a):

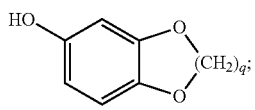

(4a)

where q is 1 or 2. More preferably, the compound of formula (4a) is a compound of formula (4a1):

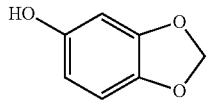

(4a1)

The method described above for first treating a compound of formula (4) with a Grignard reagent of formula (5) to form an intermediate Grignard addition product and then treating a compound of formula (3) with the intermediate Grignard addition product to provide a compound of formula (6), as described above, may further comprise a N-alkylation step prior to treating the compound of formula (3) or the compound of formula (4), wherein the N-alkylation step comprises treating a compound of formula (1):

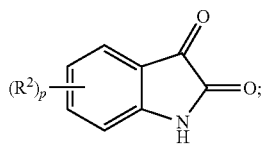

(1)

where p and $R^2$ are each as described above in the Summary of the Invention for the compounds of formula (I), or a pharmaceutically acceptable salt thereof, with a compound of formula (2):

$$X-R^1 \qquad (2);$$

where X is halo, typically iodo, bromo or chloro, preferably bromo or chloro, and $R^1$ is as described above in the Summary of the Invention for the compounds of formula (I), under suitable N-alkylation conditions to provide a compound of formula (3), as described above. Preferably, the compound of formula (1) is a compound of formula (1a):

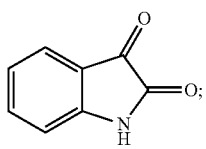

(1a)

or a pharmaceutically acceptable salt thereof. Preferably, the compound of formula (2) is a compound of formula (2a):

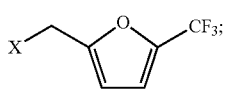

(2a)

where X is halo, typically iodo, bromo or chloro, preferably bromo or chloro.

Another aspect of the invention described herein is a method of preparing a compound of formula (I), as described above in the Summary of the Invention; wherein the method comprises the following steps:

(a) treating a compound of formula (I):

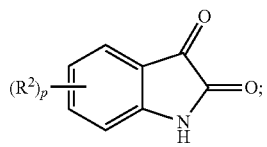

(1)

where p and $R^2$ are each as described above in the Summary of the Invention for the compound of formula (I), or a pharmaceutically acceptable salt thereof, with a compound of formula (2):

$$X-R^1 \qquad (2);$$

where $R^1$ is as described above in the Summary of the Invention for the compound of formula (I) and X is halo, typically iodo, bromo or chloro, preferably bromo or chloro, under suitable N-alkylation conditions to provide a compound of formula (3):

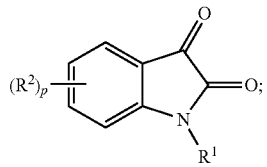

(3)

where p, $R^1$ and $R^2$ are each as described above in the Summary of the Invention for the compound of formula (I), or a pharmaceutically acceptable salt thereof;

(b) treating a compound of formula (3) under suitable Grignard reaction conditions with an intermediate Grignard addition product formed from the treatment of a compound of formula (4):

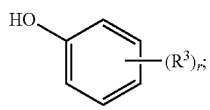

(4)

where r and $R^3$ are each as described above in the Summary of the Invention for the compound of formula (I), with a Grignard reagent of formula (5):

$$RMgX \qquad (5);$$

where R is alkyl and X is iodo, bromo or chloro, preferably bromo or chloro, under suitable conditions to form a compound of formula (6):

(6)

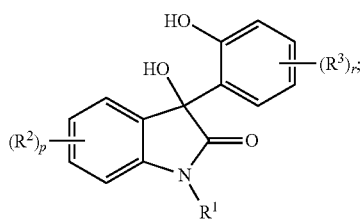

where p, r, $R^1$, $R^2$ and $R^3$ are each as described above in the Summary of the Invention for the compound of formula (I), as a racemic mixture of enantiomers or as a non-racemic mixture of enantiomers, or a pharmaceutically acceptable salt thereof;

(c) treating a compound of formula (6) with a compound of formula (7):

$Pg^1X$ (7);

where X is halo, typically iodo, bromo or chloro, preferably bromo or chloro, and $Pg^1$ is an oxygen protecting group under suitable protecting conditions to provide a compound of formula (8):

(8)

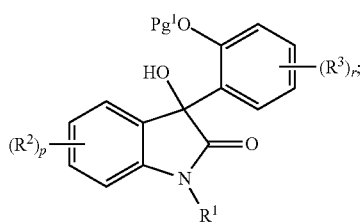

where p, r, $R^1$, $R^2$ and $R^3$ are each as described above in the Summary of the Invention for the compound of formula (I) and $Pg^1$ is an oxygen protecting group, as a racemic mixture of enantiomers or as a non-racemic mixture of enantiomers, or a pharmaceutically acceptable salt thereof;

(d) treating a compound of formula (8) under suitable dehydroxylation conditions to provide a compound of formula (9):

(9)

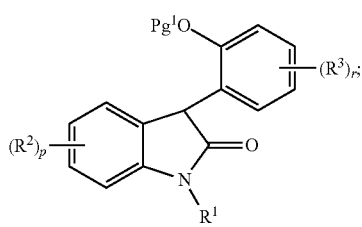

where p, r, $R^1$, $R^2$ and $R^3$ are each as described above in the Summary of the Invention for the compound of formula (I) and $Pg^1$ is an oxygen protecting group, as a racemic mixture of enantiomers or as a non-racemic mixture of enantiomers, or a pharmaceutically acceptable salt thereof;

(e) treating a compound of formula (9) with a compound of formula (10):

$Pg^2OCH_2X$ (10);

where $Pg^2$ is an oxygen protecting group and X is halo, typically iodo, bromo or chloro, preferably bromo or chloro, under suitable C-alkylation conditions comprising the presence of a phase transfer catalyst to provide a compound of formula (11):

(11)

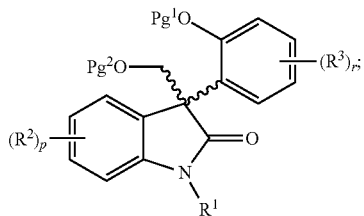

where p, r, $R^1$, $R^2$ and $R^3$ are each as described above in the Summary of the Invention for the compound of formula (I) and $Pg^1$ and $Pg^2$ are each independently an oxygen protecting group, as a racemic mixture of enantiomers or as a non-racemic mixture of enantiomers, or a pharmaceutically acceptable salt thereof;

(f) treating a compound of formula (11) under suitable recrystallization conditions to provide a compound of formula (12):

(12)

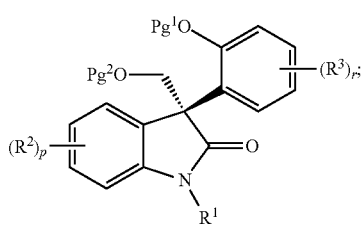

where p, r, $R^1$, $R^2$ and $R^3$ are each as described above in the Summary of the Invention for the compound of formula (I) and $Pg^1$ and $Pg^2$ are each independently an oxygen protecting group, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(g) treating a compound of formula (12) under suitable deprotecting conditions to provide a compound of formula (13):

(13)

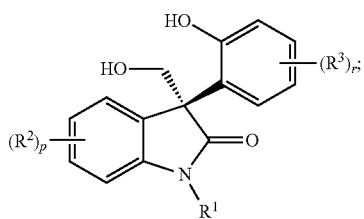

where p, r, $R^1$, $R^2$ and $R^3$ are each as described above in the Summary of the Invention for the compound of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(h) treating a compound of formula (13) under suitable Mitsunobu reaction conditions to provide the compound of formula (I), as defined above, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

A preferred method of preparing a compound of formula (I), as described above in the Summary of the Invention, is the method wherein the method comprises treating a compound of formula (22):

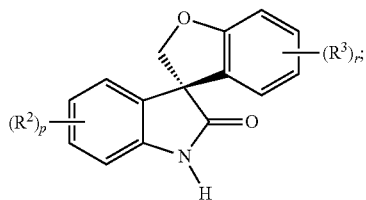

(22)

where p, r, $R^2$ and $R^3$ are each as described above in the Summary of the Invention for the compound of formula (I), as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, with a compound of formula (2):

(2);

where X is halo, typically iodo, bromo or chloro, preferably bromo or chloro, and $R^1$ is as described above in the Summary of the Invention for the compound of formula (I), or a pharmaceutically acceptable salt thereof, under suitable N-alkylation conditions to provide a compound of formula (I), as described above. Preferably, the compound of formula (I) is a compound of formula (Ia):

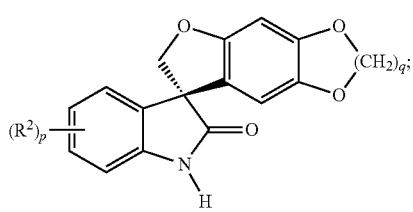

(Ia)

where q is 1 or 2 and p, $R^1$ and $R^2$ are each as described above in the Summary of the Invention for the compound of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (Ia) is a compound of formula (Ia1):

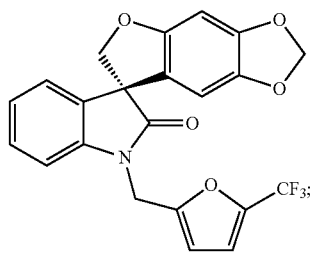

(Ia1)

as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof; or the compound of formula (Ia) is a compound of formula (Ia2):

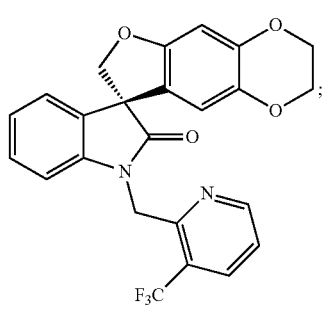

(Ia2)

as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. Preferably, the compound of formula (2) is a compound of formula (2a):

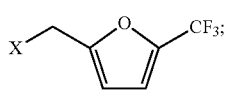

(2a)

where X is halo, typically iodo, bromo or chloro, preferably bromo or chloro, or the compound of formula (2) is a compound of formula (2b):

(2b)

where X is halo, typically iodo, bromo or chloro, preferably bromo or chloro. Preferably, the compound of formula (22) is a compound of formula (22a):

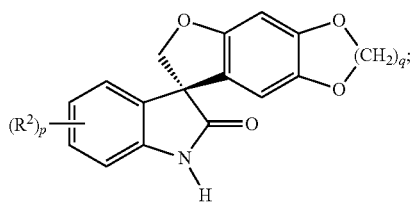

(22a)

where q is 1 or 2 and p and $R^2$ are are each as described above in the Summary of the Invention for the compound of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (22a) is a compound of formula (22a1):

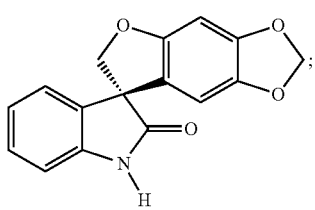

(22a1)

as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, or a compound of formula (22a2):

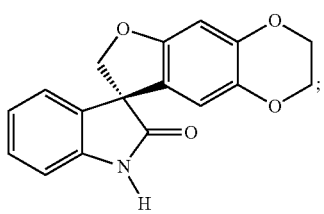

(22a2)

as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

The method described above for treating a compound of formula (22) with a compound of formula (2) under suitable N-alkylation conditions to provide a compound of formula (I), as described above, may further comprise a deprotection step prior to treating the compound of formula (22), wherein the deprotection step comprises treating a compound of formula (21):

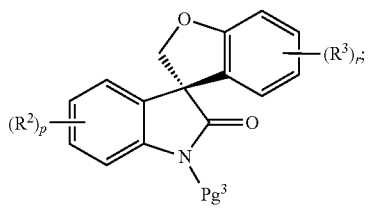

(21)

where p, r, $R^2$ and $R^3$ are each as described above in the Summary of the Invention for the compound of formula (I), and $Pg^3$ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, under suitable nitrogen deprotection conditions to provide a compound of formula (22), as described above. Preferably, the compound of formula (21) is a compound of formula (21a):

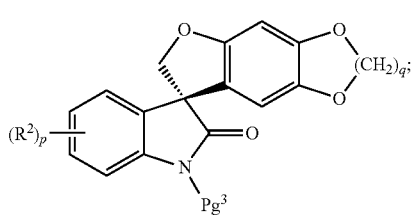

(21a)

where q is 1 or 2, p and $R^2$ are each as described above in the Summary of the Invention for the compound of formula (I) and $Pg^3$ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (21a) is a compound of formula (21a1):

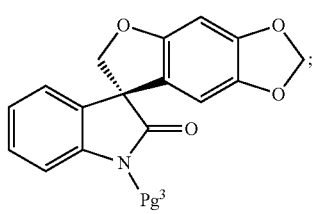

(21a1)

where $Pg^3$ is an nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, or the compound of formula (21a) is a compound of formula (21a2):

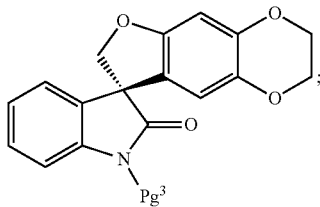
(21a2)

where Pg³ is an nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

The method described above for treating a compound of formula (21) under suitable nitrogen deprotection conditions to provide a compound of formula (22), may further comprise an intramolecular cyclization step prior to treating the compound of formula (21), as described above, where the intramolecular cyclization step comprises treating a compound of formula (20):

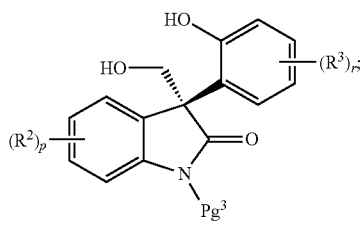
(20)

where p, r, R² and R³ are each as described above in the Summary of the Invention for the compound of formula (I), and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, under suitable Mitsunobu reaction conditions, to provide the compound of formula (21), as described above. Preferably, the compound of formula (20) is a compound of formula (20a):

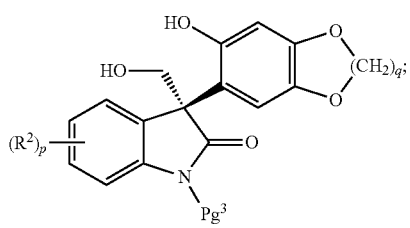
(20a)

where q is 1 or 2, p and R² are each as described above in the Summary of the Invention for the compound of formula (I) and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (20a) is a compound of formula (20a1):

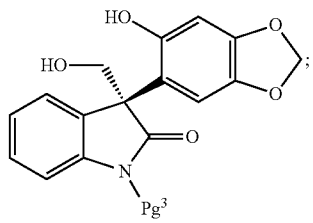
(20a1)

where Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, or the compound of formula (20a) is a compound of formula (20a2):

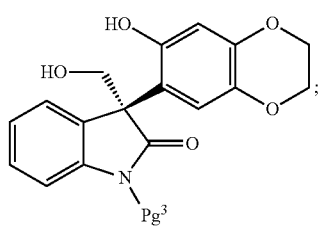
(20a2)

where Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

The method described above for treating a compound of formula (20) under standard Mitsunobu reaction conditions to provide a compound of formula (21), as described above, may further comprise a deprotection step prior to treating the compound of formula (20), as described above, wherein the deprotection step comprises treating a compound of formula (19):

(19)

where p, r, R² and R³ are each as described above in the Summary of the Invention for the compound of formula (I), Pg¹ and Pg² are each independently an oxygen protecting group and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, under suitable deprotection conditions to provide a compound of formula (20), as described above. Preferably, the compound of formula (19) is a compound of formula (19a):

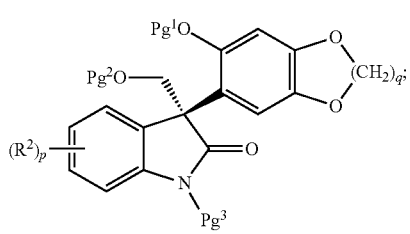

(19a)

where q is 1 or 2, p and $R^2$ are each as described above in the Summary of the Invention for the compound of formula (I), $Pg^1$ and $Pg^2$ are each independently an oxygen protecting group and $Pg^3$ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (19a) is a compound of formula (19a1):

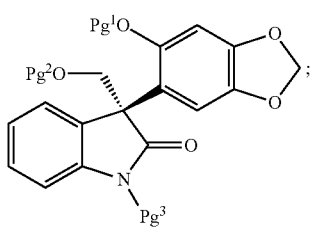

(19a1)

where $Pg^1$ and $Pg^2$ are each independently an oxygen protecting group and $Pg^3$ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof, or the compound of formula (19a) is a compound of formula (19a2):

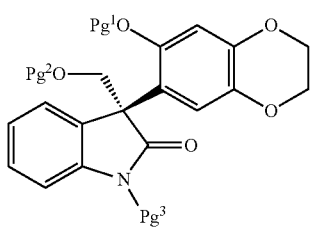

(19a2)

where $Pg^1$ and $Pg^2$ are each independently an oxygen protecting group and $Pg^3$ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

The method described above for treating a compound of formula (19) under suitable deprotection conditions to provide a compound of formula (20), as described above, may further comprise a C-alkylation step prior to treating the compound of formula (19), wherein the C-alkylation step comprises treating a compound of formula (18):

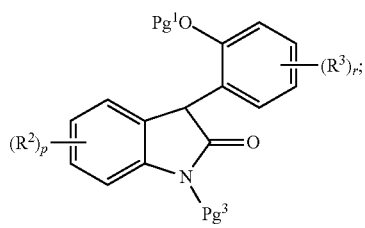

(18)

where p, r, $R^2$ and $R^3$ are each as described above in the Summary of the Invention for the compound of formula (I), $Pg^1$ is an oxygen protecting group and $Pg^3$ is a nitrogen protecting group, as a racemic mixture of enantiomers or as a non-racemic mixture of enantiomers, or a pharmaceutically acceptable salt thereof, with a compound of formula (10):

$$Pg^2OCH_2X \quad (10);$$

where X is halo, typically iodo, bromo or chloro, preferably bromo or chloro, and $Pg^2$ is an oxygen protecting group, under suitable C-alkylation conditions comprising the presence of a phase transfer catalyst to provide a compound of formula (19), as described above. Preferably, the compound of formula (18) is a compound of formula (18a):

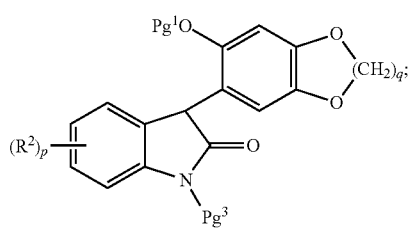

(18a)

where q is 1 or 2, p and $R^2$ are each as described above in the Summary of the Invention for the compound of formula (I), $Pg^1$ is an oxygen protecting group and $Pg^3$ is a nitrogen protecting group, as a racemic mixture of enantiomers or as a non-racemic mixture of enantiomers, or a pharmaceutically acceptable salt thereof. More preferably, the compound of formula (18a) is a compound of formula (18a1):

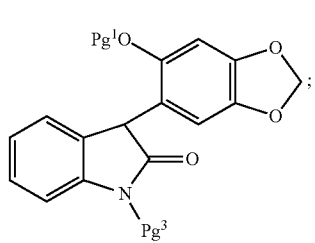

(18a1)

where Pg¹ is an oxygen protecting group and Pg³ is a nitrogen protecting group, as a racemic mixture of enantiomers or as a non-racemic mixture of enantiomers, or a pharmaceutically acceptable salt thereof, or the compound of formula (18a) is a compound of formula (18a2):

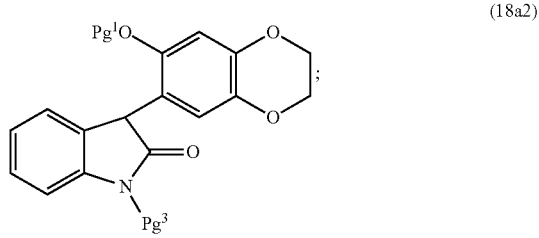

(18a2)

where Pg¹ is an oxygen protecting group and Pg³ is a nitrogen protecting group, as a racemic mixture of enantiomers or as a non-racemic mixture of enantiomers, or a pharmaceutically acceptable salt thereof. Preferably, the phase transfer catalyst utilized in this step is a quaternary ammonium salt of quinidine or a quaternary ammonium salt of cinchonine.

The method described above for treating a compound of formula (18) with a compound of formula (10) under suitable C-alkylation conditions to provide a compound of formula (19), as described above, may further comprise a dehydroxylation step prior to treating the compound of formula (18), as described above, wherein the dehydroxylation step comprises treating a compound of formula (17):

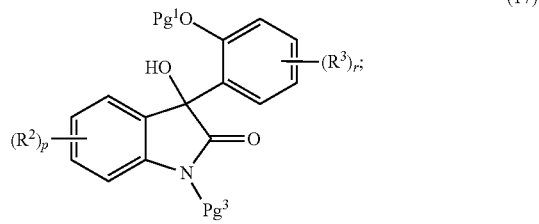

(17)

where p, r, R² and R³ are each as described above in the Summary of the Invention for the compound of formula (I), Pg¹ is an oxygen protecting group and Pg³ is a nitrogen protecting group, as a racemic mixture of enantiomers or as a non-racemic mixture of enantiomers, or a pharmaceutically acceptable salt thereof, under suitable dehydroxylation conditions to provide a compound of formula (18), as described above. Preferably, the compound of formula (17) is a compound of formula (17a):

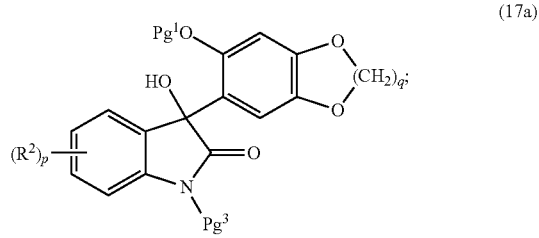

(17a)

where q is 1 or 2, p and R² are each as described above in the Summary of the Invention for the compound of formula (I), Pg¹ is an oxygen protecting group and Pg³ is a nitrogen protecting group, as a racemic mixture of enantiomers or as a non-racemic mixture of enantiomers, or a pharmaceutically acceptable salt thereof. More preferably, the compound of formula (17a) is a compound of formula (17a1):

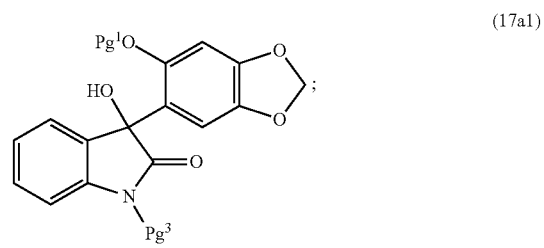

(17a1)

where Pg¹ is an oxygen protecting group and Pg³ is a nitrogen protecting group, as a racemic mixture of enantiomers or as a non-racemic mixture of enantiomers, or a pharmaceutically acceptable salt thereof, or the compound of formula (17a) is a compound of formula (17a2):

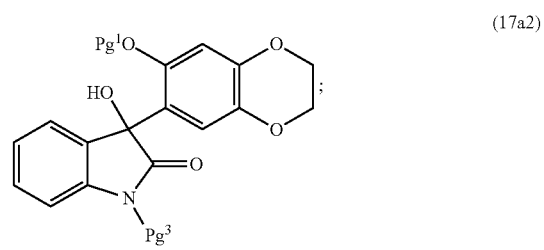

(17a2)

where Pg¹ is an oxygen protecting group and Pg³ is a nitrogen protecting group, as a racemic mixture of enantiomers or as a non-racemic mixture of enantiomers, or a pharmaceutically acceptable salt thereof.

The method described above for treating a compound of formula (17) under suitable dehydroxylation conditions to provide a compound of formula (18), as described above, may further comprise a protecting step prior to treating the compound of formula (17), as described above, wherein the protecting step comprises treating a compound of formula (16):

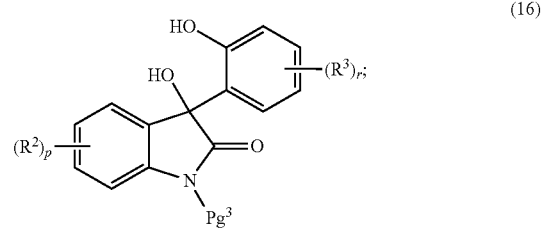

(16)

where p, r, R² and R³ are each as described above in the Summary of the Invention for the compound of formula (I) and Pg³ is a nitrogen protecting group, as a racemic mixture of enantiomers or as a non-racemic mixture of enantiomers, or a pharmaceutically acceptable salt thereof, with a compound of formula (7):

Pg¹X     (7);

where X is halo, typically iodo, bromo or chloro, preferably bromo or chloro, and Pg¹ is an oxygen protecting group under suitable protecting conditions to provide a compound of formula (17), as described above. Preferably, the compound of formula (16) is a compound of formula (16a):

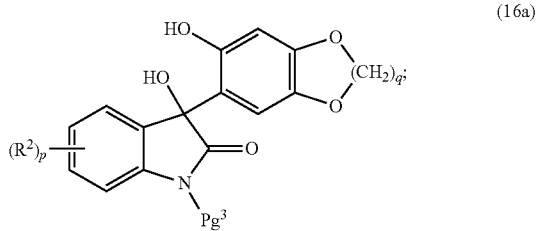

where q is 1 or 2, p and R² are each as described above in the Summary of the Invention for the compound of formula (I) and Pg³ is a nitrogen protecting group, as a racemic mixture of enantiomers or as a non-racemic mixture of enantiomers, or a pharmaceutically acceptable salt thereof. More preferably, the compound of formula (16a) is a compound of formula (16a1):

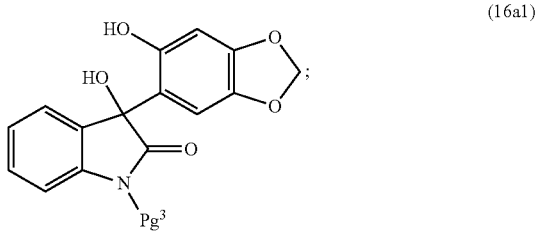

where Pg³ is a nitrogen protecting group, as a racemic mixture of enantiomers or as a non-racemic mixture of enantiomers, or a pharmaceutically acceptable salt thereof, or the compound of formula (16a) is a compound of formula (16a2):

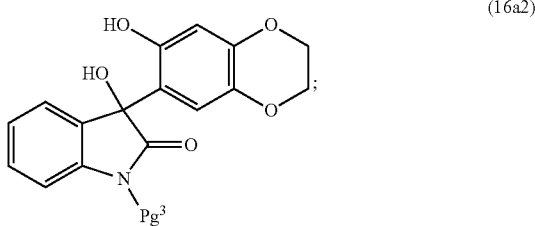

where Pg³ is a nitrogen protecting group, as a racemic mixture of enantiomers or as a non-racemic mixture of enantiomers, or a pharmaceutically acceptable salt thereof.

The method described above for treating a compound of formula (16) with a compound of formula (7) under suitable protecting conditions to provide a compound of formula (17), as described above, may further comprise a Grignard addition step prior to treating a compound of formula (16), as described above, wherein the Grignard addition step comprises first treating a compound of formula (4):

where r and R³ are each as described above in the Summary of the Invention for the compound of formula (I), with a Grignard reagent of formula (5):

where X is iodo, bromo or chloro, preferably bromo or chloro, and R is alkyl, under suitable conditions to form an intermediate Grignard addition product; and then treating a compound of formula (15):

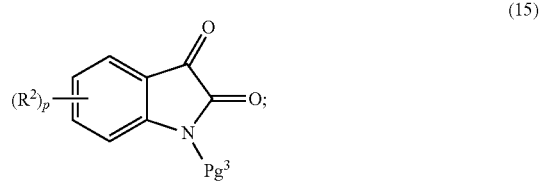

where p and R² are each as described above in the Summary of the Invention for the compound of formula (I), and Pg³ is a nitrogen protecting group, or a pharmaceutically acceptable salt thereof, with the intermediate Grignard addition product formed in substep a) above under suitable Grignard reaction conditions to provide a compound of formula (16), as described above. Preferably, the compound of formula (15) is a compound of formula (15a):

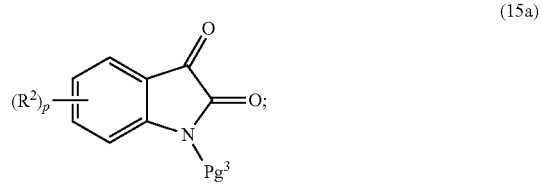

where p and R² are each as described above in the Summary of the Invention for the compound of formula (I) and Pg³ is a nitrogen protecting group, or a pharmaceutically acceptable salt thereof. Preferably, the compound of formula (4) is a compound of formula (4a):

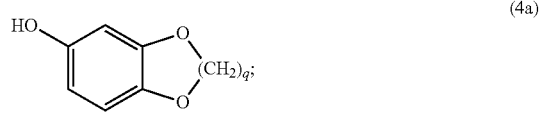

where q is 1 or 2. More preferably, the compound of formula (4a) is a compound of formula (4a1):

or the compound of formula (4a) is a compound of formula (4a2):

The method described above for first treating a compound of formula (4) with a Grignard reagent of formula (5) to form an intermediate Grignard addition product and then treating a compound of formula (15) with the intermediate Grignard addition product to provide a compound of formula (16), as described above, may further comprise a protecting step prior to treating the compound of formula (4) or the compound of formula (15), as described above, wherein the protecting step comprises treating a compound of formula (1):

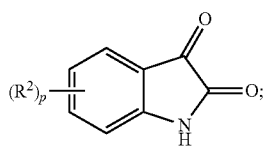
(1)

where p and R² are each as described above in the Summary of the Invention for the compound of formula (I), or a pharmaceutically acceptable salt thereof, with a compound of formula (14):

X-Pg³ (14);

where X is halo, typically iodo, bromo or chloro, preferably bromo or chloro, and Pg³ is a nitrogen protecting group, under suitable nitrogen protecting conditions to provide a compound of formula (15), as described above. Preferably, the compound of formula (1) is a compound of formula (1a):

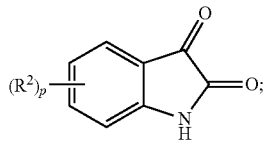
(1a)

where p and R² are each as described above in the Summary of the Invention for the compound of formula (I), or a pharmaceutically acceptable salt thereof.

Another preferred method of preparing a compound of formula (I), as described above in the Summary of the Invention, comprises the following steps:

(a) treating a compound of formula (I):

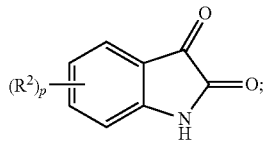
(1)

where p and R² are each as defined above for the compound of formula (I), or a pharmaceutically acceptable salt thereof, with a compound of formula (14):

X-Pg³ (14);

where X is halo, typically iodo, bromo or chloro, preferably bromo or chloro, and Pg³ is a nitrogen protecting group, under suitable nitrogen protecting conditions to provide a compound of formula (15):

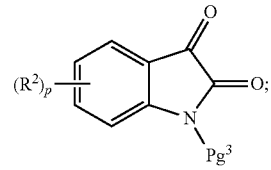
(15)

where p and R² are each as described above for the compound of formula (I), and Pg³ is a nitrogen protecting group, or a pharmaceutically acceptable salt thereof;

(b) treating a compound of formula (15) under suitable Grignard reaction conditions with an intermediate Grignard addition product formed from the treatment of a compound of formula (4):

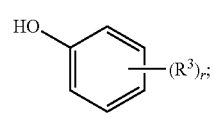
(4)

where r and R³ are each as defined above for the compound of formula (I), with a Grignard reagent of formula (5):

RMgX (5);

where R is alkyl and X is iodo, bromo or chloro, preferably bromo or chloro, under suitable conditions to provide a compound of formula (16):

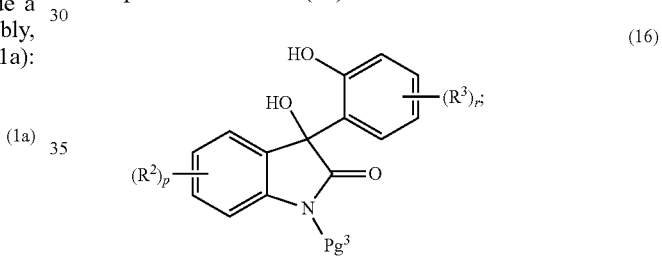
(16)

where p, r, R² and R³ are each as described above for the compound of formula (I) and Pg³ is a nitrogen protecting group, as a racemic mixture of enantiomers or as a non-racemic mixture of enantiomers, or a pharmaceutically acceptable salt thereof;

(c) treating a compound of formula (16) with a compound of formula (7):

Pg¹X (7);

where X is halo, typically iodo, bromo or chloro, preferably bromo or chloro, and Pg¹ is an oxygen protecting group under suitable protecting conditions to provide a compound of formula (17):

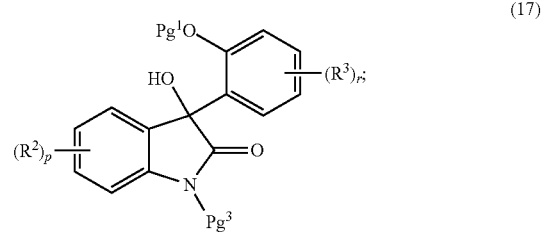
(17)

where p, r, R² and R³ are each as described above for the compound of formula (I), Pg¹ is an oxygen protecting group and Pg³ is a nitrogen protecting group, as a racemic mixture of enantiomers or as a non-racemic mixture of enantiomers, or a pharmaceutically acceptable salt thereof;

(d) treating a compound of formula (17) under suitable dehydroxylation conditions to provide a compound of formula (18):

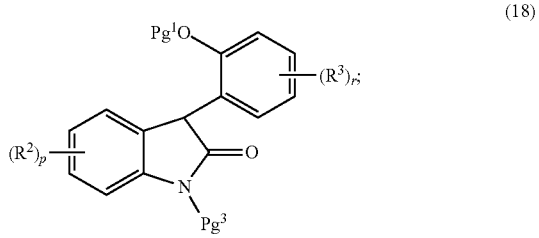
(18)

where p, r, R² and R³ are each as described above for the compound of formula (I), Pg¹ is an oxygen protecting group and Pg³ is a nitrogen protecting group, as a racemic mixture of enantiomers or as a non-racemic mixture of enantiomers, or a pharmaceutically acceptable salt thereof;

(e) treating a compound of formula (18) with a compound of formula (10):

Pg²OCH₂X   (10);

where Pg² is an oxygen protecting group and X is halo, typically iodo, bromo or chloro, preferably bromo or chloro, under suitable C-alkylation conditions comprising the presence of a phase transfer catalyst to provide a compound of formula (19):

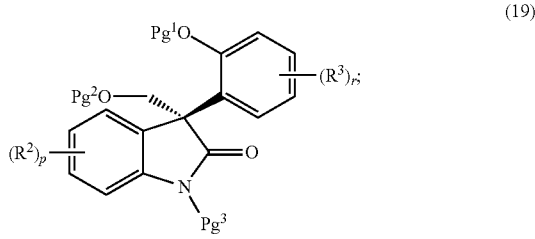
(19)

where p, r, R² and R³ are each as described above for the compound of formula (I), Pg¹ and Pg² are each independently an oxygen protecting group and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(f) treating a compound of formula (19) under suitable deprotection conditions to provide a compound of formula (20):

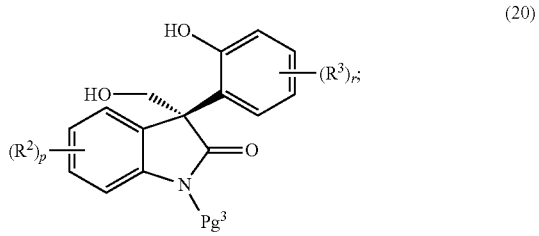
(20)

where p, r, R² and R³ are each as described above for the compound of formula (I), and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(g) treating a compound of formula (20) under suitable Mitsunobu reaction conditions to provide the compound of formula (21):

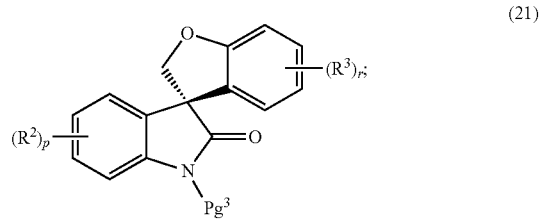
(21)

where p, r, R² and R³ are each as described above for the compound of formula (I), and Pg³ is a nitrogen protecting group, as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof;

(h) treating a compound of formula (21) under suitable nitrogen deprotecting conditions to provide a compound of formula (22):

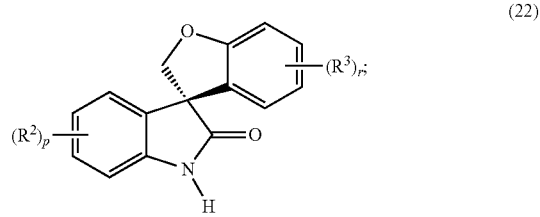
(22)

where p, r, R² and R³ are each as described above for the compound of formula (I), as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof; and (i) treating a compound of formula (22) with a compound of formula (2):

X—R¹   (2);

where X is halo, typically iodo, bromo or chloro, preferably bromo or chloro, and R¹ is as described above for the compound of formula (I), or a pharmaceutically acceptable salt thereof, under suitable N-alkylation conditions to provide a compound of formula (I), as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Another aspect of the invention, as described above in the Summary of the Invention, provides intermediates useful in the methods described herein.

One intermediate is a compound of formula (11):

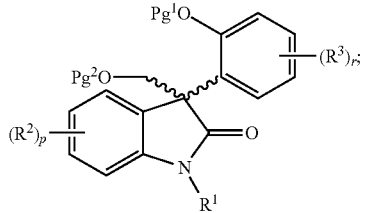
(11)

wherein $Pg^1$ and $Pg^2$ are each independently an oxygen protecting group and p, r, $R^1$, $R^2$ and $R^3$ are each as described above in the Summary of the Invention for the compounds of formula (I). Preferably, the compound of formula (11) is a compound of formula (11a):

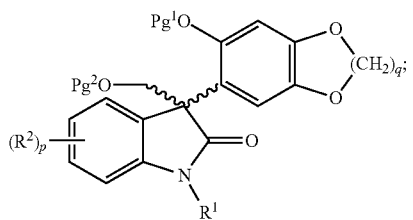
(11a)

where q is 1 or 2, p, $R^1$ and $R^2$ are each as defined above for the compounds of formula (11) and $Pg^1$ and $Pg^2$ are each independently an oxygen protecting group, as a racemic mixture of enantiomers or as a non-racemic mixture of enantiomers, or a pharmaceutically acceptable salt thereof. Preferably, the compound of formula (11a) is a compound of formula (11a1):

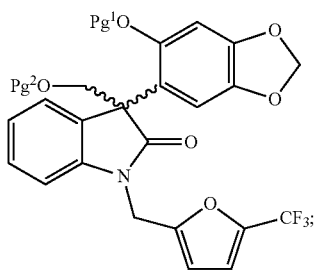
(11a1)

where $Pg^1$ and $Pg^2$ are each independently an oxygen protecting group, as a racemic mixture of enantiomers or as a non-racemic mixture of enantiomers, or a pharmaceutically acceptable salt thereof.

Other intermediates are a compound of formula (12) or a compound of formula (13):

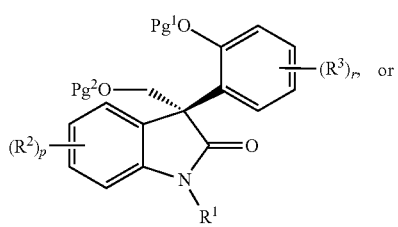
(12)

or

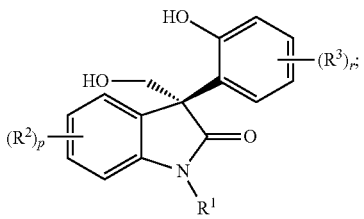
(13)

wherein each $Pg^1$ and $Pg^2$ is independently an oxygen protecting group, and each p, r, $R^1$, $R^2$ and $R^3$ are as defined above in the Summary of the Invention for compounds of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. Preferably, the compound of formula (12) is a compound of formula (12a):

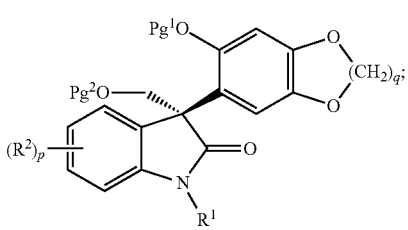
(12a)

where q is 1 or 2, $Pg^1$ and $Pg^2$ are each independently an oxygen protecting group and p, $R^1$ and $R^2$ are each as defined above for compounds of formula (12), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (12a) is a compound of formula (12a1):

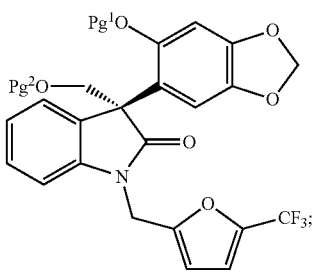
(12a1)

where $Pg^1$ and $Pg^2$ are each independently an oxygen protecting group, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. Preferably, the compound of formula (13) is a compound of formula (13a):

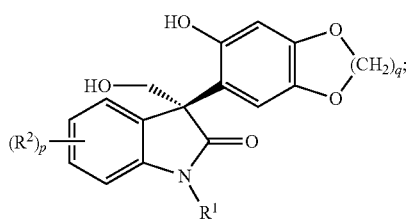
(13a)

where q is 1 or 2 and p, $R^1$ and $R^2$ are each as defined above for compounds of formula (13), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. More preferably, the compound of formula (13a) is a compound of formula (13a1):

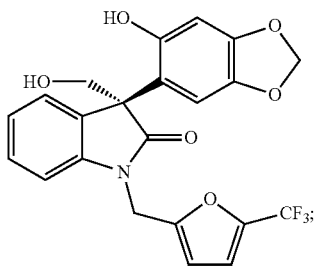
(13a1)

as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Other intermediates useful in the method of the invention are a compound of formula (19), a compound of formula (20), a compound of formula (21) or a compound of formula (22):

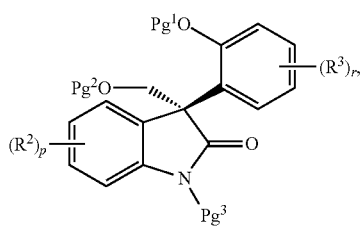
(19)

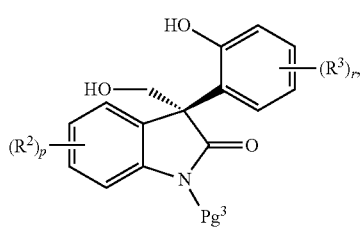
(20)

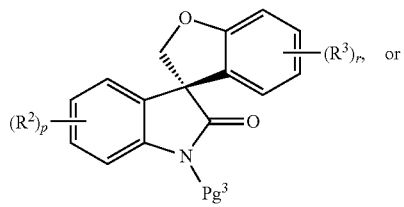
(21)

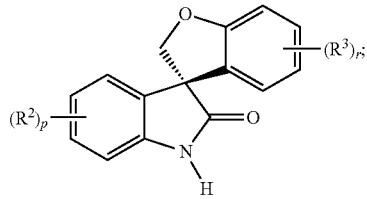
(22)

wherein each $Pg^1$ and $Pg^2$ is independently an oxygen protecting group, each $Pg^3$ is a nitrogen protecting group, and each p, r, $R^2$ and $R^3$ is as described above in the Summary of the Invention for compounds of formula (I), as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof. Preferably, the compound of formula (19), the compound of formula (20), the compound of formula (21) and the compound of formula (22) are compounds of formula (19a), formula (20a), formula (21a) and formula (22a), respectively:

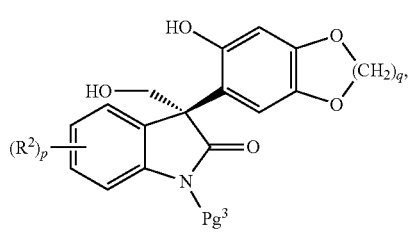
(19a)

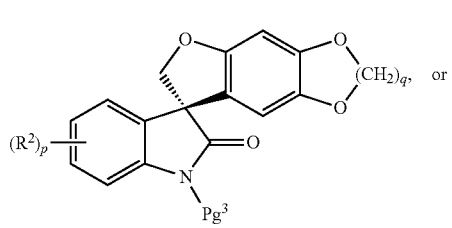
(20a)

(21a)

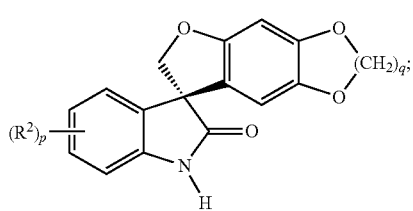
(22a)

where each q is independently 1 or 2, each Pg[1] and each Pg[2] is independently an oxygen protecting group, each Pg[3] is a nitrogen protecting group, and each p, each R[2] and each R[3] is as defined above in claim 80, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Preferably, the compound of formula (19a) is a compound of formula (19a1) or of formula (19a2):

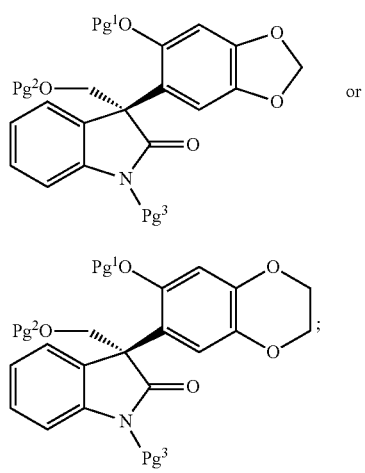
(19a1)

(19a2)

wherein each Pg[1] and each Pg[2] is independently an oxygen protecting group and each Pg[3] is a nitrogen protecting group, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Preferably, the compound of formula (20a) is a compound of formula (20a1) or formula (20a2):

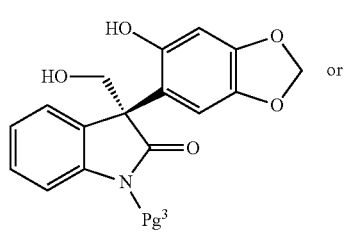
(20a1)

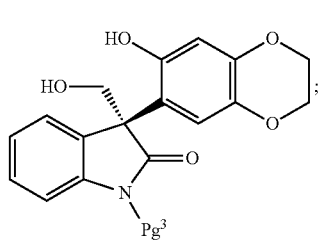
(20a2)

wherein each Pg[3] is independently a nitrogen protecting group, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Preferably, the compound of formula (21a) is a compound of formula (21a1) or of formula (21a2):

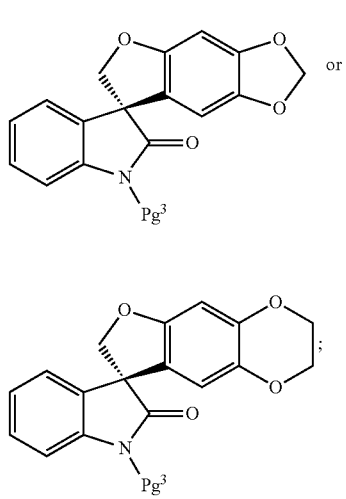
(21a1)

(21a2)

wherein each Pg[3] is independently a nitrogen protecting group, as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Preferably, the compound of formula (22a) is a compound of formula (22a1) or of formula (22a2):

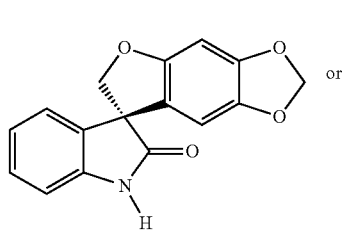
(22a1)

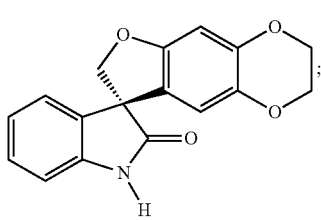

(22a2)

as an isolated (S)-enantiomer or a non-racemic mixture of enantiomers having an enantiomeric excess of the (S)-enantiomer of greater than 80%, preferably greater than 90%, more preferably greater than 95%, most preferably greater than 99%, or a pharmaceutically acceptable salt thereof.

Specific embodiments of the methods of the invention, including the suitable conditions for each of the above described steps, are described in more detail below in the Methods of the Invention.

METHODS OF THE INVENTION

The methods of the invention are directed to asymmetric syntheses of a compound of formula (I), as set forth above in the Summary of the Invention, as an isolated (S)-enantiomer, or a non-racemic mixture of the (S)-enantiomer and the (R)-enantiomer having an enantiomeric excess of the (S)-enantiomer greater than 80%, preferably greater than 90%, more preferably greater than 95% and most preferably greater than 99%.

It is understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *Advanced Organic Chemistry Reactions, Mechanisms, and Structure*, 5th edition (Wiley, December 2000)) or prepared as described herein or in PCT Published Patent Application No. WO 2006/110917, PCT Published Patent Application No. WO 2010/45251, PCT Published Patent Application No. WO 2010/045197, PCT Published Patent Application No. WO 2011/047174 and PCT Published Patent Application No. WO 2011/002708.

It is also understood that in the following description, combinations of substituents and/or variables of the depicted formulae are permissible only if such contributions result in stable compounds.

"Suitable Mitsunobu reaction conditions" as used herein generally refers to reaction conditions which allow for the formation of a C—O bond by the condensation of an acidic component with an alcohol (either primary secondary or benzyl alcohol) in the presence of triphenylphosphine or another suitable phosphine and an azodicarboxylic acid derivative, such as, but not limited to, diethyl azodicarboxylate (DEAD), diisopropyl azodicarboxylate (DIAD) or dibenzyl azodicarboxylate (DBAD). "Suitable Mitsunobu reaction conditions" are further described herein in the description of Reaction Scheme 1 and Reaction Scheme 2 and are further described in Hughes, D. L., *Org. Prep.* (1996), 28, 127-164 and Kumara Swamy, K. C., et al., "Mitsunobu and Related Reactions Advances and Applications", *Chem. Rev.* (2009), 109, 2551-2651.

"Suitable deprotection conditions" as used herein generally refers to reaction conditions which allow for the simple cleavage of protecting groups. For example, the cleavage of a benzyl protecting group is normally performed by catalytic hydrogenation and can be performed with good selectivity under mild conditions using a heterogeneous palladium on carbon (Pd/C) catalyst in the presence of hydrogen gas or a hydrogen transfer agent (e.g., ammonium formate or isopropanol). Efficient removal of protecting groups depends on selection of the most active and selective catalyst and an optimized set of reaction conditions. "Suitable deprotection conditions" are further described herein in the description of Reaction Scheme 1 and Reaction Scheme 2 and are further described in detail in Greene, T. W. and Wuts, P. G. M. *Greene's Protective Groups in Organic Synthesis* (2006), 4$^{th}$ Ed. Wiley.

"Suitable recrystallization conditions" as used herein generally refers to reaction conditions which allow for the crystallization process of forming a solid (i.e., a crystal) from a solution. "Suitable recrystallization conditions" also refers to reaction conditions which allow for the separation of a chemical solid-liquid whereby a mass transfer of a solute from the liquid solution to a pure solid crystalline phase occurs. Suitable crystals are obtained through a variation of the solubility conditions of the solute in the solvent, including, but not limited, to ethanol, ethyl acetate, tetrahydrofuran or diethyl ether. Mixtures of solvents can also be used in which the solute is dissolved in a solvent in which there is high solubility followed by the addition of an anti-solvent in which the solute is less soluble but impurities are soluble, leading to the formation of a pure crystalline solid phase. Crystallization may also be induced by the addition of seed crystals of previously crystallized material to a solution containing the same solute. These seed crystals serve as nucleation sites upon which further crystallization takes place, speeding up the process of forming a pure solid crystalline phase. "Suitable recrystallization conditions" are further described herein in the description of Reaction Scheme 1 and Reaction Scheme 2 and are described in further detail in Mersmann, A., *Crystallization Technology Handbook* (2001), CRC; 2nd ed.

"Suitable C-alkylation conditions" as used herein generally refers to reaction conditions which allow for the transfer of an optionally substituted alkyl from one molecule to another to form a carbon-carbon bond. For example, an intermediate in the Reaction Schemes illustrated below may be treated with an alkylating agent, such as, but not limited to, benzyl halide, in the presence of a base, such as, but not limited to, sodium methoxide, to yield a product wherein a carbon-carbon bond is formed. C-alkylation reactions can be carried out under phase-transfer conditions in which one or more substrates are dissolved in a solvent in which the base is not soluble, typically an organic solvent such as, but not limited to, toluene, ethyl acetate, dioxane, or diethyl ether is used with an inorganic base such as, but not limited to, lithium hydroxide, sodium hydroxide, potassium hydroxide, potassium phosphate, sodium bicarbonate, cesium carbonate, or potassium carbonate. The base can be used as a solid or be dissolved in water to form an insoluble aqueous solution. A phase-transfer catalyst is used to transfer the base from the insoluble phase to the soluble organic phase where it can react with the substrate and effect a C-alkylation. Phase-transfer catalysts are often large organic cations that have partial solubility in organic and aqueous solvents such as, but not limited to, tetraalkylammonium halides and tetraalkylphosphonium halides. "Suitable C-alkylation conditions" are further described herein in the description of Reaction Scheme 1 and Reaction Scheme 2 and are described in further detail in Smith, M. B. and J. March,

*Advanced Organic Chemistry: Reactions, Mechanisms, and Structure,* 5th edition (Wiley, December 2000).

"Suitable dehydroxylation conditions" as used herein generally refers to reaction conditions which allow for the dehydration of an alcohol in the presence of a strong acid, such as, but not limited to, trifluoroacetic acid or sulphuric acid. "Suitable dehydroxylation conditions" are further described herein in the description of Reaction Scheme 1 and Reaction Scheme 2 and are described in further detail in Smith, M. B. and J. March, *Advanced Organic Chemistry: Reactions, Mechanisms, and Structure,* 5th edition (Wiley, December 2000).

"Suitable N-alkylation conditions" as used herein generally refers to reaction conditions which allow for the alkylation of the relevant nitrogen and is usually reductive amination in the presence of a reducing agent, such as, but not limited to, sodium borohydride, and an aldehyde or alkylation using a base, such as, but not limited to, potassium carbonate, and an alkylating agent, such as, but not limited to, a benzyl halide. "Suitable N-alkylation conditions" are further described herein in the description of Reaction Scheme 1 and Reaction Scheme 2 and are described in further detail in Greene, T. W. and P. G. M. Wuts, *Greene's Protective Groups in Organic Synthesis* (2006), 4$^{th}$ Ed., Wiley.

"Suitable Grignard addition conditions" as used herein generally refers to reaction conditions which allow for the addition of an organomagnesium halide (i.e., Grignard reagent) to a ketone or aldehyde to form a tertiary or secondary alcohol, respectively. "Suitable Grignard addition conditions" are further described herein in the description of Reaction Scheme 1 and Reaction Scheme 2 and are described in detail in Smith, M. B. and J. March, *Advanced Organic Chemistry: Reactions, Mechanisms, and Structure,* 5th edition (Wiley, December 2000); Garst, J. F. and Ungvary, F., "Mechanism of Grignard reagent formation"; and *Grignard Reagents*; Richey, R. S., Ed.; John Wiley & Sons: New York, 2000; pp 185-275.

It will be appreciated by those skilled in the art that in the process described below the functional groups of intermediate compounds may need to be protected by suitable protecting groups. Such functional groups include hydroxy, amino, mercapto and carboxylic acid. Suitable protecting groups for an oxygen atom ("oxygen protecting groups") include, but are not limited to, trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for a nitrogen atom ("nitrogen protecting groups") include, but are not limited to, benzhydryl (diphenylmethyl), t-butoxycarbonyl, benzyloxycarbonyl, and the like. Suitable protecting groups for a sulfur atom ("sulfur protecting groups") include —C(O)—R (where R is alkyl, aryl or aralkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

"Oxygen protecting groups", "nitrogen protecting groups", "suitable protecting conditions" and "suitable deprotection conditions" as used herein are further described herein in the description of Reaction Scheme 1 and Reaction Scheme 2 and are described in further detail in Greene, T. W. and P. G. M. Wuts, *Greene's Protective Groups in Organic Synthesis* (2006), 4$^{th}$ Ed., Wiley.

The advantages of the asymmetric syntheses of the compounds of formula (I) as described herein over the syntheses disclosed in PCT Published Patent Application No. WO 2006/110917, PCT Published Patent Application No. WO 2010/045251, PCT Published Patent Application No. WO 2010/045197, PCT Published Patent Application No. WO 2011/047174 and PCT Published Patent Application No. WO 2011/002708 are as follows:

1. The asymmetric syntheses disclosed herein do not require simulated moving bed (SMB) chromatography technology for resolving the enantiomers of a racemic mixture of a compound of formula (I), thereby eliminating a costly step.
2. Chirality is introduced in the compound at an earlier step, thereby eliminating undesirable intermediates and final products.
3. Overall yield of the compound of formula (I) is higher for the asymmetric syntheses than for the published processes.
4. Overall cost for the synthesis of the compound of formula (I) is lower than for the published processes due to the reduction of the amount of solvents required.

A. Asymmetric Synthesis of Compounds of Formula (I), Formula (Ia), and Formula (Ia1) by Method A Compounds of formula (I), as described above in the Summary of the Invention, can be prepared by "Method A", as described below in Reaction Scheme 1 where p, r, $R^1$, each $R^2$ and each $R^3$ are as described above in the Summary of the Invention for compounds of formula (I), R is alkyl, each X is independently halo, typically iodo, bromo or chloro, preferably bromo or chloro, except for the Grignard reagent of formula (5) wherein X is iodo, bromo or chloro, preferably bromo or chloro, and $Pg^1$ and $Pg^2$ are each independently an oxygen protecting group, such as benzyl, alkyl, tert-butyldiphenylsilyl or triphenylsilyl:

REACTION SCHEME 1

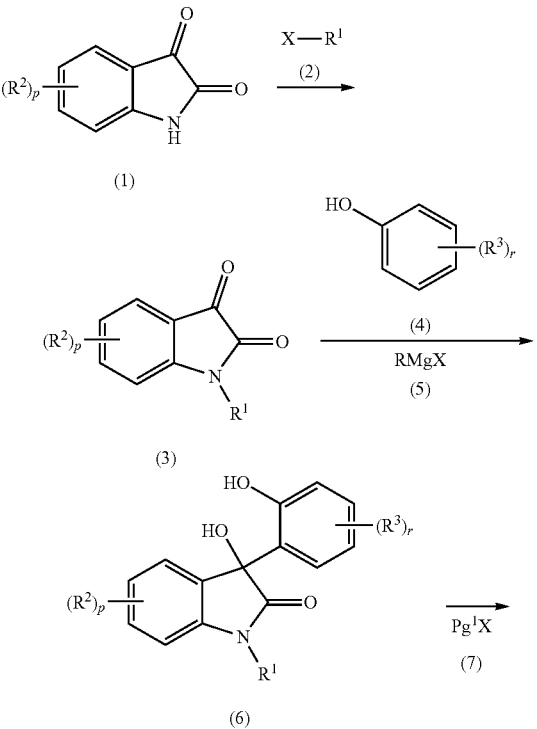

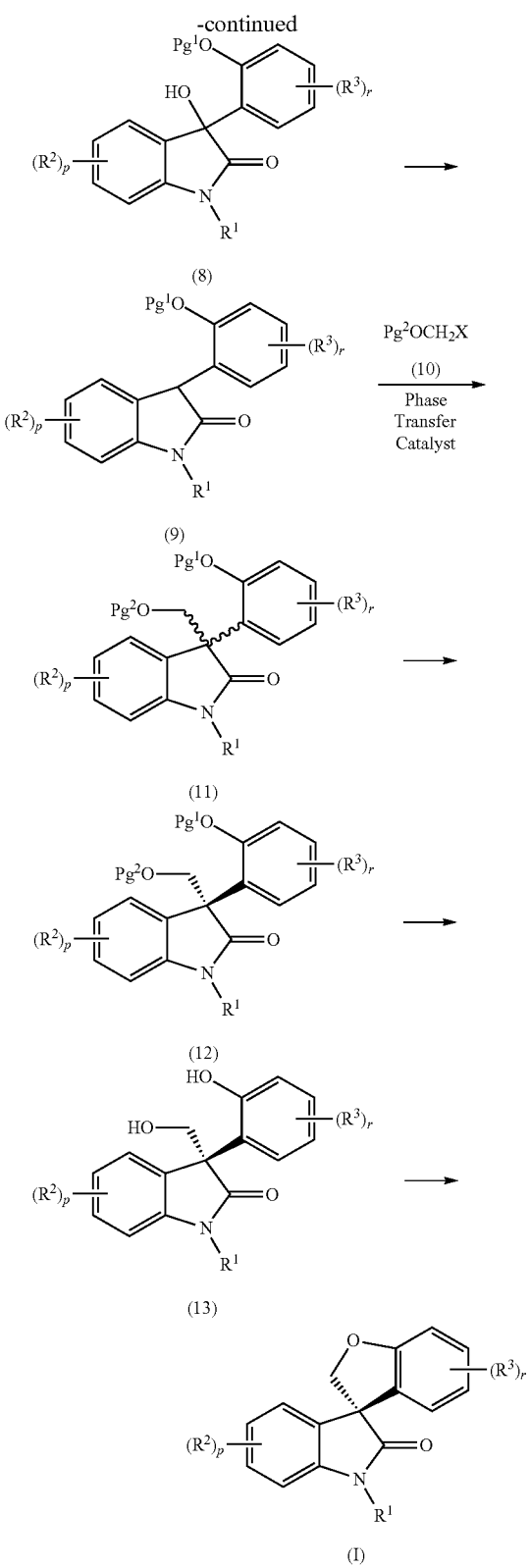

2010/045197, PCT Published Patent Application No. WO 2011/047174 and PCT Published Patent Application No. WO 2011/002708.

In general, compounds of formula (I) are prepared according to Method A, as described above in Reaction Scheme 1, by first treating a compound of formula (1), or a pharmaceutically acceptable salt thereof, with an excess molar amount of a compound of formula (2) under suitable N-alkylation conditions, for example, in a polar aprotic solvent, such as acetonitrile, dimethylformamide, tetrahydrofuran, dioxane or dimethoxyethane, in the presence of a base, such as cesium carbonate, anhydrous potassium carbonate, sodium hydride, or calcium hydride, at a temperature of between about 15° C. and about 30° C. and with stirring for a period of time of between about 1 hour and about 16 hours. The resulting compound of formula (3) is isolated from the reaction mixture by standard isolation techniques, such as filtration.

The compound of formula (3) so formed is then treated with a slightly excess molar amount of an intermediate Grignard addition product prepared by treating a compound of formula (4) in an polar aprotic solvent, such as tetrahydrofuran, dioxane, dimethoxyethane, diethyl ether, tert-butyl methyl ether, or dichloromethane, with a slightly excess molar amount of a Grignard reagent of formula (5) in a polar aprotic solvent, such as tetrahydrofuran, diethyl ether, or dioxane under suitable Grignard reaction conditions, such as at a temperature of between about 0° C. and about 25° C., to provide a compound of formula (6), which is isolated from the reaction mixture by standard isolation techniques, such as extraction, filtrate and concentration.

The compound of formula (6) in an polar aprotic solvent, such as dimethylformamide, acetonitrile, or tetrahydrofuran in the presence of a base, such as cesium carbonate or potassium carbonate, is then treated with a slightly excess molar amount of a compound of formula (7) where $Pg^1$ is an oxygen protecting group, preferably benzyl, under suitable oxygen protecting conditions (i.e., the protecting step), such as at a temperature of between about 0° C. and about 5° C. for a period of time of between about 15 minutes and about 1 hour, followed by warming to ambient temperature and stirring for a period of time of between about 1 hour to about 24 hours. The resulting compound of formula (8) is isolated from the reaction mixture by standard techniques, such as precipitation and filtration.

The removal of the hydroxyl group at the C3 position of the oxindole ring (i.e., the dehydroxylation step) in the compound of formula (8) is achieved by treating the compound of formula (8) in a polar aprotic solvent, such as dichloromethane, or without any solvent under suitable conditions, such as treatment with a silane reagent, such as triethylsilane or triphenylsilane in the presence of an acid, such as, but not limited to, trifluoroacetic acid, to yield the compound of formula (9), which is isolated from the reaction mixture by standard isolation techniques, such as concentration and extraction.

The compound of formula (11) is prepared by asymmetric phase transfer-catalyzed C-alkylation wherein a mixture of less than equimolar amount, preferably less than 20%, of a phase transfer catalyst, such as a quaternary ammonium salt of quinidine or cinchonine, preferably a quaternary ammonium salt of cinchonine, and excess base, such as potassium hydroxide, sodium hydroxide, lithium hydroxide or cesium hydroxide, preferably potassium hydroxide, in a non-polar solvent, such as toluene, is cooled to a temperature of between about −20° C. and about 25° C. To this mixture is added a solution of a compound of formula (9) and an excess Compounds of formula (1), (2), (4), (5), (7) and (10) are commercially available, or can be prepared according to methods known to one skilled in the art or by the methods disclosed in PCT Published Patent Application No. WO 2006/110917, PCT Published Patent Application No. WO 2010/45251, PCT Published Patent Application No. WO molar amount of a compound of formula (10) where $Pg^2$ is an oxygen protecting group, preferably benzyl, over a period of time of between about 5 minutes to about 2 hours with stirring. The compound of formula (11) is isolated from the reaction mixture by standard isolation conditions, such as extraction, followed by acid wash, concentration, and filtration as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%.

A quaternary ammonium salt of cinchonine can be prepared by refluxing a suspension of cinchonine and a suitable alkyl halide, such as, but not limited to, 9-chloromethylanthracene or 1-bromomethylnaphthalene, in a suitable solvent, such as, but not limited to, anhydrous toluene, tetrahydrofuran. The product is isolated by means of crystallization using suitable solvent, such as, but not limited to, diethyl ether or methanol (E. J. Corey and M. C. Noe, Org. Synth. 2003; 80:38-45).

The compound of formula (11) is then dissolved in a protic solvent, such as ethanol, at reflux temperatures, and allowed to cool to ambient temperature. A seed crystal of the racemic compound of formula (11) is then added to the cooled solution. Crystallization of the solution afforded the compound of formula (12) as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%.

The compound of formula (12) is then deprotected under suitable deprotection (reduction) conditions, such as treating a mixture of the compound of formula (12), 10% palladium on carbon and a weak acid, such as acetic acid, formic acid or trifluoroacetic acid in a protic/polar aprotic solvent mixture, such as a mixture of a lower alkanol in tetrahydrofuran, ethyl acetate, or dioxane, preferably a 1:1 mixture of ethanol and tetrahydrofuran, in the presence of a silane reagent, such as triethylsilane, in an aprotic polar solvent, such as tetrahydrofuran or ethanol, at ambient temperature. The resulting compound of formula (13) as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%, is isolated from the reaction mixture by standard isolation techniques, such as filtration and concentration.

Intramolecular cyclization of a compound of formula (13) to provide a compound of formula (I) is achieved by treating a compound of formula (13) to suitable Mitsunobu reaction conditions, such as the employment of a phosphine reagent, preferably, but not limited to, triphenylphosphine, tributylphosphine, 2-(diphenylphosphino)pyridine, 4-(diphenylphosphino)dimethylaniline and 4-(N,N-dimethylamino)phenyldiphenylphosphine, and an azodicarboxylate ester, such as, but not limited to, diethylazodicarboxylate, diisopropylazodicarboxylate, di-tert-butylazodicarboxylate or tetramethyldiazenedicarboxamide, in a polar aprotic solvent, preferably, but not limited to, tetrahydrofuran, dichloromethane or ethyl acetate. The resulting compound of formula (I) is isolated from the reaction mixture by standard isolation techniques, such as extraction, filtration and concentration, as an isolated (S)-enantiomer, or a non-racemic mixture of enantiomers having an enantiomeric excess of the (S)-enantiomer of greater than 80% preferably greater than 90%, more preferably greater than 95%, most preferably greater than 99%.

The above described Method A is particularly efficient with respect to yield and enantiomeric excess of the desired product when the $R^1$ group does not participate in competing side reactions, such as reduction when the compound of formula (12) is deprotected to form the compound of formula (13).

A specific method of preparing the compounds of formula (I) as set forth above in Reaction Scheme 1 is illustrated below in Reaction Scheme 1A for the preparation of compounds of formula (Ia), where p, $R^1$ and $R^2$ are as defined above in the Summary of the Invention for the compounds of formula (I), q is 1 or 2, each X is independently halo, typically iodo, bromo or chloro, preferably bromo or chloro, except for the Grignard reagent of formula (5) wherein X is iodo, bromo or chloro, preferably bromo or chloro, and $Pg^1$ and $Pg^2$ are each independently an oxygen protecting group, such as hydrogen, benzyl, alkyl, methoxymethyl (MOM), benzyloxymethyl (BOM), tert-butyldimethylsilyl, tert-butyldiphenylsilyl, trimethylsilyl or triphenylsilyl.

REACTION SCHEME 1A

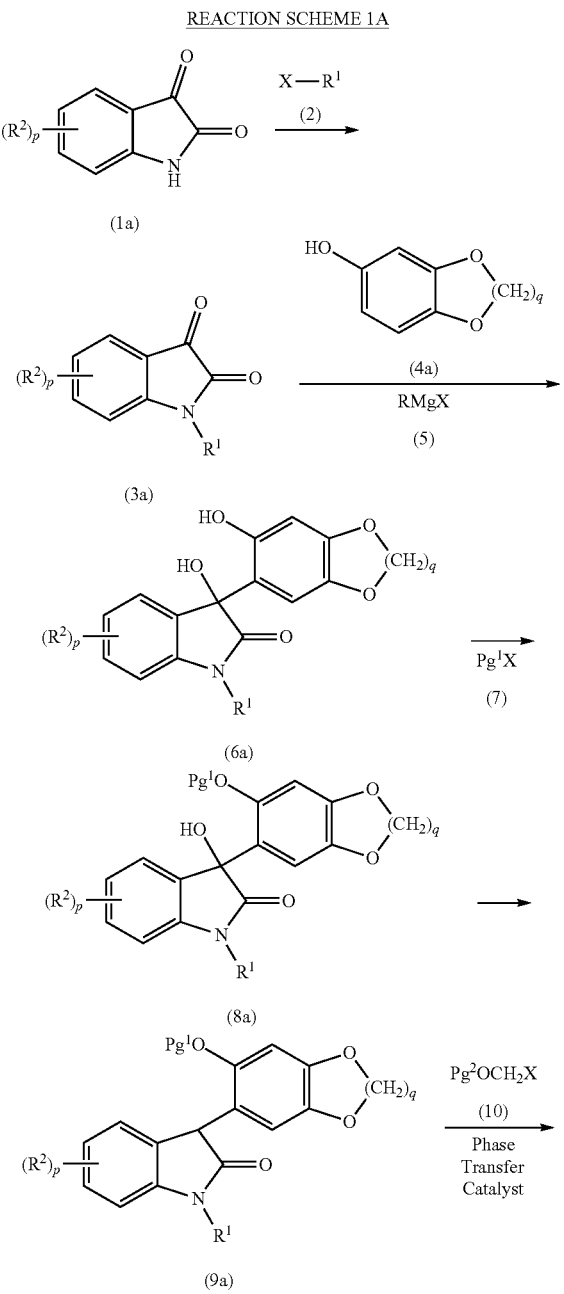

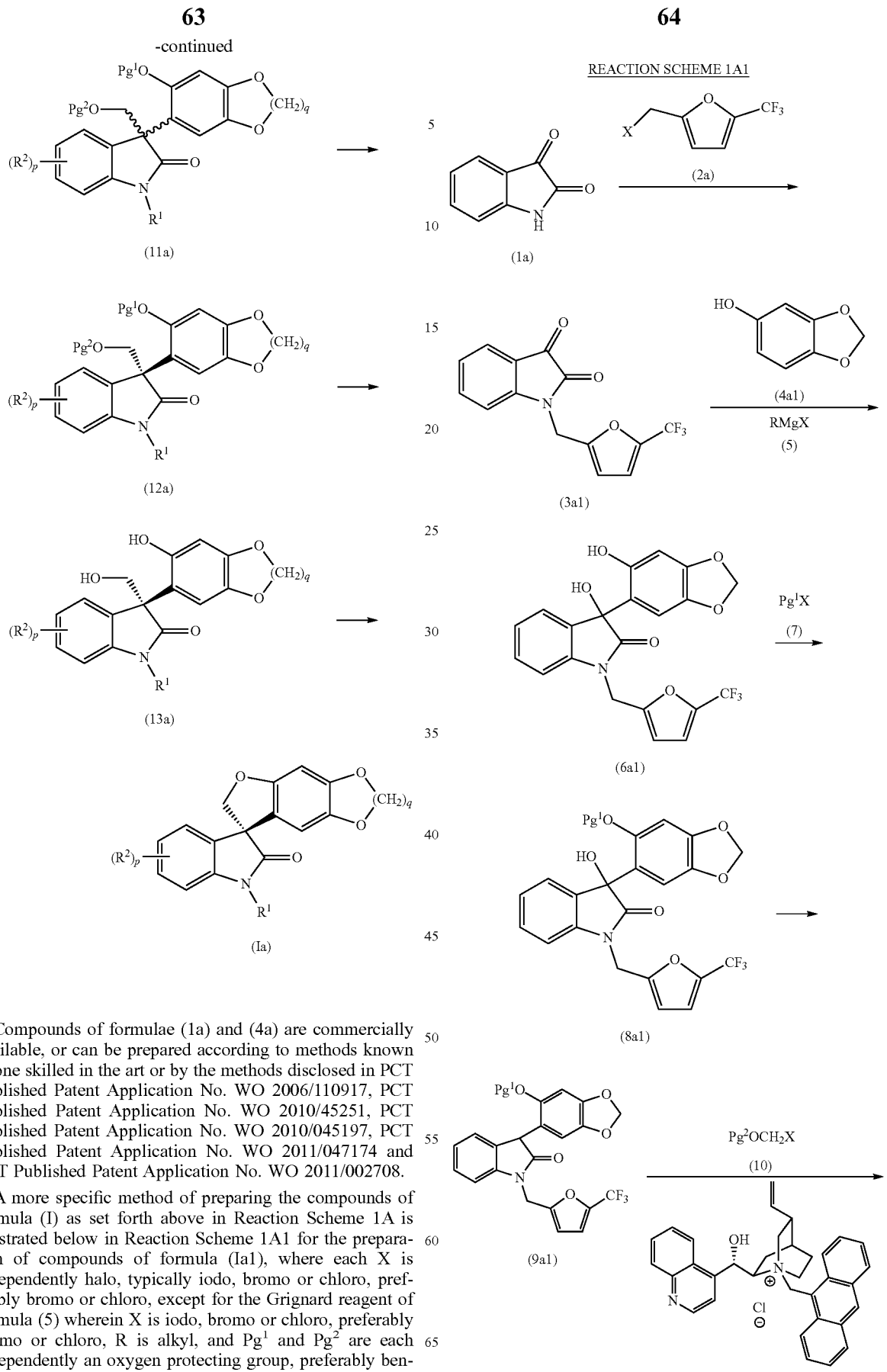

Compounds of formulae (1a) and (4a) are commercially available, or can be prepared according to methods known to one skilled in the art or by the methods disclosed in PCT Published Patent Application No. WO 2006/110917, PCT Published Patent Application No. WO 2010/45251, PCT Published Patent Application No. WO 2010/045197, PCT Published Patent Application No. WO 2011/047174 and PCT Published Patent Application No. WO 2011/002708.

A more specific method of preparing the compounds of formula (I) as set forth above in Reaction Scheme 1A is illustrated below in Reaction Scheme 1A1 for the preparation of compounds of formula (Ia1), where each X is independently halo, typically iodo, bromo or chloro, preferably bromo or chloro, except for the Grignard reagent of formula (5) wherein X is iodo, bromo or chloro, preferably bromo or chloro, R is alkyl, and $Pg^1$ and $Pg^2$ are each independently an oxygen protecting group, preferably benzyl:

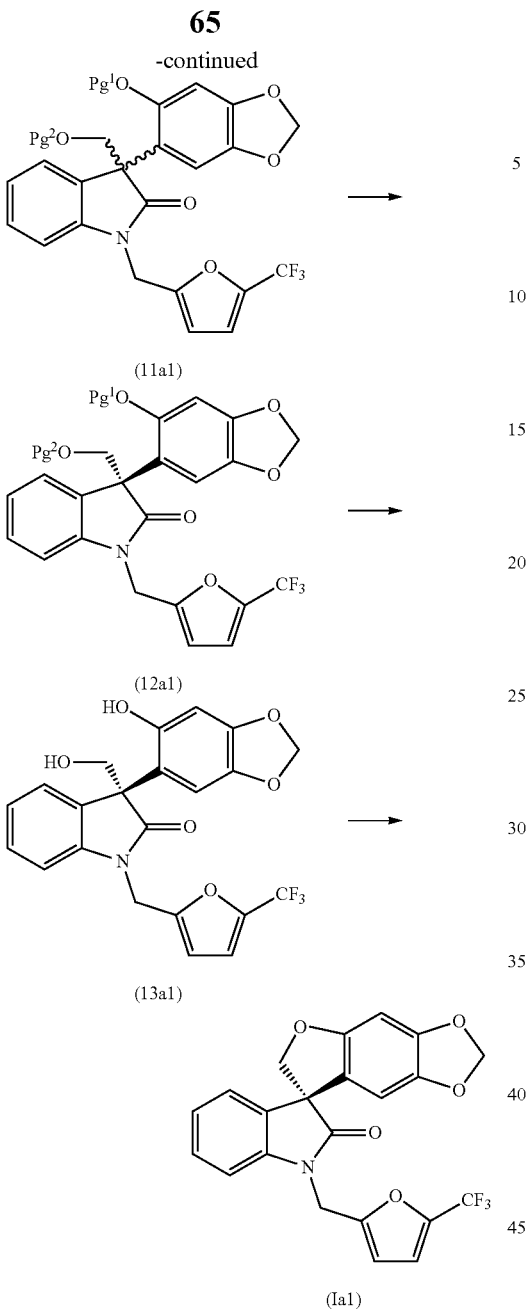

described below in Reaction Scheme 1 where p, r, R[1], each R[2] and each R[3] are as described above in the Summary of the Invention for compounds of formula (I), R is alkyl, each X is independently halo, typically iodo, bromo or chloro, preferably bromo or chloro, except for the Grignard reagent of formula (5) wherein X is iodo, bromo or chloro, preferably bromo or chloro, and Pg[1] and Pg[2] are each independently an oxygen protecting group, such as hydrogen, benzyl, alkyl, MOM, BOM, tert-butyldimethylsilyl, tert-butyldiphenylsilyl, trimethylsilyl or triphenylsilyl, and Pg[3] is a nitrogen protecting group, such as benzhydryl (diphenylmethyl) or benzyl, tert-butoxycarbonyl, para-methoxybenzyl, 2,4-dimethoxybenzyl:

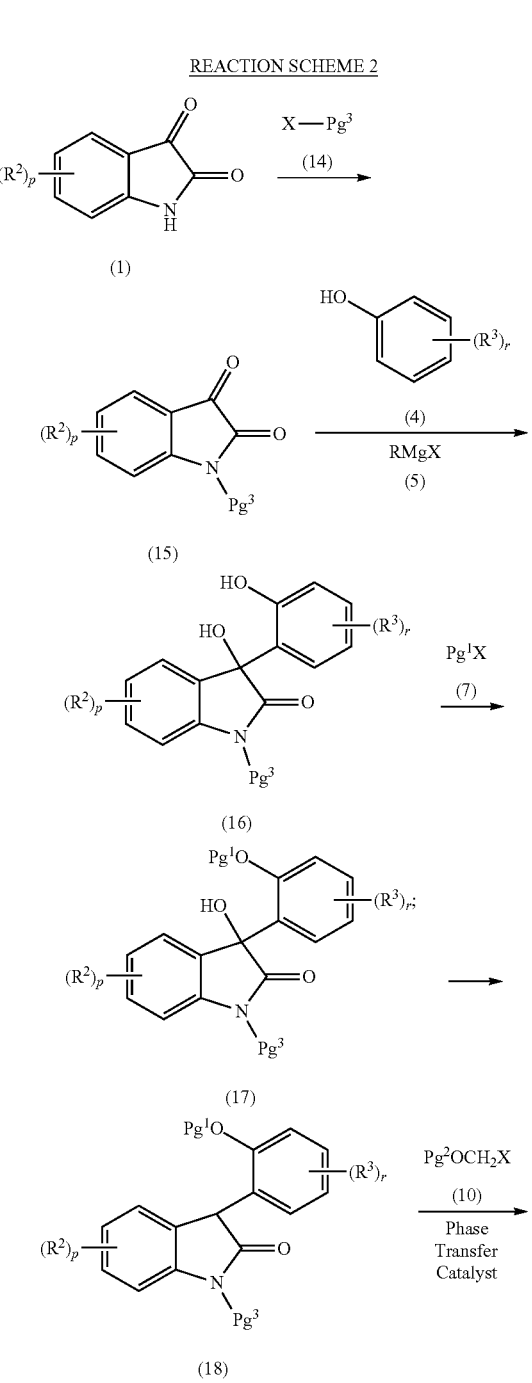

The compounds of formulae (2a) and (4a1) are commercially available, or can be prepared according to methods known to one skilled in the art or by the methods disclosed in PCT Published Patent Application No. WO 2006/110917, PCT Published Patent Application No. WO 2010/45251, PCT Published Patent Application No. WO 2010/045197, PCT Published Patent Application No. WO 2011/047174 and PCT Published Patent Application No. WO 2011/002708. The cinchonium phase transfer catalyst can be prepared according to methods known to one skilled in the art or by the methods disclosed herein.

The specific experimental conditions and parameters for the above Reaction Scheme 1A1 are described in more detail below in the Examples.

B. Asymmetric Synthesis of Compounds of Formula (I), Formula (Ia), and Formula (Ia2) by Method B Compounds of formula (I), as described above in the Summary of the Invention, can be prepared by Method B as

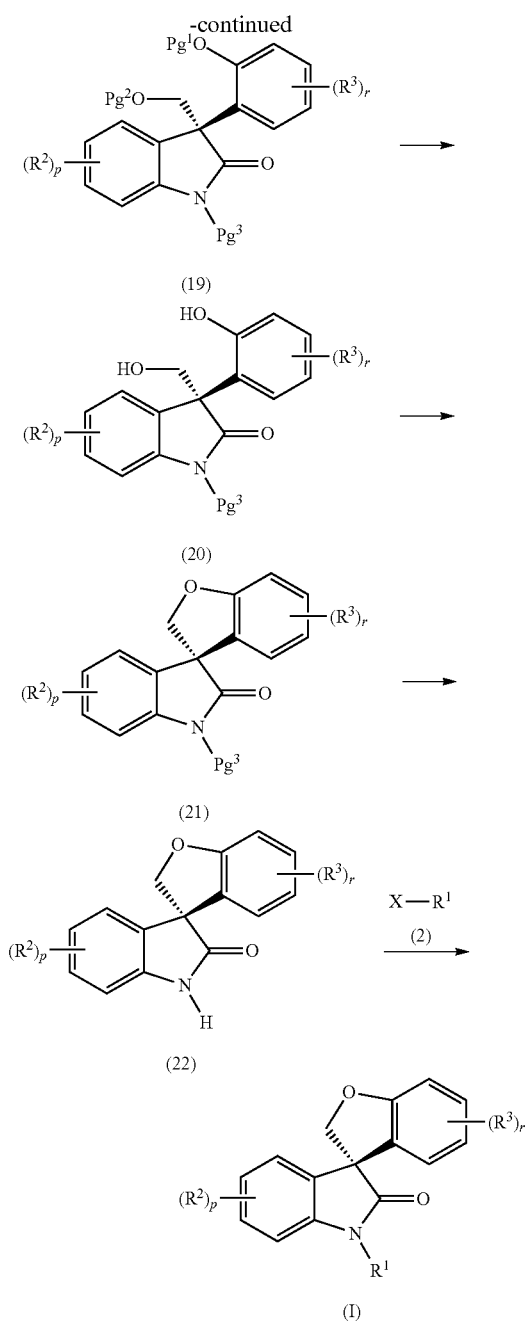

about 5° C. or preferably at between about 15° C. and 35° C., with an excess molar amount of a compound of formula (14) in a polar aprotic solvent, such as dimethyl formamide, at ambient temperature. The reaction mixture is heated to a temperature of between about ambient temperature and about 60° C. for a period of time of between about 2 hours and 16 hours. The reaction mixture is then cooled to a temperature of between about 0° C. and 5° C. and quenched with the addition of water. Alternatively, the cooled reaction mixture is used in the next step without quenching the reaction with water. The resulting compound of formula (15) is then isolated from the reaction mixture by standard isolation techniques, such as precipitation, filtration, water wash and evaporation of solvent.

The compound of formula (15) so formed is then treated with a slightly excess molar amount of an intermediate Grignard addition product prepared by treating a compound of formula (4) in an polar aprotic solvent, such as tetrahydrofuran or dioxane and dimethoxyethane, with a Grignard reagent of formula (5), such as isopropylmagnesium chloride, in a polar aprotic solvent, such as tetrahydrofuran, dioxane, or ether, under suitable Grignard reaction conditions, such as at a temperature of between about 0° C. and about 25° C., to provide a compound of formula (16), which is isolated from the reaction mixture by standard isolation techniques, such as extraction, filtrate and concentration.

The compound of formula (16) in an polar aprotic solvent, such as dimethylformamide or acetonitrile, in the presence of a base, such as cesium carbonate or potassium carbonate, is then treated with a slightly excess molar amount of a compound of formula (7) where $Pg^1$ is an oxygen protecting group, preferably benzyl, under suitable oxygen protecting conditions (i.e., the protecting step), such as ambient temperature for a period of time of between about 2 hours and about 16 hours or for a period of time of about 90 hours. The resulting compound of formula (17) is isolated from the reaction mixture by standard techniques, such as precipitation and filtration.

The removal of the hydroxyl group at the C3 position of the oxindole ring (i.e., the dehydroxylation step) in the compound of formula (17) is achieved by treating the compound of formula (17) in a polar aprotic solvent, such as dichloromethane, dichloroethane or without any solvent under suitable conditions, such as treatment with a silane reagent, such as triethylsilane or triphenylsilane, in the presence of an acid, such as, but not limited to, trifluoroacetic acid or acetic acid, to yield the compound of formula (18), which is isolated from the reaction mixture by standard isolation techniques, such as concentration and extraction.

The compound of formula (19) is prepared by asymmetric phase transfer-catalyzed C-alkylation wherein a mixture of a phase transfer catalyst in less than equimolar amount, preferably less than 20%, such as a quaternary ammonium salt of quinidine or cinchonine, preferably a quaternary ammonium salt of cinchonine, and excess of an aqueous solution of a base, such as potassium hydroxide, sodium hydroxide, lithium hydroxide or cesium hydroxide, preferably potassium hydroxide and a non-polar solvent, such as toluene, is cooled to a temperature of between about −25° C. and about 25° C. To this mixture is added a solution of a compound of formula (18) and an excess molar amount of a compound of formula (10), preferably where $Pg^2$ is an oxygen protecting group, preferably benzyl, in an non-polar/polar aprotic solvent mixture, preferably 1:1, such as toluene/tetrahydrofuran, over a period of time of between about 5 minutes to about 2 hours with stirring. The compound of formula (19) is isolated from the reaction mixture by stan- Compound of formulae (1), (14), (4), (5), (7), (10) and (2) are commercially available, or can be prepared according to methods known to one skilled in the art or by the methods disclosed in PCT Published Patent Application No. WO 2006/110917, PCT Published Patent Application No. WO 2010/45251, PCT Published Patent Application No. WO 2010/045197, PCT Published Patent Application No. WO 2011/047174 and PCT Published Patent Application No. WO 2011/002708.

In general, compounds of formula (I) are prepared according to Method B, as described above in Reaction Scheme 2, by first treating a compound of formula (1), or a pharmaceutically acceptable salt thereof, in a polar aprotic solvent, such as, dimethylformamide, in the presence of a base, such as sodium hydroxide, at a temperature of between about 0° C. and about 50° C., preferably at between about 0° C. and dard isolation conditions, such as extraction with organic solvent, such as ethyl acetate, followed by acid wash, concentration, and filtration as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%.

A quaternary ammonium salt of cinchonine can be prepared by refluxing a suspension of cinchonine and a suitable alkyl halide such as but not limited to, 9-chloromethylanthracene or 1-bromomethylnaphthalene, in a suitable solvent, such as but not limited to, anhydrous toluene or tetrahydrofuran. The product is isolated by filtration or by means of crystallization using a suitable solvent such as but not limited to diethyl ether or methanol (E. J. Corey and M. C. Noe, *Org. Synth.* 2003; 80:38-45).

The compound of formula (19) is then deprotected under suitable deprotection (reduction) conditions, such as treating a mixture of the compound of formula (19), a suitable metal catalyst such as, but not limited to, 10% palladium on carbon or palladium (II) hydroxide and a weak acid, such as acetic acid, formic acid, or trifluoroacetic acid, in a protic/polar aprotic solvent mixture, such as a mixture of a lower alkanol, such as ethanol or methanol, in tetrahydrofuran or ethyl acetate, preferably a 1:1 mixture of ethanol and tetrahydrofuran, with a silane reagent, such as triethylsilane or triphenylsilane, in a protic/polar aprotic solvent, such as tetrahydrofuran, ethyl acetate, ethanol, methanol, at ambient temperature, or with hydrogen gas at atmospheric pressure or at 15 psi. The resulting compound of formula (20) is isolated from the reaction mixture by standard isolation techniques, such as filtration and concentration as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%.

Intramolecular cyclization of a compound of formula (20) to provide a compound of formula (21) is achieved by treating a compound of formula (20) to suitable Mitsunobu reaction conditions, such as the employment of a phosphine reagent, preferably, but not limited to, triphenylphosphine, tributylphosphine, 2-(diphenylphosphino)pyridine, 4-(diphenylphosphino)dimethylaniline and 4-(N,N-dimethylamino)phenyldiphenylphosphine, and an azodicarboxylate ester, such as, but not limited to, diethylazodicarboxylate, diisopropylazodicarboxylate, di-tert-butylazodicarboxylate, di-n-butylazodicarboxylate or tetramethyldiazenedicarboxamide, in a polar aprotic solvent, preferably, but not limited to, tetrahydrofuran, dichloromethane or ethyl acetate. The resulting compound of formula (21) is isolated from the reaction mixture by standard isolation techniques, such as extraction, acid wash, filtration and concentration as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%.

The compound of formula (21) is the deprotected under suitable deprotection conditions, such as treating the compound of formula (21) with a silane reagent, such as triethylsilane, in the presence of an acid, such as trifluoroacetic acid, and heating the reaction mixture at reflux for a period of time of between about 30 minutes and 3 hours. The reaction mixture is then cooled to ambient temperature and concentrated. The compound of formula (22) is then isolated from the concentrate by standard isolation techniques, such as extraction and concentration as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%.

The compound of formula (22) in a polar aprotic solvent, such as dimethylformamide, in the presence of a base, such as cesium carbonate, is treated with an excess molar amount of a compound of formula (2), or a pharmaceutically acceptable salt thereof. The resulting reaction mixture is heated to a temperature of between about 50° C. and 100° C., preferably to about 80° C., for a period of time of between about 30 minutes and about 3 hours. The reaction mixture is then cooled to ambient temperature and the compound of formula (I) is then isolated from the reaction mixture by standard isolation techniques, such as filtration, extraction, concentration and purification by column chromatography as an isolated (S)-enantiomer, or a non-racemic mixture of enantiomers having an enantiomeric excess of the (S)-enantiomer of greater than 80%, preferably greater than 90%, more preferably greater than 95%, most preferably greater than 99%.

A specific method of preparing the compounds of formula (I) as set forth above in Reaction Scheme 2 is illustrated below in Reaction Scheme 2A for the preparation of compounds of formula (Ia), where p, $R^1$ and $R^2$ are as defined above for the compounds of formula (I), as described in the Summary of the Invention, q is 1 or 2, each X is independently halo, typically iodo, bromo or chloro, preferably bromo or chloro, except for the Grignard reagent of formula (5) wherein X is iodo, bromo or chloro, preferably bromo or chloro, R is alkyl, and $Pg^1$ and $Pg^2$ are each independently an oxygen protecting group, such as hydrogen, benzyl, alkyl, tert-butyldiphenylsilyl or triphenylsilyl, and $Pg^3$ is a nitrogen protecting group, such as benzhydryl (diphenylmethyl):

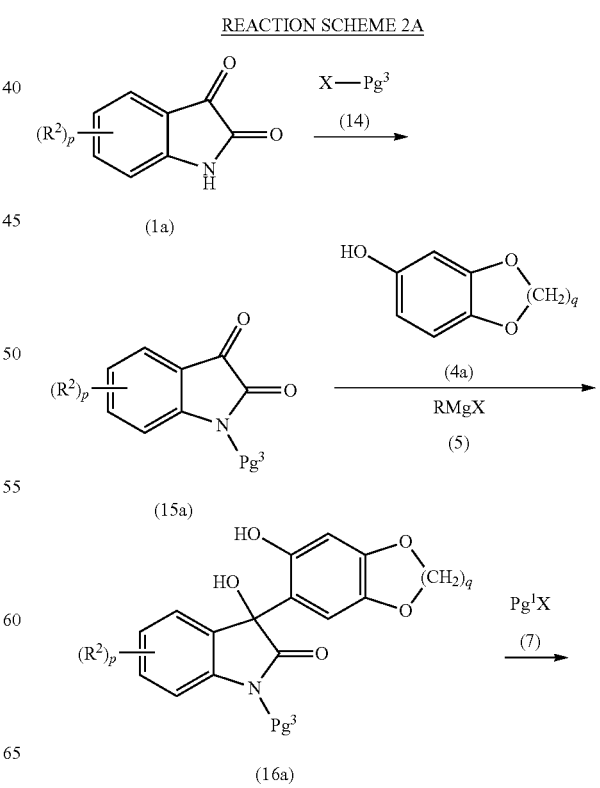

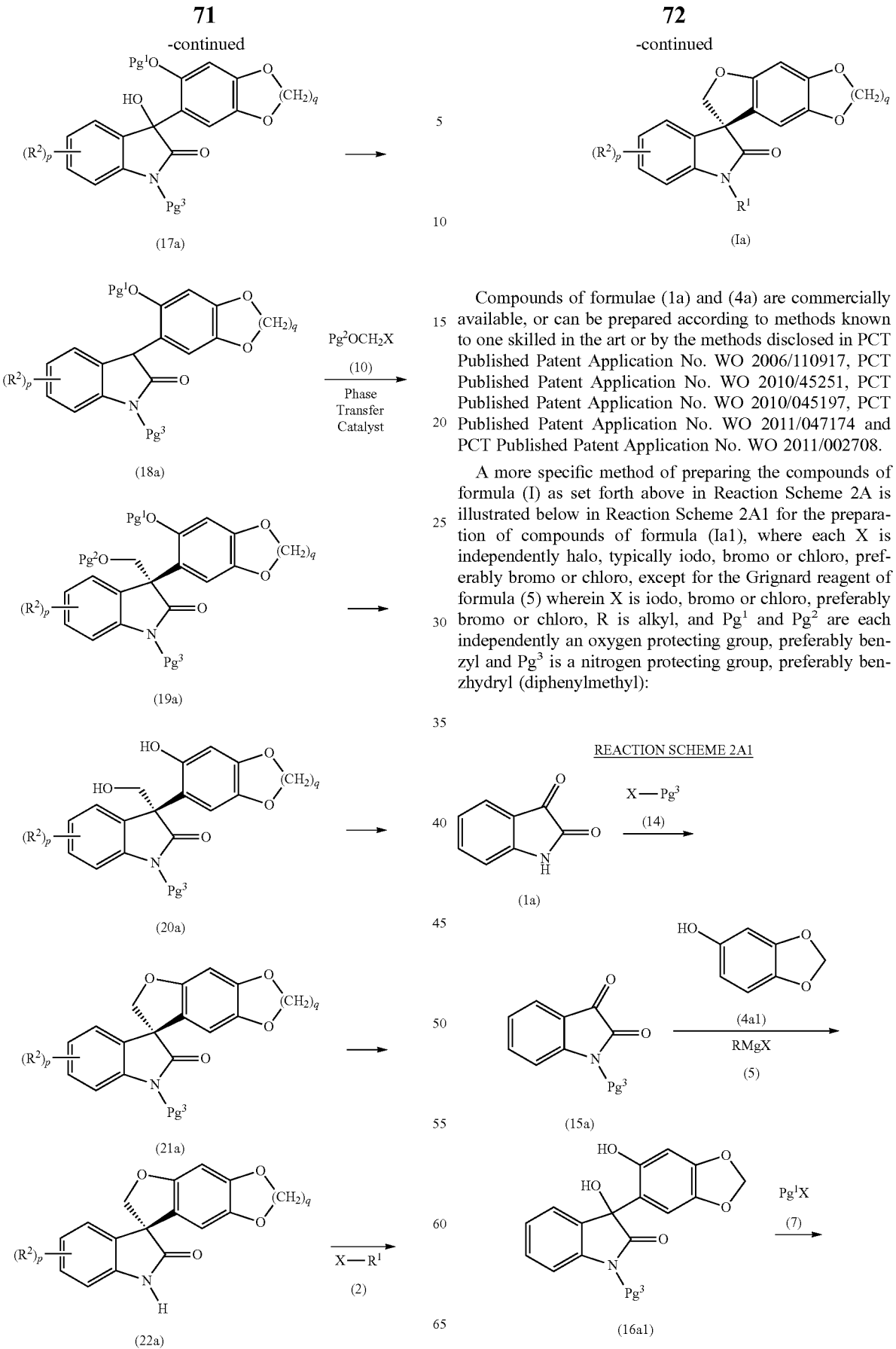

Compounds of formulae (1a) and (4a) are commercially available, or can be prepared according to methods known to one skilled in the art or by the methods disclosed in PCT Published Patent Application No. WO 2006/110917, PCT Published Patent Application No. WO 2010/45251, PCT Published Patent Application No. WO 2010/045197, PCT Published Patent Application No. WO 2011/047174 and PCT Published Patent Application No. WO 2011/002708.

A more specific method of preparing the compounds of formula (I) as set forth above in Reaction Scheme 2A is illustrated below in Reaction Scheme 2A1 for the preparation of compounds of formula (Ia1), where each X is independently halo, typically iodo, bromo or chloro, preferably bromo or chloro, except for the Grignard reagent of formula (5) wherein X is iodo, bromo or chloro, preferably bromo or chloro, R is alkyl, and $Pg^1$ and $Pg^2$ are each independently an oxygen protecting group, preferably benzyl and $Pg^3$ is a nitrogen protecting group, preferably benzhydryl (diphenylmethyl):

REACTION SCHEME 2A1

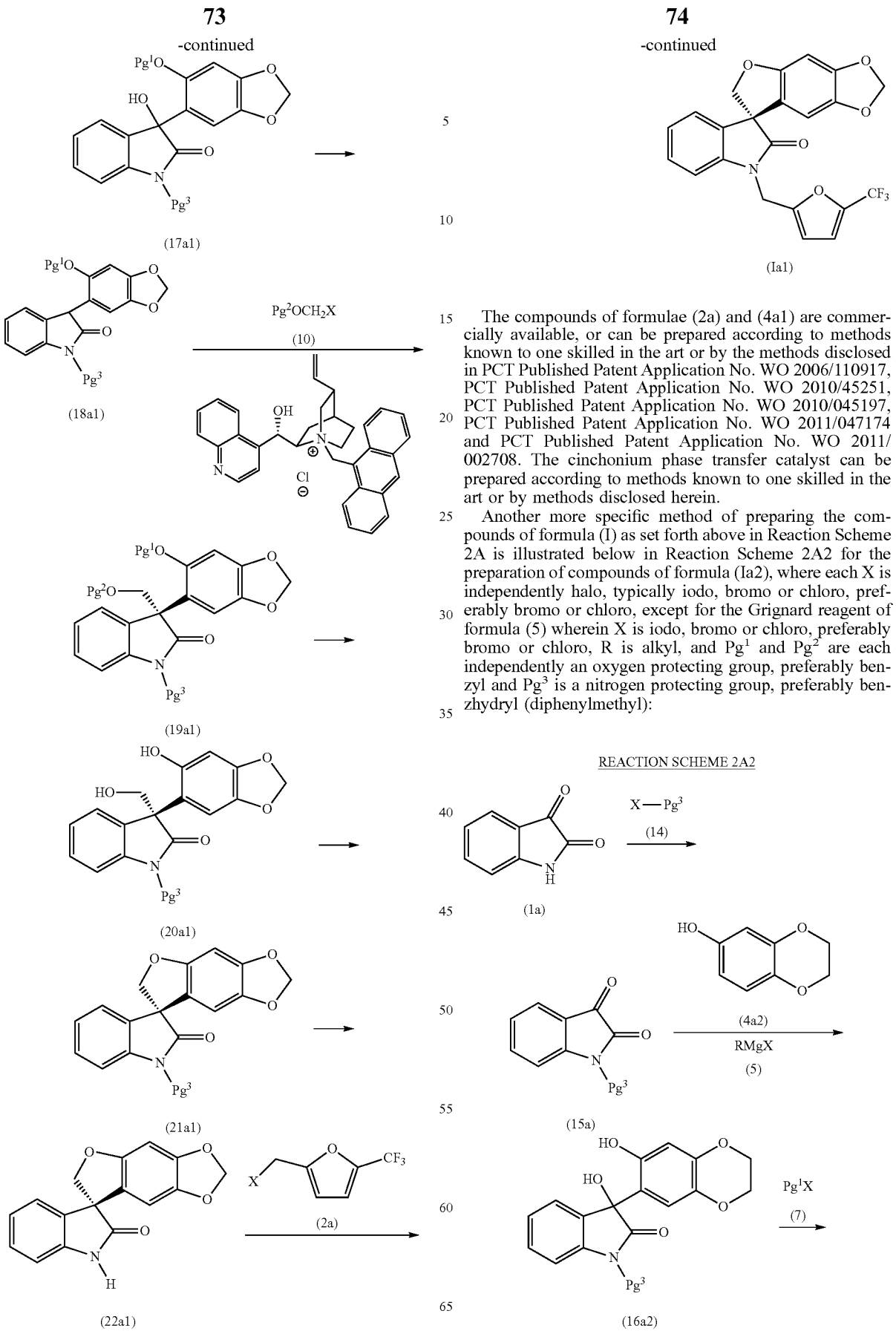

The compounds of formulae (2a) and (4a1) are commercially available, or can be prepared according to methods known to one skilled in the art or by the methods disclosed in PCT Published Patent Application No. WO 2006/110917, PCT Published Patent Application No. WO 2010/45251, PCT Published Patent Application No. WO 2010/045197, PCT Published Patent Application No. WO 2011/047174 and PCT Published Patent Application No. WO 2011/002708. The cinchonium phase transfer catalyst can be prepared according to methods known to one skilled in the art or by methods disclosed herein.

Another more specific method of preparing the compounds of formula (I) as set forth above in Reaction Scheme 2A is illustrated below in Reaction Scheme 2A2 for the preparation of compounds of formula (Ia2), where each X is independently halo, typically iodo, bromo or chloro, preferably bromo or chloro, except for the Grignard reagent of formula (5) wherein X is iodo, bromo or chloro, preferably bromo or chloro, R is alkyl, and $Pg^1$ and $Pg^2$ are each independently an oxygen protecting group, preferably benzyl and $Pg^3$ is a nitrogen protecting group, preferably benzhydryl (diphenylmethyl):

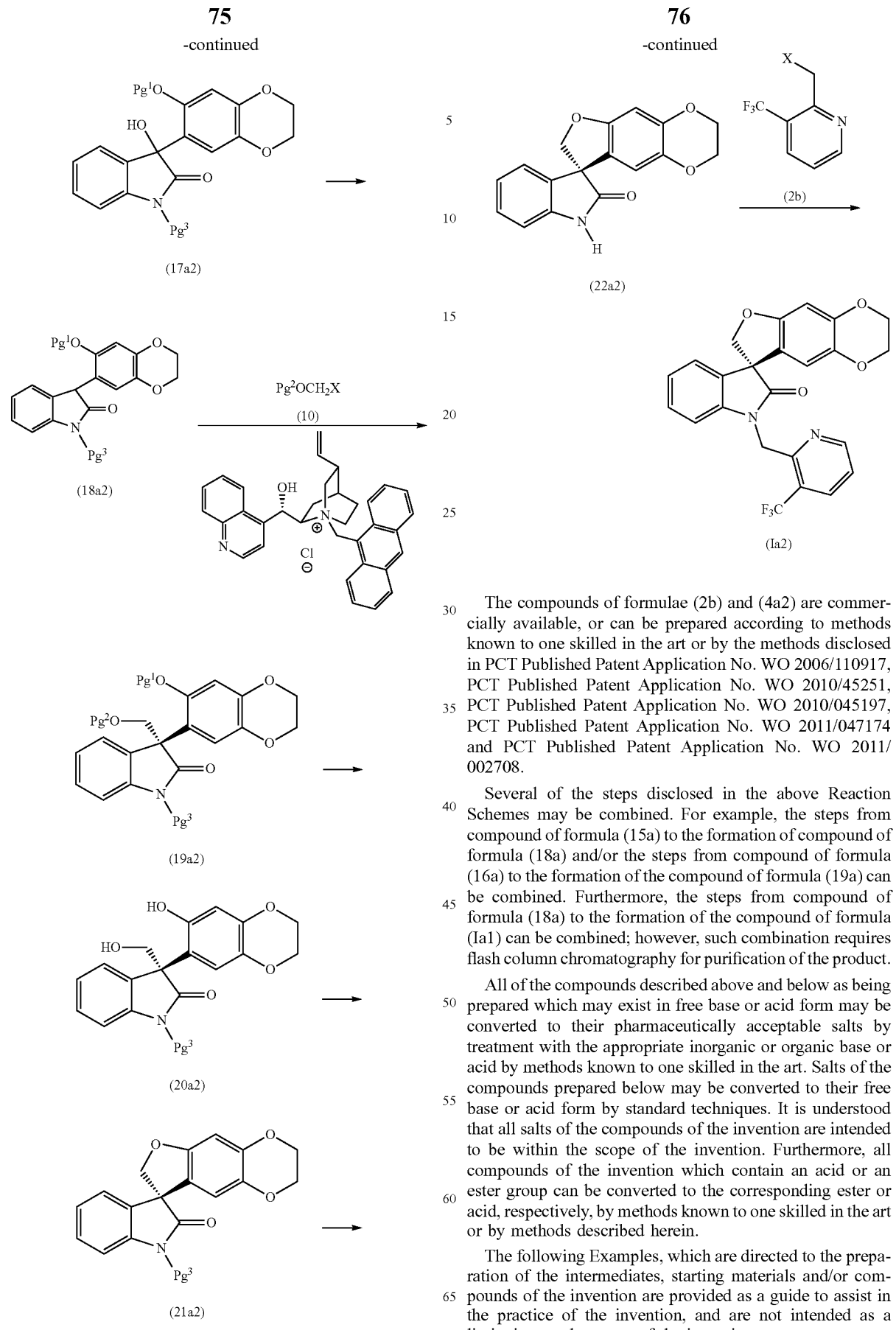

The compounds of formulae (2b) and (4a2) are commercially available, or can be prepared according to methods known to one skilled in the art or by the methods disclosed in PCT Published Patent Application No. WO 2006/110917, PCT Published Patent Application No. WO 2010/45251, PCT Published Patent Application No. WO 2010/045197, PCT Published Patent Application No. WO 2011/047174 and PCT Published Patent Application No. WO 2011/002708.

Several of the steps disclosed in the above Reaction Schemes may be combined. For example, the steps from compound of formula (15a) to the formation of compound of formula (18a) and/or the steps from compound of formula (16a) to the formation of the compound of formula (19a) can be combined. Furthermore, the steps from compound of formula (18a) to the formation of the compound of formula (Ia1) can be combined; however, such combination requires flash column chromatography for purification of the product.

All of the compounds described above and below as being prepared which may exist in free base or acid form may be converted to their pharmaceutically acceptable salts by treatment with the appropriate inorganic or organic base or acid by methods known to one skilled in the art. Salts of the compounds prepared below may be converted to their free base or acid form by standard techniques. It is understood that all salts of the compounds of the invention are intended to be within the scope of the invention. Furthermore, all compounds of the invention which contain an acid or an ester group can be converted to the corresponding ester or acid, respectively, by methods known to one skilled in the art or by methods described herein.

The following Examples, which are directed to the preparation of the intermediates, starting materials and/or compounds of the invention are provided as a guide to assist in the practice of the invention, and are not intended as a limitation on the scope of the invention.

Example 1

Synthesis of 1-{[5-(trifluoromethyl)furan-2-yl]methyl}-1H-indole-2,3-dione

Compound of Formula (3a1)

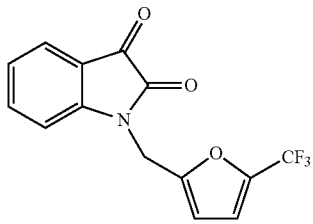 [SMILES: O=C1C(=O)N(Cc2ccc(C(F)(F)F)o2)c2ccccc21]

A. A nitrogen-flushed 10 L reactor was charged with cesium carbonate (1330 g, 4080 mmol) and acetonitrile (4500 mL). To this stirred mixture was added isatin (500 g, 3400 mmol) followed by 2-(bromomethyl)-5-(trifluoromethyl)furan (983 mL, 4080 mmol). The stirred mixture was heated to 28° C. for 16 h and was then filtered and concentrated in vacuo. The resulting material was dissolved in N,N-dimethylformamide to which water was added. The suspension was filtered to afford 1-{[5-(trifluoromethyl)furan-2-yl]methyl}-1H-indole-2,3-dione (953 g) as an orange solid in quantitative yield.

B. Alternatively, to a solution of isatin (5.0 g, 34 mmol) in N,N-dimethylformamide (100 mL) was added 2-(bromomethyl)-5-(trifluoromethyl)furan (5.2 mL, 38 mmol) and anhydrous potassium carbonate (11.7 g, 85 mmol) while stirring under a nitrogen atmosphere at ambient temperature. After 1.5 h, the reaction mixture was filtered and the filtrate was poured into water (1350 mL) with vigorous stirring. The solid was filtered and washed with water to obtain 1-{[5-(trifluoromethyl)furan-2-yl]methyl}-1H-indole-2,3-dione (10.0 g) as an orange solid in quantitative yield: $^1$H NMR (300 MHz, CDCl$_3$) δ7.66-7.59 (m, 2H), 7.19-7.14 (m, 1H), 7.05 (d, J=7.9 Hz, 1H), 6.76-6.75 (m, 1H), 6.46 (d, J=3.4 Hz, 1H), 4.94 (s, 2H); MS (ES+) m/z 295.9 (M+1).

Example 2

Synthesis of 3-hydroxy-3-(6-hydroxy-1,3-benzodioxol-5-yl)-1-{[5-(trifluoromethyl)furan-2-yl]methyl}-1,3-dihydro-2H-indol-2-one Compound of Formula (6a1)

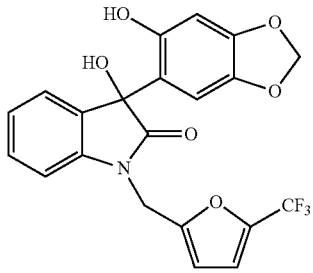 [SMILES: O=C1N(Cc2ccc(C(F)(F)F)o2)c2ccccc2C1(O)c1cc2c(cc1O)OCO2]

To a cooled (0° C.) solution of sesamol (87.7 g, 635 mmol) in tetrahydrofuran (750 mL) was added dropwise a 2.0 M solution of isopropylmagnesium chloride in tetrahydrofuran (265 mL, 530 mmol). The mixture was stirred for 30 minutes at 0° C. and a solution of 1-{[5-(trifluoromethyl)furan-2-yl]methyl}-1H-indole-2,3-dione (125 g, 423 mmol) in tetrahydrofuran (450 mL) was added via dropping funnel. The mixture was stirred at 0° C. for 40 minutes, allowed to warm to ambient temperature, stirred for 16 h and diluted with ethyl acetate (300 mL). The mixture was washed with saturated aqueous ammonium chloride (3×300 mL) and brine (3×300 mL), dried over anhydrous sodium sulfate and filtered. The filtrate was concentrated in vacuo to dryness and the residue triturated in diethyl ether to afford 3-hydroxy-3-(6-hydroxy-1,3-benzodioxol-5-yl)-1-{[5-(trifluoromethyl)furan-2-yl]methyl}-1,3-dihydro-2H-indol-2-one (162 g) as a colorless solid in 88% yield: $^1$H NMR (300 MHz, CDCl$_3$) δ8.91 (s, 1H), 7.49 (d, 1H), 7.43-7.38 (m, 1H), 7.24-7.19 (m, 1H), 7.01 (d, J=7.8 Hz, 1H), 6.71-6.70 (m, 1H), 6.57 (s, 1H), 6.33-6.32 (m, 1H), 6.26 (s, 1H), 5.88-5.86 (m, 2H), 4.90 (q, J=16.3 Hz, 2H), 4.43 (s, 1H); MS (ES−) m/z 431.8 (M−1).

Example 3

Synthesis of 3-[6-(benzyloxy)-1,3-benzodioxol-5-yl]-3-hydroxy-1-{[5-(trifluoromethyl)furan-2-yl]methyl}-1,3-dihydro-2H-indol-2-one Compound of Formula (8a1)

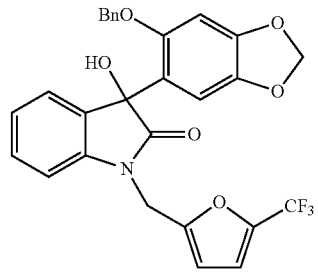 [SMILES: O=C1N(Cc2ccc(C(F)(F)F)o2)c2ccccc2C1(O)c1cc2c(cc1OCc1ccccc1)OCO2]

To a cooled (0° C.) mixture of 3-hydroxy-3-(6-hydroxy-1,3-benzodioxol-5-yl)-1-{[5-(trifluoromethyl)furan-2-yl]methyl}-1,3-dihydro-2H-indol-2-one (105 g, 242 mmol) and potassium carbonate (67.4 g, 488 mmol) in anhydrous N,N-dimethylformamide (500 mL) was added benzyl bromide (35 mL, 290 mmol) dropwise over 30 minutes. The mixture was allowed to warm to ambient temperature, stirred for 22 h and poured into ice-cold water (2500 mL) with vigorous stirring. The resulting suspension was filtered and the colorless solid washed with water (3000 mL) and hexanes (1000 mL), re-suspended in water (2000 mL) and stirred for 3 days. The suspension was filtered and washed with water (1500 mL) to afford 3-[6-(benzyloxy)-1,3-benzodioxol-5-yl]-3-hydroxy-1-{[5-(trifluoromethyl)furan-2-yl]methyl}-1,3-dihydro-2H-indol-2-one (125 g) as a colorless solid in 99% yield: $^1$H NMR (300 MHz, CDCl$_3$) δ7.40 (s, 1H), 7.32-7.23 (m, 4H), 7.08-6.93 (m, 4H), 6.65 (d, J=7.8 Hz, 1H), 6.57-6.56 (m, 1H), 6.44 (s, 1H), 6.18-6.16 (m, 1H), 5.93 (s, 2H), 4.64-4.53 (m, 3H), 3.65-3.60 (m, 2H); MS (ES+) m/z 505.8 (M−18).

Example 4

Synthesis of 3-[6-(benzyloxy)-1,3-benzodioxol-5-yl]-1-{[5-(trifluoromethyl)furan-2-yl]methyl}-1,3-dihydro-2H-indol-2-one Compound of Formula (9a1)

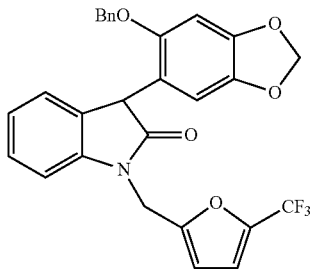 [SMILES: O=C1C(c2cc3c(cc2OCc2ccccc2)OCO3)c2ccccc2N1Cc1ccc(C(F)(F)F)o1]

To a cooled (0° C.) solution of 3-[6-(benzyloxy)-1,3-benzodioxol-5-yl]-3-hydroxy-1-{[5-(trifluoromethyl)furan-2-yl]methyl}-1,3-dihydro-2H-indol-2-one (58.0 g, 111 mmol) in dichloromethane (350 mL) was added triethylsilane (150 mL) and trifluoroacetic acid (300 mL). The solution was allowed to warm to ambient temperature, stirred for 17 h and concentrated in vacuo. The residue was triturated in diethyl ether (100 mL) to afford 3-[6-(benzyloxy)-1,3-benzodioxol-5-yl]-1-{[5-(trifluoromethyl)furan-2-yl]methyl}-1,3-dihydro-2H-indol-2-one (33.4 g) as a colorless solid in 59% yield: $^1$H NMR (300 MHz, CDCl$_3$) δ7.29-7.20 (m, 4H), 7.04-6.97 (m, 4H), 6.75 (d, J=7.8 Hz, 1H), 6.66 (s, 1H), 6.62-6.61 (m, 1H), 6.55 (s, 1H), 6.21-6.20 (m, 1H), 5.91-5.90 (m, 2H), 4.84-4.65 (m, 4H), 4.21-4.13 (m, 1H); MS (ES+) m/z 507.8 (M+1).

Example 5

Synthesis of (9S)-1-(anthracen-9-ylmethyl)cinchonan-1-ium-9-ol chloride (Phase-transfer catalyst)

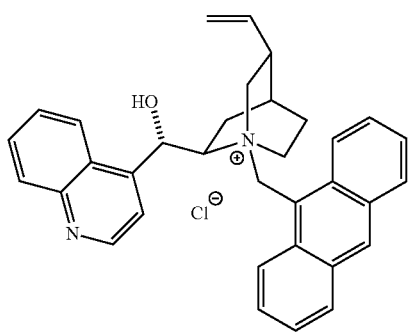 [SMILES: C=CC1C[N+]2(Cc3c4ccccc4cc4ccccc34)CCC1CC2[C@@H](O)c1ccnc2ccccc12 ; [Cl-]]

A. A suspension of cinchonine (31.3 g, 106 mmol) and 9-chloromethylanthracene (25.3 g, 112 mmol) in anhydrous toluene (320 mL) in a foil-wrapped flask was heated at reflux for 3.5 h. The reaction was allowed to cool to ambient temperature and diethyl ether (400 mL) was added. The suspension was cooled to 10° C. and the resulting precipitate was filtered and washed with diethyl ether/toluene (1:1 v/v, 200 mL), followed by diethyl ether (200 mL). The solid was heated at reflux in ethanol (400 mL) along with decolorizing charcoal (46 g) for 1 h. The warm solution was filtered through a pad of diatomaceous earth and the pad was rinsed with ethanol (150 mL). A solid crystallized upon cooling to ambient temperature. The solid was collected by filtration to afford (9S)-1-(anthracen-9-ylmethyl)cinchonan-1-ium-9-ol chloride (27.2 g) as a pale yellow solid in 49% yield. The filtrate was concentrated to a volume of 70 mL, inducing the formation of a further crop of crystals that were filtered to afford a further crop of (9S)-1-(anthracen-9-ylmethyl)cinchonan-1-ium-9-ol chloride (5.6 g) in 10% yield: $^1$H NMR (300 MHz, CDCl$_3$) δ9.29 (d, J=8.8 Hz, 1H), 8.93 (d, J=8.4 Hz, 1H), 8.87-8.86 (m, 1H), 8.42 (d, J=9.0 Hz, 1H), 8.27 (s, 1H), 8.06 (d, J=4.4 Hz, 1H), 7.86 (s, 1H), 7.60-7.54 (m, 2H), 7.46 (d, J=8.3 Hz, 1H), 7.33-6.91 (m, 7H), 6.49 (d, J=13.3 Hz, 1H), 5.64-5.53 (m, 1H), 5.03 (d, J=10.5 Hz, 1H), 4.87 (d, J=17.2 Hz, 1H), 4.76-4.68 (m, 1H), 4.46-4.40 (m, 1H), 4.28-4.20 (m, 1H), 2.51-2.44 (m, 1H), 2.37-2.27 (m, 1H), 1.99-1.65 (m, 4H), 1.52 (br s, 1H), 1.41-1.33 (m, 1H), 0.67-0.60 (m, 1H); MS (ES+) m/z 484.9 (M−35).

B. Alternatively, a mixture of cinchonine (130 g, 442 mmol), 9-chloromethylanthracene (157 g, 663 mmol) and anhydrous toluene (1.4 L) was heated at reflux under nitrogen atmosphere for 18 h and was allowed to cool to ambient temperature. Methyl tert-butyl ether (1.9 L) was added and the mixture was stirred at 15-25° C. for 0.5 h, during which time a solid was deposited. The solid was collected by filtration, washed with toluene (100 mL) and dried in vacuo below 60° C. for 12 h to afford (9S)-1-(anthracen-9-ylmethyl)cinchonan-1-ium-9-ol chloride (156 g) as a colorless solid in 67% yield: $^1$H NMR (300 MHz, CDCl$_3$) δ9.29 (d, 1H), 8.93 (d, 1H), 8.86 (d, 1H), 8.42 (d, 1H), 8.27 (s, 1H), 8.06 (d, 1H), 7.86 (s, 1H), 7.57 (t, 2H), 7.46 (d, 1H), 7.33-6.91 (m, 7H), 6.49 (d, 1H), 5.58 (ddd, 1H), 5.03 (d, 1H), 4.87 (d, 1H), 4.76-4.68 (m, 1H), 4.43 (t, 1H), 4.24 (t, 1H), 2.48 (t, 1H), 2.37-2.27 (m, 1H), 1.99-1.65 (m, 4H), 1.52 (br s, 1H), 1.41-1.33 (m, 1H), 0.67-0.60 (m, 1H); MS (ES+) m/z 484.9 (M−35).

Example 6

Synthesis of (3S)-3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one Compound of Formula (12a1)

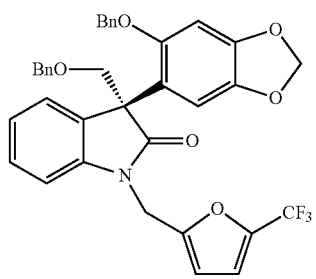 [SMILES: O=C1N(Cc2ccc(C(F)(F)F)o2)c2ccccc2[C@@]1(COCc1ccccc1)c1cc2c(cc1OCc1ccccc1)OCO2]

A. A mixture of 50% w/w aqueous potassium hydroxide (73 mL, 650 mmol), toluene (250 mL) and (9S)-1-(anthracen-9-ylmethyl)cinchonan-1-ium-9-ol chloride (1.04 g, 2.00 mmol) was degassed with nitrogen and cooled in an ice/salt bath to an internal temperature of −10° C. To this mixture was added a solution of 3-[6-(benzyloxy)-1,3-benzodioxol- 5-yl]-1-{[5-(trifluoromethyl)furan-2-yl]methyl}-1,3-dihydro-2H-indol-2-one (10.1 g, 19.9 mmol) and benzyl chloromethyl ether (3.6 mL, 26 mmol) in degassed toluene (110 mL) dropwise via syringe pump over 1.5 h. The mixture was stirred for a further 0.5 h, diluted with ethyl acetate (100 mL) and the phases were separated. The organic phase was washed with 1 N hydrochloric acid (3×150 mL) and brine (2×150 mL), dried over sodium sulfate and filtered. The filtrate was concentrated in vacuo to afford gummy material which was then filtered through a pad of silica gel. The pad was washed with hexanes/ethyl acetate (1:1 v/v, 300 mL). The filtrate was concentrated in vacuo and the residue was triturated in a mixture of diethyl ether and hexanes to afford 3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one as a colorless solid. A second crop of 3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one was obtained from the filtrate by concentrating in vacuo to dryness and triturating the residue in a mixture of diethyl ether and hexanes to afford 3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one as a colorless solid. The combined solids were dissolved in ethanol (120 mL), heated at reflux and the resultant solution was allowed to cool to ambient temperature. To this solution was added a seed crystal of racemic 3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one and the mixture was allowed to stand at ambient temperature for 24 h. The crystals were removed by filtration and the filtrate was concentrated in vacuo to afford (3S)-3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one (9.50 g, >99.5% ee) as a colorless solid in 66% yield. The solid was recrystallized a second time via the above procedure to afford a further crop of (3S)-3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one (1.70 g, >99.5% ee) as a colorless solid in 14% yield.

B. Alternatively, a mixture of 50% w/w aqueous potassium hydroxide (146 mL, 1300 mmol), toluene (500 mL), and (9S)-1-(anthracen-9-ylmethyl)cinchonan-1-ium-9-ol chloride (0.51 g, 0.98 mmol) was degassed with nitrogen and cooled in an ice/salt bath to an internal temperature of −18° C. To this mixture was added a solution of 3-[6-(benzyloxy)-1,3-benzodioxol-5-yl]-1-{[5-(trifluoromethyl)furan-2-yl]methyl}-1,3-dihydro-2H-indol-2-one (20.0 g, 39.4 mmol) and benzyl chloromethyl ether (6.0 mL, 43 mmol) in degassed toluene (220 mL) dropwise via syringe pump over 2 h. The mixture was stirred for a further 15 minutes, diluted with ethyl acetate (250 mL) and the phases were separated. The organic phase was washed with 1 N hydrochloric acid (3×200 mL) and brine (3×250 mL), dried over sodium sulfate and filtered. The filtrate was concentrated in vacuo. The residue was dissolved in ethanol (285 mL), decolorizing charcoal (21 g) was added and the mixture was heated at reflux for 1 h. The mixture was filtered while hot through a pad of diatomaceous earth. The filtrate was concentrated in vacuo and the residue was dissolved in ethanol (300 mL). The mixture was heated at reflux and was allowed to cool to ambient temperature. To this solution was added a seed crystal of racemic 3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one and the mixture was allowed to stand at ambient temperature for 24 h. The crystals were removed by filtration and the filtrate was concentrated in vacuo to dryness. The residue was triturated in diethyl ether to afford (3S)-3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one (17.0 g) as a colorless solid in 69% yield: $^1$H NMR (300 MHz, CDCl$_3$) δ 7.36-7.26 (m, 4H), 7.21-7.15 (m, 4H), 7.01-6.97 (m, 4H), 6.89-6.86 (m, 2H), 6.46-6.43 (m, 2H), 6.35-6.34 (m, 1H), 5.93-5.88 (m, 3H), 4.77 (d, J=16.9 Hz, 1H), 4.57 (d, J=10.6 Hz, 1H), 4.44 (d, J=10.5 Hz, 1H), 4.38 (q, J=12.1 Hz, 2H), 4.06 (dd, J=8.4, 19.7 Hz, 2H), 3.34 (d, J=16.9 Hz, 1H); MS (ES+) m/z 627.8 (M+1); ee (enantiomeric excess) >99.5% (HPLC, Chiralpak IA, 2.5% acetonitrile in methyl tert-butyl ether).

Example 7

Synthesis of (3S)-3-(6-hydroxy-1,3-benzodioxol-5-yl)-3-(hydroxymethyl)-1-{[5-(trifluoromethyl)furan-2-yl]methyl}-1,3-dihydro-2H-indol-2-one Compound of Formula (13a1)

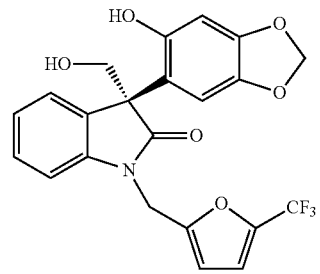 [SMILES: O=C1N(Cc2ccc(C(F)(F)F)o2)c2ccccc2[C@@]1(CO)c1cc2c(cc1O)OCO2]

To a mixture of (3S)-3-[6-(benzyloxy)-1,3-benzodioxol-5-yl]-3-[(benzyloxy)methyl]-1-{[5-(trifluoromethyl)furan-2-yl]methyl}-1,3-dihydro-2H-indol-2-one (10.3 g, 16.4 mmol), 10% w/w palladium on carbon, 50% wetted powder (4.0 g, 1.9 mmol) and acetic acid (4.7 mL, 82 mmol) in a 1:1 v/v degassed mixture of ethanol/tetrahydrofuran (170 mL) was added a solution of triethylsilane (5.9 mL, 37 mmol) in degassed tetrahydrofuran (50 mL) at ambient temperature dropwise via syringe pump over 75 minutes. After stirring at ambient temperature for a further 2.5 h, further triethylsilane (0.26 mL, 1.6 mmol) in tetrahydrofuran (5 mL) was added over 15 minutes. The mixture was stirred for a further 3.5 h at ambient temperature and the mixture filtered through a pad of diatomaceous earth and the pad was rinsed with ethyl acetate (100 mL) and the filtrate was concentrated in vacuo to afford (3S)-3-(6-hydroxy-1,3-benzodioxol-5-yl)-3-(hydroxymethyl)-1-{[5-(trifluoromethyl)furan-2-yl]methyl}-1,3-dihydro-2H-indol-2-one as a colorless solid that was carried forward without further purification: $^1$H NMR (300 MHz, CDCl$_3$) δ9.79 (s, 1H), 7.44-7.37 (m, 2H), 7.30-7.24 (m, 1H), 7.02 (d, J=7.8 Hz, 1H), 6.69-6.68 (m, 1H), 6.57 (s, 1H), 6.54 (s, 1H), 6.30-6.29 (m, 1H), 5.88-5.84 (m, 2H), 4.96 (q, J=16.5 Hz, 2H), 4.76 (dd, J=8.8, 10.8 Hz, 1H), 4.15-4.08 (m, 1H), 1.83-1.79 (m, 1H); MS (ES+) m/z 447.8 (M+1).

Example 8

Synthesis of (7S)-1'-{[5-(trifluoromethyl)furan-2-yl]methyl}spiro[furo[2,3-f][1,3]benzodioxole-7,3'-indol]-2'(1'H)-one Compound of Formula (Ia1)

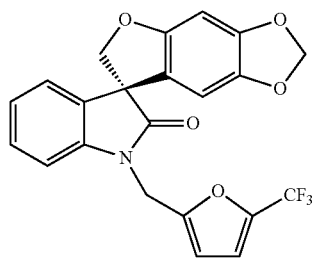 [SMILES: O=C1N(Cc2ccc(C(F)(F)F)o2)c2ccccc2[C@]12COc1cc3c(cc12)OCO3]

To a cooled (0° C.) solution of (3S)-3-(6-hydroxy-1,3-benzodioxol-5-yl)-3-(hydroxymethyl)-1-{[5-(trifluoromethyl)furan-2-yl]methyl}-1,3-dihydro-2H-indol-2-one prepared according to the procedure described in Example 7 (16.4 mmol) and 2-(diphenylphosphino)pyridine (5.2 g, 20 mmol) in anhydrous tetrahydrofuran (170 mL) was added di-tert-butylazodicarboxylate (4.5 g, 20 mmol). The mixture was stirred for 2 h at 0° C., then the reaction was diluted with ethyl acetate (170 mL), washed with 3 N hydrochloric acid (7×50 mL) and brine (2×100 mL), dried over anhydrous sodium sulfate, filtered and concentrated in vacuo. The residue was dissolved in ethanol (80 mL), decolorizing charcoal (15 g) was added and the mixture was heated at reflux for 1 h. The mixture was filtered while hot through a pad of diatomaceous earth. The filtrate was concentrated in vacuo and the residue triturated in a mixture of diethyl ether/hexanes to afford (7S)-1'-{[5-(trifluoromethyl)furan-2-yl]methyl}spiro-[furo[2,3-f][1,3]benzodioxole-7,3'-indol]-2'(1'H)-one (1.30 g) as a colorless solid in 18% yield. The mother liquor from the trituration was concentrated in vacuo, trifluoroacetic acid (20 mL) was added and the mixture stirred for 3 h at ambient temperature. The mixture was diluted with ethyl acetate (100 mL), washed with saturated aqueous ammonium chloride (100 mL), 3 N hydrochloric acid (4×60 mL) and brine (2×100 mL), dried over anhydrous sodium sulfate, filtered and concentrated in vacuo. The residue was purified by column chromatography, eluting with a gradient of ethyl acetate in hexanes to afford further (7S)-1'-{[5-(trifluoromethyl)furan-2-yl]methyl}spiro-[furo[2,3-f][1,3]benzodioxole-7,3'-indol]-2'(1'H)-one (2.6 g) as a colorless solid (37% yield, overall yield 55% over 2 steps): $^1$H NMR (300 MHz, CDCl$_3$) δ7.29-6.96 (m, 4H), 6.73 (s, 1H), 6.50 (s, 1H), 6.38 (s, 1H), 6.09 (s, 1H), 5.85 (br s, 2H), 5.06 (d, J=16.0 Hz, 1H), 4.93-4.84 (m, 2H), 4.68-4.65 (m, 1H); MS (ES+) m/z 429.8 (M+1); ee (enantiomeric excess) >99.5% (HPLC, Chiralpak IA, 2.5% acetonitrile in methyl tert-butyl ether).

Example 9

Synthesis of 1-(diphenylmethyl)-1H-indole-2,3-dione

Compound of Formula (15a)

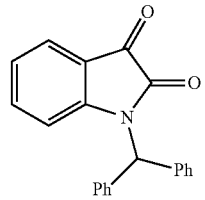 [SMILES: O=C1C(=O)N(C(c2ccccc2)c2ccccc2)c2ccccc21]

A. To a suspension of hexanes-washed sodium hydride (34.0 g, 849 mmol) in anhydrous N,N-dimethylformamide (400 mL) at 0° C. was added a solution of isatin (99.8 g, 678 mmol) in anhydrous N,N-dimethylformamide (400 mL) dropwise over 30 minutes. The reaction mixture was stirred for 1 h at 0° C. and a solution of benzhydryl bromide (185 g, 745 mmol) in anhydrous N,N-dimethylformamide (100 mL) was added dropwise over 15 minutes. The reaction mixture was allowed to warm to ambient temperature, stirred for 16 h and heated at 60° C. for 2 h. The mixture was cooled to 0° C. and water (500 mL) was added. The mixture was poured into water (2 L), causing a precipitate to be deposited. The solid was collected by suction filtration and washed with water (2000 mL) to afford 1-(diphenylmethyl)-1H-indole-2,3-dione (164 g) as an orange solid in 77% yield.

B. Alternatively, to a mixture of isatin (40.0 g, 272 mmol), cesium carbonate (177 g, 543 mmol) and N,N-dimethylformamide (270 mL) at 80° C. was added dropwise a solution of benzhydryl bromide (149 g, 544 mmol) in N,N-dimethylformamide (200 mL) over 30 minutes. The reaction mixture was heated at 80° C. for 3 h, allowed to cool to ambient temperature and filtered through a pad of diatomaceous earth. The pad was rinsed with ethyl acetate (1000 mL). The filtrate was washed with saturated aqueous ammonium chloride (4×200 mL), 1 N hydrochloric acid (200 mL) and brine (4×200 mL), dried over anhydrous sodium sulfate, filtered and concentrated in vacuo. The residue was triturated with diethyl ether to afford 1-(diphenylmethyl)-1H-indole-2,3-dione (59.1 g) as an orange solid in 69% yield. The mother liquor from the trituration was concentrated in vacuo and the residue triturated in diethyl ether to afford a further portion of 1-(diphenylmethyl)-1H-indole-2,3-dione (8.2 g) in 10% yield: $^1$H NMR (300 MHz, CDCl$_3$) δ7.60 (d, J=7.4 Hz, 1H), 7.34-7.24 (m, 11H), 7.05-6.97 (m, 2H), 6.48 (d, J=8.0 Hz, 1H); MS (ES+) m/z 313.9 (M+1).

C. Alternatively, a mixture of isatin (500 g, 3.4 mol) and anhydrous N,N-dimethylformamide (3.5 L) was stirred at 15-35° C. for 0.5 h. Cesium carbonate (2.2 kg, 6.8 mol) was added and the mixture stirred at 55-60° C. for 1 h. A solution of benzhydryl bromide (1.26 kg, 5.1 mol) in anhydrous N,N-dimethylformamide (1.5 L) was added and the resultant mixture stirred at 80-85° C. for 1 h, allowed to cool to ambient temperature and filtered. The filter cake was washed with ethyl acetate (12.5 L). To the combined filtrate and washes was added 1 N hydrochloric acid (5 L). The phases were separated and the aqueous phase was extracted with ethyl acetate (2.5 L). The combined organic extracts were washed with 1 N hydrochloric acid (2×2.5 L) and brine (3×2.5 L) and concentrated in vacuo to a volume of approximately 750 mL. Methyl tert-butyl ether (2 L) was added and the mixture was cooled to 5-15° C., causing a solid to be deposited. The solid was collected by filtration, washed with methyl tert-butyl ether (250 mL) and dried in vacuo at 50-55° C. for 16 h to afford 1-(diphenylmethyl)-1H-indole-2,3-dione (715 g) as an orange solid in 67% yield: $^1$H NMR (300 MHz, CDCl$_3$) δ7.60 (d, J=7.4 Hz, 1H), 7.34-7.24 (m, 11H), 7.05-6.97 (m, 2H), 6.48 (d, J=8.0 Hz, 1H); MS (ES+) m/z 313.9 (M+1).

Example 10

Synthesis of 1-(diphenylmethyl)-3-hydroxy-3-(6-hydroxy-1,3-benzodioxol-5-yl)-1,3-dihydro-2H-indol-2-one Compound of Formula (16a1)

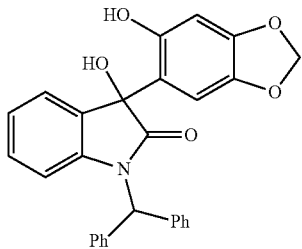 [SMILES: O=C1N(C(c2ccccc2)c2ccccc2)c2ccccc2C1(O)c1cc2c(cc1O)OCO2]

A. To a solution of sesamol (33.1 g, 239 mmol) in anhydrous tetrahydrofuran (500 mL) at 0° C. was added dropwise a 2 M solution of isopropylmagnesium chloride in tetrahydrofuran (104 mL, 208 mmol), followed by 1-(diphenylmethyl)-1H-indole-2,3-dione (50.0 g, 160 mmol) and tetrahydrofuran (100 mL). The reaction mixture was stirred at ambient temperature for 5 h, diluted with ethyl acetate (1500 mL), washed with saturated aqueous ammonium chloride (400 mL) and brine (2×400 mL), dried over anhydrous sodium sulfate, filtered and concentrated in vacuo. The residue was triturated with a mixture of diethyl ether and hexanes to afford 1-(diphenylmethyl)-3-hydroxy-3-(6-hydroxy-1,3-benzodioxol-5-yl)-1,3-dihydro-2H-indol-2-one (70.7 g) as a colorless solid in 98% yield: $^1$H NMR (300 MHz, CDCl$_3$) δ9.12 (br s, 1H), 7.45-7.43 (m, 1H), 7.30-7.22 (m, 10H), 7.09-7.07 (m, 2H), 6.89 (s, 1H), 6.56-6.55 (m, 1H), 6.47-6.46 (m, 1H), 6.29-6.28 (m, 1H), 5.86 (s, 2H), 4.52 (br s, 1H); MS (ES+) m/z 433.7 (M−17).

B. Alternatively, a mixture of sesamol (0.99 kg, 7.2 mol) and anhydrous tetrahydrofuran (18 L) was stirred at 15-35° C. for 0.5 h and cooled to −5-0° C. Isopropyl magnesium chloride (2.0 M solution in tetrahydrofuran, 3.1 L, 6.2 mol) was added, followed by 1-(diphenylmethyl)-1H-indole-2,3-dione (1.50 kg, 4.8 mol) and further anhydrous tetrahydrofuran (3 L). The mixture was stirred at 15-25° C. for 5 h. Ethyl acetate (45 L) and saturated aqueous ammonium chloride (15 L) were added. The mixture was stirred at 15-25° C. for 0.5 h and was allowed to settle for 0.5 h. The phases were separated and the organic phase was washed with brine (2.3 L) and concentrated in vacuo to a volume of approximately 4 L. Methyl tert-butyl ether (9 L) was added and the mixture concentrated in vacuo to a volume of approximately 4 L. Heptane (6 L) was added and the mixture was stirred at 15-25° C. for 2 h, causing a solid to be deposited. The solid was collected by filtration, washed with methyl tert-butyl ether (0.3 L) and dried in vacuo at 50-55° C. for 7 h to afford 1-(diphenylmethyl)-3-hydroxy-3-(6-hydroxy-1,3-benzodioxol-5-yl)-1,3-dihydro-2H-indol-2-one (2.12 kg) as an off-white solid in 98% yield: $^1$H NMR (300 MHz, CDCl$_3$) δ9.12 (br s, 1H), 7.45-7.43 (m, 1H), 7.30-7.22 (m, 10H), 7.09-7.07 (m, 2H), 6.89 (s, 1H), 6.56-6.55 (m, 1H), 6.47-6.46 (m, 1H), 6.29-6.28 (m, 1H), 5.86 (s, 2H), 4.52 (br s, 1H); MS (ES+) m/z 433.7 (M−17).

Example 11

Synthesis of 3-[6-(benzyloxy)-1,3-benzodioxol-5-yl]-1-(diphenylmethyl)-3-hydroxy-1,3-dihydro-2H-indol-2-one Compound of Formula (17a1)

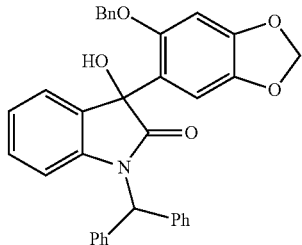 [SMILES: O=C1N(C(c2ccccc2)c2ccccc2)c2ccccc2C1(O)c1cc2c(cc1OCc1ccccc1)OCO2]

A. A mixture of 1-(diphenylmethyl)-3-hydroxy-3-(6-hydroxy-1,3-benzodioxol-5-yl)-1,3-dihydro-2H-indol-2-one (30.0 g, 66.5 mmol), benzyl bromide (8.3 mL, 70 mmol), and potassium carbonate (18.4 g, 133 mmol) in anhydrous N,N-dimethylformamide (100 mL) was stirred at ambient temperature for 16 h. The reaction mixture was filtered and the solid was washed with N,N-dimethylformamide (100 mL). The filtrate was poured into water (1000 mL) and the resulting precipitate was collected by suction filtration and washed with water to afford 3-[6-(benzyloxy)-1,3-benzodioxol-5-yl]-1-(diphenylmethyl)-3-hydroxy-1,3-dihydro-2H-indol-2-one (32.0 g) as a beige solid in 83% yield: $^1$H NMR (300 MHz, CDCl$_3$) δ7.42-7.28 (m, 9H), 7.22-7.14 (m, 6H), 7.10-6.93 (m, 3H), 6.89-6.87 (m, 2H), 6.53 (d, J=7.6 Hz, 1H), 6.29 (br s, 1H), 5.88 (s, 1H), 5.85 (s, 1H), 4.66 (d, J=14.2 Hz, 1H), 4.51 (d, J=14.1 Hz, 1H), 3.95 (s, 1H); MS (ES+) m/z 542.0 (M+1), 523.9 (M−17).

B. Alternatively, to a solution of 1-(diphenylmethyl)-3-hydroxy-3-(6-hydroxy-1,3-benzodioxol-5-yl)-1,3-dihydro-2H-indol-2-one (2.1 kg, 4.6 mol) in anhydrous N,N-dimethylformamide (8.4 L) at 20-30° C. was added potassium carbonate (1.3 kg, 9.2 mol), followed by benzyl bromide (0.58 L, 4.8 mol). The mixture was stirred at 20-30° C. for 80 h and filtered. The filter cake was washed with N,N-dimethylformamide (0.4 L) and the filtrate was poured into water (75 L), causing a solid to be deposited. The mixture was stirred at 15-25° C. for 7 h. The solid was collected by filtration, washed with water (2 L) and dried in vacuo at 50-60° C. for 48 h to afford 3-[6-(benzyloxy)-1,3-benzodioxol-5-yl]-1-(diphenylmethyl)-3-hydroxy-1,3-dihydro-2H-indol-2-one (2.11 kg) as an off-white solid in 84% yield: $^1$H NMR (300 MHz, CDCl$_3$) δ7.42-7.28 (m, 9H), 7.22-7.14 (m, 6H), 7.10-6.93 (m, 3H), 6.89-6.87 (m, 2H), 6.53 (d, J=7.6 Hz, 1H), 6.29 (br s, 1H), 5.88 (s, 1H), 5.85 (s, 1H), 4.66 (d, J=14.2 Hz, 1H), 4.51 (d, J=14.1 Hz, 1H), 3.95 (s, 1H); MS (ES+) m/z 542.0 (M+1).

Example 12

Synthesis of 3-[6-(benzyloxy)-1,3-benzodioxol-5-yl]-1-(diphenylmethyl)-1,3-dihydro-2H-indol-2-one Compound of Formula (18a1)

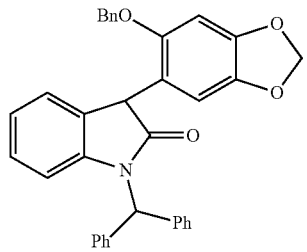 [SMILES: O=C1C(c2cc3c(cc2OCc2ccccc2)OCO3)c2ccccc2N1C(c1ccccc1)c1ccccc1]

A. To a solution of 3-[6-(benzyloxy)-1,3-benzodioxol-5-yl]-1-(diphenylmethyl)-3-hydroxy-1,3-dihydro-2H-indol-2-one (32.0 g, 57.7 mmol) in dichloromethane (100 mL) was added trifluoroacetic acid (50 mL) followed by triethylsilane (50 mL). The reaction mixture was stirred at ambient temperature for 2 h and concentrated in vacuo. The residue was dissolved in ethyl acetate (250 mL), washed with saturated aqueous ammonium chloride (3×100 mL) and brine (3×100 mL), dried over anhydrous sodium sulfate, filtered and concentrated in vacuo. The residue was triturated with diethyl ether to afford 3-[6-(benzyloxy)-1,3-benzodioxol-5-yl]-1-(diphenylmethyl)-1,3-dihydro-2H-indol-2-one (19.0 g) as a colorless solid in 61% yield: $^1$H NMR (300 MHz, CDCl$_3$) δ7.31-7.23 (m, 15H), 7.10-6.88 (m, 4H), 6.50-6.45 (m, 3H), 5.86 (s, 2H), 4.97-4.86 (m, 3H); MS (ES+) m/z 525.9 (M+1).

B. Alternatively, to a solution of 3-[6-(benzyloxy)-1,3-benzodioxol-5-yl]-1-(diphenylmethyl)-3-hydroxy-1,3-dihydro-2H-indol-2-one (2.0 kg, 3.7 mol) in dichloromethane (7 L) at 20-30° C. was added trifluoracetic acid (2.5 L), followed by triethylsilane (3.1 L). The mixture was stirred at 15-35° C. for 4 h and concentrated in vacuo to dryness. To the residue was added ethyl acetate (16 L) and the mixture was stirred at 15-35° C. for 0.5 h, washed with saturated aqueous ammonium chloride (3×7 L) and brine (3×7 L) and concentrated in vacuo to a volume of approximately 7 L. Methyl tert-butyl ether (9 L) was added and the mixture concentrated in vacuo to a volume of approximately 9 L and stirred at 10-20° C. for 2.5 h, during which time a solid was deposited. The solid was collected by filtration, washed with methyl tert-butyl ether (0.4 L) and dried in vacuo at 50-55° C. for 7 h to afford 3-[6-(benzyloxy)-1,3-benzodioxol-5-yl]-1-(diphenylmethyl)-1,3-dihydro-2H-indol-2-one (1.26 kg) as an off-white solid in 65% yield: $^1$H NMR (300 MHz, CDCl$_3$) δ7.31-7.23 (m, 15H), 7.10-6.88 (m, 4H), 6.50-6.45 (m, 3H), 5.86 (s, 2H), 4.97-4.86 (m, 3H); MS (ES+) m/z 525.9 (M+1).

Example 13

Synthesis of (3S)-3-[6-(benzyloxy)-1,3-benzodioxol-5-yl]-3-[(benzyloxy)methyl]-1-(diphenylmethyl)-1,3-dihydro-2H-indol-2-one Compound of Formula (19a1)

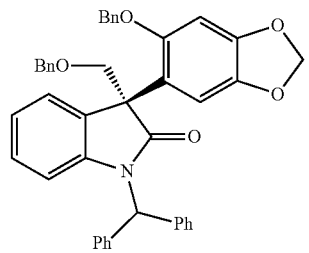 [SMILES: O=C1N(C(c2ccccc2)c2ccccc2)c2ccccc2[C@@]1(COCc1ccccc1)c1cc2c(cc1OCc1ccccc1)OCO2]

A. To a nitrogen-degassed mixture of 50% w/w aqueous potassium hydroxide (69.6 mL, 619 mmol), toluene (100 mL), and (9S)-1-(anthracen-9-ylmethyl)cinchonan-1-ium-9-ol chloride (0.50 g, 0.95 mmol) cooled in an ice/salt bath to an internal temperature of −18° C. was added a nitrogen-degassed solution of 3-[6-(benzyloxy)-1,3-benzodioxol-5-yl]-1-(diphenylmethyl)-1,3-dihydro-2H-indol-2-one (10.0 g, 19.0 mmol) and benzyl chloromethyl ether (2.9 mL, 21 mmol) in toluene/tetrahydrofuran (1:1 v/v, 80 mL) dropwise over 1 h. The reaction mixture was stirred for 3.5 h and diluted with ethyl acetate (80 mL). The organic phase was washed with 1 N hydrochloric acid (3×150 mL) and brine (2×100 mL), dried over anhydrous sodium sulfate, filtered and concentrated in vacuo to afford (3S)-3-[6-(benzyloxy)-1,3-benzodioxol-5-yl]-3-[(benzyloxy)methyl]-1-(diphenylmethyl)-1,3-dihydro-2H-indol-2-one (12.6 g) as a colorless solid in quantitative yield: $^1$H NMR (300 MHz, CDCl$_3$) δ7.42 (d, 2H), 7.24-6.91 (m, 21H), 6.69-6.67 (m, 2H), 6.46 (d, J=7.7 Hz, 1H), 6.15 (s, 1H), 5.83-5.81 (m, 2H), 4.53-4.31 (m, 3H), 4.17-4.09 (m, 3H); MS (ES+) m/z 646.0 (M+1); ee (enantiomeric excess) 90% (HPLC, Chiralpak IA, 2.5% acetonitrile in methyl tert-butyl ether).

B. Alternatively, a mixture of 50% w/v aqueous potassium hydroxide (4.2 kg), toluene (12 L) and (9S)-1-(anthracen-9-ylmethyl)cinchonan-1-ium-9-ol chloride (0.06 kg, 0.1 mol) was degassed with dry nitrogen and cooled to −18 to −22° C. To this mixture was added a cold (−18 to −22° C.), nitrogen-degassed solution of 3-[6-(benzyloxy)-1,3-benzodioxol-5-yl]-1-(diphenylmethyl)-1,3-dihydro-2H-indol-2-one (1.2 kg, 2.3 mol) and benzyl chloromethyl ether (0.43 kg, 2.8 mol) in toluene (10 L) and tetrahydrofuran (10 L) at −18 to 22° C. over 3 h. The mixture was stirred at −18 to −22° C. for 5 h, allowed to warm to ambient temperature and diluted with ethyl acetate (10 L). The phases were separated and the organic layer was washed with 1 N hydrochloric acid (3×18 L) and brine (2×12 L) and concentrated in vacuo to dryness to afford (3S)-3-[6-(benzyloxy)-1,3-benzodioxol-5-yl]-3-[(benzyloxy)methyl]-1-(diphenylmethyl)-1,3-dihydro-2H-indol-2-one (1.5 kg) as a colorless solid in quantitative yield: $^1$H NMR (300 MHz, CDCl$_3$) δ7.42 (d, 2H), 7.24-6.91 (m, 21H), 6.69-6.67 (m, 2H), 6.46 (d, J=7.7 Hz, 1H), 6.15 (s, 1H), 5.83-5.81 (m, 2H), 4.53-4.31 (m, 3H), 4.17-4.09 (m, 3H); MS (ES+) m/z 646.0 (M+1); ee (enantiomeric excess) 90% (HPLC, ChiralPak IA).

Example 14

Synthesis of (3S)-1-(diphenylmethyl)-3-(6-hydroxy-1,3-benzodioxol-5-yl)-3-(hydroxymethyl)-1,3-dihydro-2H-indol-2-one Compound of Formula (20a1)

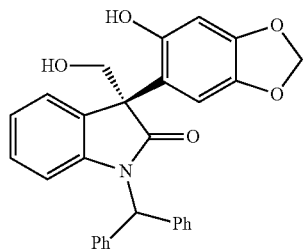 [SMILES: O=C1N(C(c2ccccc2)c2ccccc2)c2ccccc2[C@@]1(CO)c1cc2c(cc1O)OCO2]

A. A mixture of (3S)-3-[6-(benzyloxy)-1,3-benzodioxol-5-yl]-3-[(benzyloxy)methyl]-1-(diphenylmethyl)-1,3-dihydro-2H-indol-2-one (8.8 g, 14 mmol), 10% w/w palladium on carbon (50% wetted powder, 3.5 g, 1.6 mmol), and acetic acid (3.9 mL, 68 mmol) in a nitrogen-degassed mixture of ethanol/tetrahydrofuran (1:1 v/v, 140 mL) was stirred under hydrogen gas (1 atm) at ambient temperature for 4 h. The reaction mixture was filtered through a pad of diatomaceous earth and the pad was rinsed with ethyl acetate (100 mL). The filtrate was concentrated in vacuo to afford (3S)-1-(diphenylmethyl)-3-(6-hydroxy-1,3-benzodioxol-5-yl)-3-(hydroxymethyl)-1,3-dihydro-2H-indol-2-one as a colorless solid that was carried forward without further purification: $^1$H NMR (300 MHz, CDCl$_3$) δ9.81 (br s, 1H), 7.35-7.24 (m, 11H), 7.15-7.01 (m, 3H), 6.62 (s, 1H), 6.54-6.47 (m, 2H), 5.86-5.84 (m, 2H), 4.76 (d, J=11.0 Hz, 1H), 4.13-4.04 (m, 1H), 2.02 (s, 1H); MS (ES+) m/z 465.9 (M+1); ee (enantiomeric excess) 93% (HPLC, Chiralpak IA, 2.5% acetonitrile in methyl tert-butyl ether).

B. Alternatively, a glass-lined hydrogenation reactor was charged with (3S)-3-[6-(benzyloxy)-1,3-benzodioxol-5-yl]-3-[(benzyloxy)methyl]-1-(diphenylmethyl)-1,3-dihydro-2H-indol-2-one (0.1 kg, 0.15 mol), tetrahydrofuran (0.8 L), ethanol (0.4 L), acetic acid (0.02 L) and 20% w/w palladium (II) hydroxide on carbon (0.04 kg). The reactor was purged three times with nitrogen. The reactor was then purged three times with hydrogen and was then pressurized to 50-55 lb/in$^2$ with hydrogen. The mixture was stirred at 20-30° C. for 5 h under a 50-55 lb/in$^2$ atmosphere of hydrogen. The reactor was purged and the mixture was filtered. The filtrate was concentrated in vacuo to a volume of approximately 0.2 L and methyl tert-butyl ether (0.4 L) was added. The mixture was concentrated in vacuo to a volume of approximately 0.2 L and methyl tert-butyl ether (0.2 L) was added, followed by heptane (0.25 L). The mixture was stirred at ambient temperature for 2 h, during which time a solid was deposited. The solid was collected by filtration, washed with heptane (0.05 L) and dried in vacuo at a temperature below 50° C. for 8 h to afford (3S)-1-(diphenylmethyl)-3-(6-hydroxy-1,3-benzodioxol-5-yl)-3-(hydroxymethyl)-1,3-dihydro-2H-indol-2-one (0.09 kg) as a colorless solid in 95% yield: $^1$H NMR (300 MHz, CDCl$_3$) δ9.81 (br s, 1H), 7.35-7.24 (m, 11H), 7.15-7.01 (m, 3H), 6.62 (s, 1H), 6.54-6.47 (m, 2H), 5.86-5.84 (m, 2H), 4.76 (d, J=11.0 Hz, 1H), 4.13-4.04 (m, 1H), 2.02 (s, 1H); MS (ES+) m/z 465.9 (M+1); ee (enantiomeric excess) 91% (HPLC, ChiralPak IA).

Example 15

Synthesis of (7S)-1'-(diphenylmethyl)spiro[furo[2,3-f][1,3]benzodioxole-7,3'-indol]-2'(1'H)-one Compound of Formula (21a1)

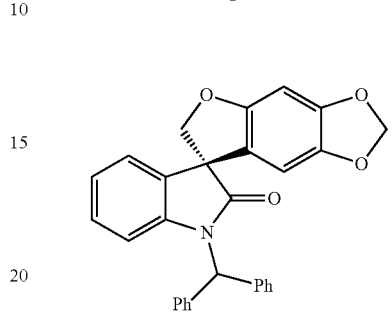

A. To a cooled (0° C.) solution of (3S)-1-(diphenylmethyl)-3-(6-hydroxy-1,3-benzodioxol-5-yl)-3-(hydroxymethyl)-1,3-dihydro-2H-indol-2-one prepared according to the procedure described in Example 14 (13.6 mmol) and 2-(diphenylphosphino)pyridine (4.3 g, 16 mmol) in anhydrous tetrahydrofuran (140 mL) was added di-tert-butylazodicarboxylate (3.8 g, 17 mmol). The reaction mixture was stirred at 0° C. for 3 h, diluted with ethyl acetate (140 mL), washed with 3 N hydrochloric acid (6×50 mL) and brine (2×100 mL), dried over anhydrous sodium sulfate, filtered and concentrated in vacuo. The residue was triturated with a mixture of diethyl ether and hexanes to afford (7S)-1'-(diphenylmethyl)spiro[furo[2,3-f][1,3]benzodioxole-7,3'-indol]-2'(1'H)-one (4.55 g) as a colorless solid in a 75% yield over 2 steps: $^1$H NMR (300 MHz, CDCl$_3$) δ7.34-7.24 (m, 10H), 7.15-7.13 (m, 1H), 7.04 (s, 1H), 6.99-6.95 (m, 2H), 6.50-6.48 (m, 2H), 6.06 (s, 1H), 5.85-5.83 (m, 2H), 4.96 (d, J=8.9 Hz, 1H), 4.69 (d, J=8.9 Hz, 1H); MS (ES+) m/z 447.9 (M+1); ee (enantiomeric excess) 93% (HPLC, Chiralpak IA, 2.5% acetonitrile in methyl tert-butyl ether).

B. Alternatively, to a cooled (0-5° C.) solution of (3S)-1-(diphenylmethyl)-3-(6-hydroxy-1,3-benzodioxol-5-yl)-3-(hydroxymethyl)-1,3-dihydro-2H-indol-2-one (1.0 kg, 2.1 mol) and 2-(diphenylphosphino)pyridine (0.66 kg, 2.5 mol) in anhydrous tetrahydrofuran (20 L) was added over 2 h a solution of di-tert-butylazodicarboxylate (0.62 kg, 2.7 mmol) in anhydrous tetrahydrofuran (5 L). The mixture was stirred for 4 h at 0-5° C. and was allowed to warm to ambient temperature. The mixture was diluted with ethyl acetate (20 L), washed with 3 N hydrochloric acid (6×8 L) and brine (2×12 L) and concentrated in vacuo to a volume of approximately 1.5 L. Methyl tert-butyl ether (4 L) was added and the mixture concentrated in vacuo to a volume of approximately 1.5 L. Methyl tert-butyl ether (2 L) and heptane (2 L) were added and the mixture was stirred at ambient temperature for 2 h, during which time a solid was deposited. The solid was collected by filtration, washed with heptane (0.5 L) and dried in vacuo below 50° C. for 8 h to afford (7S)-1'-(diphenylmethyl)spiro[furo[2,3-f][1,3]benzodioxole-7,3'-indol]-2'(1'H)-one (0.76 kg) as a colorless solid in 79% yield: $^1$H NMR (300 MHz, CDCl$_3$) δ7.34-7.24 (m, 10H), 7.15-7.13 (m, 1H), 7.04 (s, 1H), 6.99-6.95 (m, 2H), 6.50-6.48 (m, 2H), 6.06 (s, 1H), 5.85-5.83 (m, 2H), 4.96 (d, J=8.9 Hz, 1H), 4.69 (d, J=8.9 Hz, 1H); MS (ES+) m/z 447.9 (M+1); ee (enantiomeric excess) 92% (HPLC, ChiralPak IA).

Example 16

Synthesis of (7S)-spiro[furo[2,3-f][1,3]benzodioxole-7,3'-indol]-2'(1'H)-one

Compound of Formula (22a1)

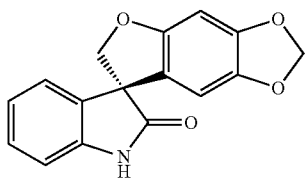 [SMILES: O=C1Nc2ccccc2[C@]12COc1cc3c(cc12)OCO3]

A. To a solution of (7S)-1'-(diphenylmethyl)spiro[furo[2,3-f][1,3]benzodioxole-7,3'-indol]-2'(1'H)-one (4.55 g, 10.2 mmol) in trifluoroacetic acid (80 mL) was added triethylsilane (7 mL). The reaction mixture was heated at reflux for 2.5 h, allowed to cool to ambient temperature and concentrated in vacuo. The residue was triturated with a mixture of diethyl ether and hexanes to afford (7S)-spiro[furo[2,3-f][1,3]benzodioxole-7,3'-indol]-2'(1'H)-one (2.30 g) as a colorless solid in 80% yield: $^1$H NMR (300 MHz, CDCl$_3$) δ8.27 (br s, 1H), 7.31-7.26 (m, 1H), 7.17-7.15 (m, 1H), 7.07-7.02 (m, 1H), 6.96-6.94 (m, 1H), 6.53-6.52 (m, 1H), 6.24-6.23 (m, 1H), 5.88-5.87 (m, 2H), 4.95 (d, J=8.6 Hz, 1H), 4.68 (d, J=8.9 Hz, 1H); MS (ES+) m/z 281.9 (M+1); ee (enantiomeric excess) 99% (HPLC, Chiralpak IA, 2.5% acetonitrile in methyl tert-butyl ether).

B. Alternatively, a mixture of (7S)-1'-(diphenylmethyl)spiro[furo[2,3-f][1,3]benzodioxole-7,3'-indol]-2'(1'H)-one (0.70 kg, 1.6 mol), trifluoroacetic acid (12 L) and triethylsilane (1.1 L) was heated at reflux under nitrogen atmosphere for 3 h, allowed to cool to ambient temperature and concentrated in vacuo to dryness. To the residue was added ethyl acetate (0.3 L), methyl tert-butyl ether (1 L) and heptane (3.5 L), causing a solid to be deposited. The solid was collected by filtration, taken up in dichloromethane (3 L), stirred at ambient temperature for 1 h and filtered. The filtrate was concentrated in vacuo to dryness. The residue was taken up in ethyl acetate (0.3 L), methyl tert-butyl ether (1 L) and heptane (3.5 L), causing a solid to be deposited. The solid was collected by filtration and dried in vacuo below 50° C. for 8 h to afford (7S)-spiro[furo[2,3-f][1,3]benzodioxole-7,3'-indol]-2'(1'H)-one (0.40 kg) as a colorless solid in 91% yield: $^1$H NMR (300 MHz, CDCl$_3$) δ8.27 (br s, 1H), 7.31-7.26 (m, 1H), 7.17-7.15 (m, 1H), 7.07-7.02 (m, 1H), 6.96-6.94 (m, 1H), 6.53-6.52 (m, 1H), 6.24-6.23 (m, 1H), 5.88-5.87 (m, 2H), 4.95 (d, J=8.6 Hz, 1H), 4.68 (d, J=8.9 Hz, 1H); MS (ES+) m/z 281.9 (M+1); ee (enantiomeric excess) 98.6% (HPLC, ChiralPak IA).

Example 17

Synthesis of (7S)-1'-{[5-(trifluoromethyl)furan-2-yl]methyl}spiro[furo[2,3-f][1,3]benzodioxole-7,3'-indol]-2° (1'H)-one Compound of Formula (Ia1)

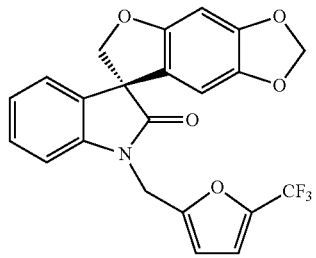 [SMILES: O=C1N(Cc2ccc(C(F)(F)F)o2)c2ccccc2[C@]12COc1cc3c(cc12)OCO3]

A. To a mixture of (7S)-6H-spiro[[1,3]dioxolo[4,5-f]benzofuran-7,3'-indolin]-2'-one (1.80 g, 6.41 mmol) and 2-(bromomethyl)-5-(trifluoromethyl)furan (1.47 g, 6.41 mmol) in acetone (200 mL) was added cesium carbonate (3.13 g, 9.61 mmol). The reaction mixture was heated at reflux for 2 h and filtered while hot through a pad of diatomaceous earth. The filtrate was concentrated in vacuo to afford (7S)-1'-{[5-(trifluoromethyl)furan-2-yl]methyl}spiro[furo[2,3-f][1,3]benzodioxole-7,3'-indol]-2'(1° H)-one (2.71 g) as a colorless solid in quantitative yield (97% purity by HPLC). The product was crystallized from a mixture of methanol and hexanes to afford (7S)-1'-{[5-(trifluoromethyl)furan-2-yl]methyl}spiro[furo[2,3-f][1,3]benzodioxole-7,3'-indol]-2' (1'H)-one (1.46 g) as colorless needles in 53% yield. The mother liquor was concentrated in vacuo and subjected to a second crystallization in methanol and hexanes to afford further (7S)-1'-{[5-(trifluoromethyl)furan-2-yl]methyl}spiro[furo[2,3-f][1,3]benzodioxole-7,3'-indol]-2' (1'H)-one (0.469 g) as a colorless solid in 17% yield (total yield 70%): $^1$H NMR (300 MHz, CDCl$_3$) δ 7.29-6.96 (m, 4H), 6.73 (s, 1H), 6.50 (s, 1H), 6.38 (s, 1H), 6.09 (s, 1H), 5.85 (br s, 2H), 5.06 (d, J=16.0 Hz, 1H), 4.93-4.84 (m, 2H), 4.68-4.65 (m, 1H); MS (ES+) m/z 429.8 (M+1); ee (enantiomeric excess) >99.5% (HPLC, Chiralpak IA, 2.5% acetonitrile in methyl tert-butyl ether).

B. Alternatively, to a solution of (7S)-spiro[furo[2,3-f][1,3]benzodioxole-7,3'-indol]-2'(1'H)-one (0.40 kg, 1.4 mol) in anhydrous N,N-dimethylformamide (5 L) was added cesium carbonate (1.2 kg, 3.4 mol), followed by 2-(bromomethyl)-5-(trifluoromethyl)furan (0.24 L, 1.7 mol). The mixture was heated at 80-85° C. for 3 h, allowed to cool to ambient temperature and filtered through a pad of diatomaceous earth. The pad was washed with ethyl acetate (8 L). The combined filtrate and washes were washed with water (4 L), saturated aqueous ammonium chloride (2×4 L) and brine (2×4 L) and concentrated in vacuo to dryness. The residue was purified by recrystallization from tert-butyl methyl ether (0.4 L) and heptane (0.8 L), followed by drying of the resultant solid in vacuo at 40-50° C. for 8 h to afford (7S)-1'-{[5-(trifluoromethyl)furan-2-yl]methyl}spiro[furo[2,3-f][1,3]benzodioxole-7,3'-indol]-2'(1'H)-one (0.37 kg) as a colorless solid in 61% yield: $^1$H NMR (300 MHz, CDCl$_3$) δ 7.29-6.96 (m, 4H), 6.73 (s, 1H), 6.50 (s, 1H), 6.38 (s, 1H), 6.09 (s, 1H), 5.85 (br s, 2H), 5.06 (d, J=16.0 Hz, 1H), 4.93-4.84 (m, 2H), 4.68-4.65 (m, 1H); MS (ES+) m/z 429.8 (M+1); ee (enantiomeric excess) >99% (HPLC, Chiralpak IA).

Example 18

Synthesis of 1-(diphenylmethyl)-3-hydroxy-3-(7-hydroxy-2,3-dihydro-1,4-benzodioxin-6-yl)-1,3-dihydro-2H-indol-2-one Compound of Formula (16a2)

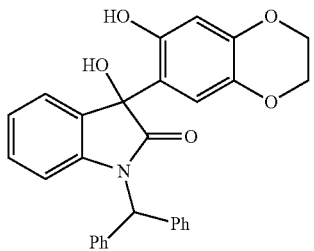 [SMILES: O=C1N(C(c2ccccc2)c2ccccc2)c2ccccc2C1(O)c1cc2c(cc1O)OCCO2]

To a cooled (0° C.) solution of 2,3-dihydro-1,4-benzodioxin-6-ol (54.0 g, 355 mmol) in tetrahydrofuran (600 mL) was added dropwise a 2 M solution of isopropylmagnesium chloride in tetrahydrofuran (178 mL, 356 mmol). The reaction mixture was stirred for at 0° C. for 45 min. and 1-(diphenylmethyl)-1H-indole-2,3-dione (85.8 g, 274 mmol) was added. The reaction mixture was stirred at 0° C. for 3 h, allowed to warm to ambient temperature and stirred for a further 16 h. The mixture was cooled to 0° C. and a mixture of 2,3-dihydro-1,4-benzodioxin-6-ol (54.0 g, 355 mmol), isopropylmagnesium chloride (2 M solution in tetrahydrofuran, 178 mL, 356 mmol) and tetrahydrofuran (600 mL) was added. The reaction was stirred at 0° C. for 2.5 h, allowed to warm to ambient temperature and stirred for a further 20 h. Water (250 mL) was added and the mixture was diluted with ethyl acetate (1000 mL), washed with saturated aqueous ammonium chloride (3×500 mL) and brine (3×500 mL), dried over anhydrous sodium sulfate, filtered and concentrated in vacuo. The residue was triturated with diethyl ether to afford 1-(diphenylmethyl)-3-hydroxy-3-(7-hydroxy-2,3-dihydro-1,4-benzodioxin-6-yl)-1,3-dihydro-2H-indol-2-one (117 g) as a colorless solid in 92% yield: $^1$H NMR (300 MHz, CDCl$_3$) δ8.94 (br s, 1H), 7.47-7.44 (m, 1H), 7.31-7.19 (m, 10H), 7.10-7.07 (m, 2H), 6.89 (s, 1H), 6.60-6.59 (m, 1H), 6.47-6.44 (m, 1H), 6.38-6.37 (m, 1H), 4.35 (s, 1H), 4.20-4.19 (m, 2H), 4.14-4.13 (m, 2H); MS (ES+) m/z 447.8 (M−17).

Example 19

Synthesis of 3-[7-(benzyloxy)-2,3-dihydro-1,4-benzodioxin-6-yl]-1-(diphenylmethyl)-3-hydroxy-1,3-dihydro-2H-indol-2-one Compound of Formula (17a2)

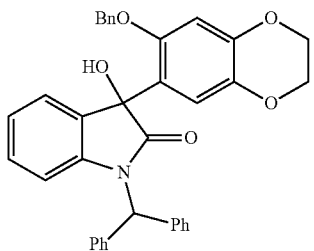 [SMILES: O=C1N(C(c2ccccc2)c2ccccc2)c2ccccc2C1(O)c1cc2c(cc1OCc1ccccc1)OCCO2]

To a mixture of 1-(diphenylmethyl)-3-hydroxy-3-(7-hydroxy-2,3-dihydro-1,4-benzodioxin-6-yl)-1,3-dihydro-2H-indol-2-one (70 g, 150 mmol) and potassium carbonate (41.6 g, 301 mmol) in anhydrous N,N-dimethylformamide (420 mL) was added benzyl chloride (26 mL, 230 mmol). The reaction mixture was heated at 50° C. for 4.5 h, allowed to cool to ambient temperature and poured into ice-water (2.5 L), causing a precipitate to be deposited. The solid was collected by suction filtration, washed with water (2 L) and triturated with a mixture of diethyl ether and hexanes to afford 3-[7-(benzyloxy)-2,3-dihydro-1,4-benzodioxin-6-yl]-1-(diphenylmethyl)-3-hydroxy-1,3-dihydro-2H-indol-2-one (73.2 g) as a colorless solid in 87% yield: $^1$H NMR (300 MHz, CDCl$_3$) δ7.35-7.13 (m, 16H), 7.06-6.88 (m, 4H), 6.46 (d, 1H), 6.23 (s, 1H), 4.69 (d, J=13.9 Hz, 1H), 4.55 (d, J=14.4 Hz, 1H), 4.16 (s, 4H), 3.58 (s, 1H); MS (ES+) m/z 537.8 (M−17).

Example 20

Synthesis of 3-[7-(benzyloxy)-2,3-dihydro-1,4-benzodioxin-6-yl]-1-(diphenylmethyl)-1,3-dihydro-2H-indol-2-one Compound of Formula (18a2)

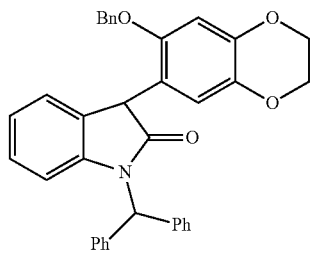 [SMILES: O=C1C(c2cc3c(cc2OCc2ccccc2)OCCO3)c2ccccc2N1C(c1ccccc1)c1ccccc1]

To a cooled (0° C.) solution of 3-[7-(benzyloxy)-2,3-dihydro-1,4-benzodioxin-6-yl]-1-(diphenylmethyl)-3-hydroxy-1,3-dihydro-2H-indol-2-one (72.8 g, 130 mmol) in dichloromethane (100 mL) was added trifluoroacetic acid (100 mL) and triethylsilane (104 mL). The reaction mixture was allowed to warm to ambient temperature, stirred for 16 h and concentrated in vacuo. The residue was taken up in a biphasic mixture of ethyl acetate (500 mL) and saturated aqueous ammonium chloride (200 mL), causing a precipitate to be deposited. The solid was collected by suction filtration and washed with ethyl acetate (100 mL) and water (100 mL) to afford 3-[7-(benzyloxy)-2,3-dihydro-1,4-benzodioxin-6-yl]-1-(diphenylmethyl)-1,3-dihydro-2H-indol-2-one (38.4 g) as a colorless solid in 55% yield. The filtrates were combined and the phases were separated. The organic phase was washed with saturated aqueous ammonium chloride (200 mL) and brine (2×200 mL), dried over anhydrous sodium sulfate, filtered and concentrated in vacuo. The residue was triturated with diethyl ether to afford a further amount of 3-[7-(benzyloxy)-2,3-dihydro-1,4-benzodioxin-6-yl]-1-(diphenylmethyl)-1,3-dihydro-2H-indol-2-one (14.7 g) as a colorless solid in 21% yield: $^1$H NMR (300 MHz, DMSO-d$_6$) δ7.34-7.19 (m, 15H), 7.09-7.03 (m, 1H), 6.94-6.90 (m, 4H), 6.52-6.49 (m, 2H), 4.97-4.79 (m, 3H), 4.17 (s, 4H); MS (ES+) m/z 539.9 (M+1).

Example 21

Synthesis of (3S)-3-[7-(benzyloxy)-2,3-dihydro-1,4-benzodioxin-6-yl]-3-[(benzyloxy)methyl]-1-(diphenylmethyl)-1,3-dihydro-2H-indol-2-one Compound of Formula (19a2)

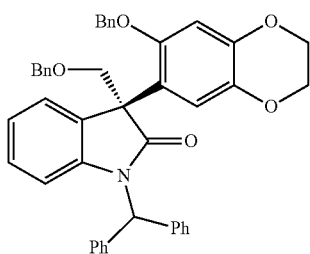 [SMILES: O=C1N(C(c2ccccc2)c2ccccc2)c2ccccc2[C@@]1(COCc1ccccc1)c1cc2c(cc1OCc1ccccc1)OCCO2]

To a nitrogen-degassed mixture of 50% w/w aqueous potassium hydroxide (68.4 mL, 609 mmol), toluene (650 mL), and (9S)-1-(anthracen-9-ylmethyl)cinchonan-1-ium-9-ol chloride (0.48 g, 0.92 mmol) cooled in an ice/salt bath to an internal temperature of −16° C. was added dropwise over 45 minutes a mixture of 3-[7-(benzyloxy)-2,3-dihydro-1,4-benzodioxin-6-yl]-1-(diphenylmethyl)-1,3-dihydro-2H-indol-2-one (10.1 g, 18.7 mmol), benzyl chloromethyl ether (2.5 mL, 18 mmol) and ethyl acetate (750 mL). The mixture was stirred for 1 h at −16° C. and a further portion of benzyl chloromethyl ether (0.7 mL, 5 mmol) was added. The mixture was stirred at −16° C. for a further 3 h and 1 N hydrochloric acid (250 mL) was added. The organic phase was washed with 1 N hydrochloric acid (3×300 mL) and brine (3×300 mL), dried over anhydrous sodium sulfate, filtered and concentrated in vacuo. The residue was triturated with diethyl ether to afford (3S)-3-[7-(benzyloxy)-2,3-dihydro-1,4-benzodioxin-6-yl]-3-[(benzyloxy)methyl]-1-(diphenylmethyl)-1,3-dihydro-2H-indol-2-one (9.74 g) as a beige solid in 79% yield: $^1$H NMR (300 MHz, CDCl$_3$) δ7.44 (d, J=7.2 Hz, 2H), 7.24-6.91 (m, 21H), 6.66 (br s, 2H), 6.46 (d, J=7.6 Hz, 1H), 6.09 (s, 1H), 4.51 (d, J=12.3 Hz, 1H), 4.42-4.37 (m, 2H), 4.21-4.12 (m, 7H); MS (ES+) m/z 659.8 (M+1); ee (enantiomeric excess) >99.5% (HPLC, Chiralpak IA, 2.5% acetonitrile in methyl tert-butyl ether).

Example 22

Synthesis of (3S)-1-(diphenylmethyl)-3-(7-hydroxy-2,3-dihydro-1,4-benzodioxin-6-yl)-3-(hydroxymethyl)-1,3-dihydro-2H-indol-2-one Compound of Formula (20a2)

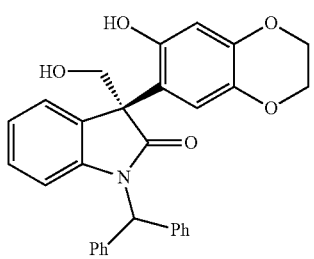 [SMILES: O=C1N(C(c2ccccc2)c2ccccc2)c2ccccc2[C@@]1(CO)c1cc2c(cc1O)OCCO2]

To a solution of (3S)-3-[7-(benzyloxy)-2,3-dihydro-1,4-benzodioxin-6-yl]-3-[(benzyloxy)methyl]-1-(diphenylmethyl)-1,3-dihydro-2H-indol-2-one (9.74 g, 14.8 mmol) in nitrogen-degassed tetrahydrofuran (100 mL) was added 10% w/w palladium on carbon (60% wetted powder, 4.50 g, 2.54 mmol). The reaction mixture was shaken in a Parr apparatus under a hydrogen atmosphere (10 lb/in$^2$ gauge) for 16 h and filtered through a pad of diatomaceous earth. The pad was rinsed with ethyl acetate (200 mL) and the filtrate was concentrated in vacuo. The residue was triturated with diethyl ether (100 mL) to afford (3S)-1-(diphenylmethyl)-3-(7-hydroxy-2,3-dihydro-1,4-benzodioxin-6-yl)-3-(hydroxymethyl)-1,3-dihydro-2H-indol-2-one (6.70 g) as a colorless solid in 95% yield: $^1$H NMR (300 MHz, CDCl$_3$) δ9.00 (br s, 1H), 7.34 (br s, 9H), 6.98-6.81 (m, 5H), 6.24-6.22 (m, 2H), 5.13 (br s, 1H), 4.18 (s, 5H), 3.94-3.91 (m, 1H), 2.51 (s, 1H); MS (ES+) m/z 479.9 (M+1); ee (enantiomeric excess) >99.5% (HPLC, Chiralpak IA, 2.5% acetonitrile in methyl tert-butyl ether).

Example 23

Synthesis of (8S)-1'-(diphenylmethyl)-2,3-dihydrospiro[furo[2,3-g][1,4]benzodioxine-8,3'-indol]-2'(1'H)-one Compound of Formula (21a2)

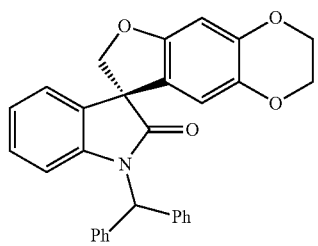 [SMILES: O=C1N(C(c2ccccc2)c2ccccc2)c2ccccc2[C@]12COc1cc3c(cc12)OCCO3]

To a cooled (0° C.) solution of (3S)-1-(diphenylmethyl)-3-(7-hydroxy-2,3-dihydro-1,4-benzodioxin-6-yl)-3-(hydroxymethyl)-1,3-dihydro-2H-indol-2-one (6.3 g, 14 mmol) in tetrahydrofuran (100 mL) was added 2-(diphenylphosphino)pyridine (3.98 g, 15.1 mmol) followed after 5 minutes by diisopropylazodicarboxylate (3.05 g, 15.1 mmol). The reaction mixture was stirred for 0.5 h at 0° C. and was concentrated in vacuo. The residue was taken up in ethyl acetate (200 mL), washed with 3 N hydrochloric acid (3×100 mL) and brine (3×100 mL), dried over anhydrous sodium sulfate, filtered and concentrated in vacuo. The residue was stirred in a mixture of tetrahydrofuran (100 mL) and 3 N aqueous sodium hydroxide (100 mL) at ambient temperature for 1 h and was then diluted with ethyl acetate (100 mL). The organic phase was separated, washed with brine (3×100 mL), dried over anhydrous sodium sulfate, filtered and concentrated in vacuo. The residue was triturated in diethyl ether to afford (8S)-1'-(diphenylmethyl)-2,3-dihydrospiro[furo[2,3-g][1,4]benzodioxine-8,3'-indol]-2' (1'H)-one (5.13 g) as a colorless solid in 85% yield: $^1$H NMR (300 MHz, CDCl$_3$) δ 7.45-7.26 (m, 10H), 7.20 (d, J=7.2 Hz, 1H), 7.13-7.08 (m, 1H), 7.02-6.97 (m, 1H), 6.90 (s, 1H), 6.59-6.53 (m, 2H), 6.03 (s, 1H), 4.86 (d, J=9.3 Hz, 1H), 4.73 (d, J=9.4 Hz, 1H), 4.18-4.11 (m, 4H); MS (ES+) m/z 461.9 (M+1).

Example 24

Synthesis of (8S)-2,3-dihydrospiro[furo[2,3-g][1,4]benzodioxine-8,3'-indol]-2'(1'H)-one Compound of Formula (22a2)

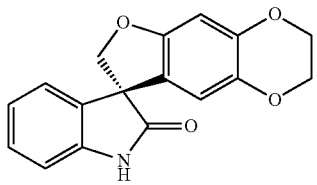 [SMILES: O=C1Nc2ccccc2[C@]12COc1cc3c(cc12)OCCO3]

To a solution of (8S)-1'-(diphenylmethyl)-2,3-dihydrospiro[furo[2,3-g][1,4]benzodioxine-8,3'-indol]-2'(1'H)-one (5.13 g, 11.1 mmol) in trifluoroacetic acid (17 mL) was added triethylsilane (8.9 mL). The reaction mixture was heated at reflux for 5 h, allowed to cool to ambient temperature and concentrated in vacuo. The residue was triturated with diethyl ether to afford (8S)-2,3-dihydrospiro[furo[2,3-g][1,4]benzodioxine-8,3'-indol]-2'(1'H)-one (2.7 g) as a beige solid in 82% yield: $^1$H NMR (300 MHz, CDCl$_3$) δ8.78 (s, 1H), 7.27-7.22 (m, 1H), 7.15 (d, J=7.1 Hz, 1H), 7.06-7.01 (m, 1H), 6.94 (d, J=7.6 Hz, 1H), 6.51 (br s, 1H), 6.32 (br s, 1H), 4.92 (d, J=9.0 Hz, 1H), 4.65 (d, J=9.0 Hz, 1H), 4.20-4.12 (m, 4H); MS (ES+) m/z 295.9 (M+1); ee (enantiomeric excess) >99.5% (HPLC, Chiralpak IA, 2.5% acetonitrile in methyl tert-butyl ether).

Example 25

Synthesis of (8S)-1'-{[3-(trifluoromethyl)pyridin-2-yl]methyl}-2,3-dihydrospiro[furo[2,3-g][1,4]benzodioxine-8,3'-indol]-2'(1'H)-one Compound of Formula (Ia2)

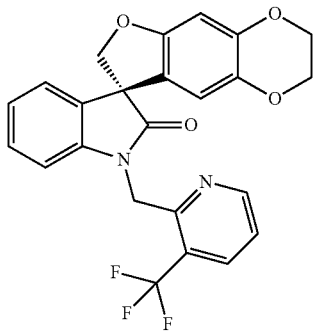 [SMILES: O=C1N(Cc2ncccc2C(F)(F)F)c2ccccc2[C@]12COc1cc3c(cc12)OCCO3]

To a solution of (8S)-2,3-dihydrospiro[furo[2,3-g][1,4]benzodioxine-8,3'-indol]-2'(1'H)-one (2.58 g, 8.7 mmol) in 1,4-dioxane (100 mL) was added cesium carbonate (7.12 g, 21.9 mmol) and 2-(bromomethyl)-3-(trifluoromethyl)pyridine (3.08 g, 9.60 mmol). The mixture was heated at reflux for 3 h, allowed to cool to ambient temperature and stirred for a further 16 h. The mixture was filtered through a pad of diatomaceous earth and the pad was rinsed with ethyl acetate (200 mL). The filtrate was concentrated in vacuo and the residue was triturated with a mixture of hexanes and diethyl ether to afford (8S)-1'-{[3-(trifluoromethyl)pyridin-2-yl]methyl}-2,3-dihydrospiro[furo[2,3-g][1,4]benzodioxine-8,3'-indol]-2'(1'H)-one (3.08 g) as a beige solid in 77% yield: $^1$H NMR (300 MHz, CDCl$_3$) δ8.64-8.62 (m, 1H), 7.96 (d, J=7.7 Hz, 1H), 7.32-7.12 (m, 3H), 7.02-6.97 (m, 1H), 6.61-6.58 (m, 2H), 6.48-6.47 (m, 1H), 5.40 (d, J=17.4 Hz, 1H), 5.12 (d, J=17.4 Hz, 1H), 5.00-4.96 (m, 1H), 4.73-4.70 (m, 1H), 4.18-4.11 (m, 4H); MS (ES+) m/z 454.9 (M+1); ee (enantiomeric excess) >99.5% (HPLC, Chiralpak IA, 2.5% acetonitrile in methyl tert-butyl ether).

All of the U.S. patents, U.S. patent application publications, U.S. patent applications, PCT published patent applications, foreign patents, foreign patent applications and non-patent publications referred to in this specification are incorporated herein by reference in their entirety.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of preparing a compound of formula (I):

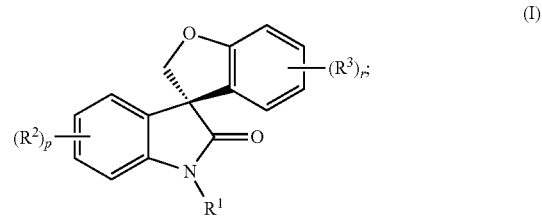

as an isolated (S)-enantiomer, or a non-racemic mixture of enantiomers having an enantiomeric excess of the (S)-enantiomer of greater than 80%, or a pharmaceutically acceptable salt thereof;

wherein:

p and r are each independently 1, 2, 3 or 4;

$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —$R^8$—C(O)N($R^4$)$R^5$, —S(O)$_2$—$R^5$, —$R^9$—S(O)$_m$—$R^5$ (where m is 0, 1 or 2), —$R^8$—O$R^5$, —$R^8$—CN, —$R^9$—P(O)(O$R^5$)$_2$, or —$R^9$—O—$R^9$—O$R^5$;

or $R^1$ is aralkyl substituted by —C(O)N($R^6$)$R^7$ where:

$R^6$ is hydrogen, alkyl, aryl or aralkyl; and $R^7$ is hydrogen, alkyl, haloalkyl, —$R^9$—CN, —$R^9$—O$R^5$, —$R^9$—N($R^4$)$R^5$, aryl, aralkyl, cycloalkyl, cycloalkylalkyl, heterocyclyl, heterocyclylalkyl, heteroaryl or heteroarylalkyl;

or $R^6$ and $R^7$, together with the nitrogen to which they are attached, form a N-heterocyclyl or a N-heteroaryl;

and wherein each aryl, aralkyl, cycloalkyl, cycloalkylalkyl, heterocyclyl, heterocyclylalkyl, heteroaryl and heteroarylalkyl groups for $R^6$ and $R^7$ may be optionally substituted by one or more substituents selected from the group consisting of alkyl, cycloalkyl, aryl, aralkyl, halo, haloalkyl, —$R^8$—CN, —$R^8$—O$R^5$, heterocyclyl and heteroaryl;

or $R^1$ is aralkyl optionally substituted by one or more substituents selected from the group consisting of —$R^8$—$OR^5$, —$C(O)OR^5$, halo, haloalkyl, alkyl, nitro, cyano, aryl, aralkyl, heterocyclyl and heteroaryl;

or $R^1$ is —$R^9$—$N(R^{10})R^{11}$, —$R^9$—$N(R^{12})C(O)R^{11}$ or —$R^9$—$N(R^{10})C(O)N(R^{10})R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—$OC(O)R^5$, —$R^9$—$C(O)OR^5$, —$R^9$—$C(O)N(R^4)R^5$, —$R^9$—$C(O)R^5$, —$R^9$—$N(R^4)R^5$, —$R^9$—$OR^5$, or —$R^9$—$CN$; and $R^{12}$ is hydrogen, alkyl, aryl, aralkyl or —$C(O)R^5$;

and wherein each aryl, aralkyl, cycloalkyl, cycloalkylalkyl, heterocyclyl, heterocyclylalkyl, heteroaryl and heteroarylalkyl for $R^{10}$ and $R^{11}$ may be optionally substituted by one or more substituents selected from the group consisting of alkyl, cycloalkyl, aryl, aralkyl, halo, haloalkyl, nitro, —$R^8$—$CN$, —$R^8$—$OR^5$, —$R^8$—$C(O)R^5$, heterocyclyl and heteroaryl;

or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—$OR^5$, —$R^8$—$C(O)OR^5$, —$R^8$—$N(R^4)R^5$, —$R^8$—$C(O)N(R^4)R^5$, —$R^8$—$N(R^5)C(O)R^4$, —$R^8$—$S(O)_m R^4$ (where m is 0, 1 or 2), —$R^8$—$CN$, or —$R^8$—$NO_2$;

each $R^2$ is independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$CN$, —$R^8$—$NO_2$, —$R^8$—$OR^5$, —$R^8$—$N(R^4)R^5$, —$N$=$C(R^4)R^5$, —$S(O)_m R^4$, —$OS(O)_2 CF_3$, —$R^8$—$C(O)R^4$, —$C(S)R^4$, —$C(R^4)_2 C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_n R^4$, —$N(R^5)S(O)_n N(R^4)R^5$, —$R^8$—$S(O)_n N(R^4)R^5$, —$N(R^5)C(=NR^5)N(R^4)R^5$, and —$N(R^5)C(=N-CN)N(R^4)R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^2$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$CN$, —$R^8$—$NO_2$, —$R^8$—$OR^5$, —$R^8$—$N(R^4)R^5$, —$S(O)_m R^4$, —$R^8$—$S(O)_n N(R^4)R^5$, —$R^8$—$C(O)R^4$, —$R^8$—$C(O)OR^4$, —$R^8$—$C(O)N(R^4)R^5$, —$N(R^5)C(O)R^4$, and —$N(R^5)S(O)_n R^4$, wherein each m is independently 0, 1, or 2 and each n is independently 1 or 2;

or any two adjacent $R^2$'s, together with the adjacent carbon ring atoms to which they are directly attached, may form a fused ring selected from cycloalkyl, aryl, heterocyclyl and heteroaryl, and the other $R^2$'s, if present, are as defined above;

each $R^3$ is independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$CN$, —$R^8$—$NO_2$, —$R^8$—$OR^5$, —$R^8$—$N(R^4)R^5$, —$N$=$C(R^4)R^5$, —$S(O)_m R^4$, —$OS(O)_2 CF_3$, —$R^8$—$C(O)R^4$, —$C(S)R^4$, —$C(R^4)_2 C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_n R^4$, —$N(R^5)S(O)_n N(R^4)R^5$, —$R^8$—$S(O)_n N(R^4)R^5$, —$N(R^5)C(=NR^5)N(R^4)R^5$, and —$N(R^5)C(N$=$C(R^4)R^5)N(R^4)R^5$, wherein each m is independently 0, 1, or 2 and each n is independently 1 or 2;

or any two adjacent $R^3$'s, together with the adjacent carbon ring atoms to which they are directly attached, may form a fused ring selected from cycloalkyl, heterocyclyl, aryl or heteroaryl, and the other $R^3$'s, if present, are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a N-heterocyclyl or a N-heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain;

wherein the method comprises:

(a) treating a compound of formula (9):

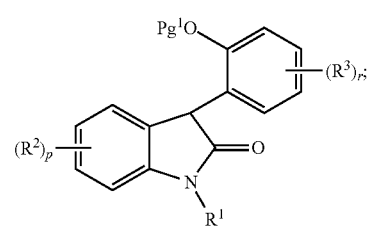

(9)

where p, r, $R^1$, $R^2$ and $R^3$ are as defined above for the compound of formula (I) and $Pg^1$ is an oxygen protecting group, as a racemic mixture of enantiomers or as a non-racemic mixture of enantiomers, or a pharmaceutically acceptable salt thereof, with a compound of formula (10):

(10)

where $Pg^2$ is an oxygen protecting group and X is halo, under suitable C-alkylation conditions comprising the presence of a phase transfer catalyst selected from a quaternary ammonium salt of quinidine or a quaternary ammonium salt of cinchonine to provide a compound of formula (11):

(11)

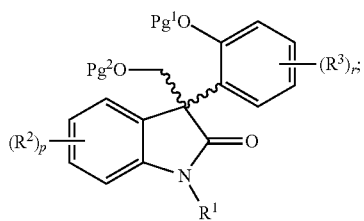

where p, r, R¹, R² and R³ are each as defined above for the compound of formula (I) and Pg¹ and Pg² are each independently an oxygen protecting group, as a racemic mixture of enantiomers or as a non-racemic mixture of enantiomers, or a pharmaceutically acceptable salt thereof;

(b) treating the compound of formula (11) under suitable recrystallization conditions to provide a compound of formula (12):

(12)

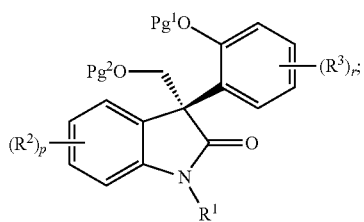

where p, r, R¹, R² and R³ are as defined above for the compounds of formula (I) and Pg¹ and Pg² are each independently an oxygen protecting group, as an isolated (S)-enantiomer or a non-racemic mixture of enantiomers having an enantiomeric excess of the (S)-enantiomer of greater than 80%, or a pharmaceutically acceptable salt thereof;

(g) treating the compound of formula (12) under suitable deprotecting conditions to provide a compound of formula (13):

(13)

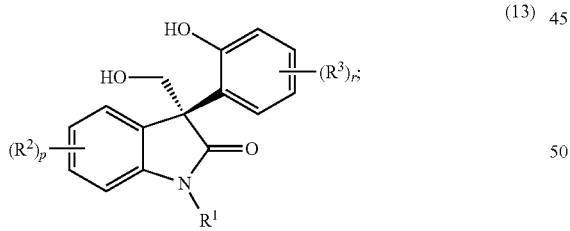

where p, r, R¹, R² and R³ are as defined above for the compounds of formula (I), as an isolated (S)-enantiomer or a non-racemic mixture of enantiomers having an enantiomeric excess of the (S)-enantiomer of greater than 80%, or a pharmaceutically acceptable salt thereof;

(h) treating the compound of formula (13) under suitable Mitsunobu reaction conditions to provide the compound of formula (I), as defined above, as an isolated (S)-enantiomer or a non-racemic mixture of enantiomers having an enantiomeric excess of the (S)-enantiomer of greater than 80%, or a pharmaceutically acceptable salt thereof.

2. The method of claim 1 wherein the compound of formula (I) is a compound of formula (Ia):

(Ia)

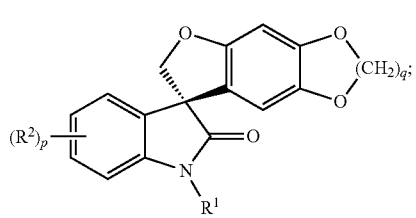

where q is 1 or 2 and p, R¹ and R² are each as defined above in claim 1 for the compounds of formula (I), as an isolated (S)-enantiomer or a non-racemic mixture of enantiomers having an enantiomeric excess of the (S)-enantiomer of greater than 80%, or a pharmaceutically acceptable salt thereof.

3. The method of claim 2 wherein the compound of formula (Ia) is a compound of formula (Ia1):

(Ia1)

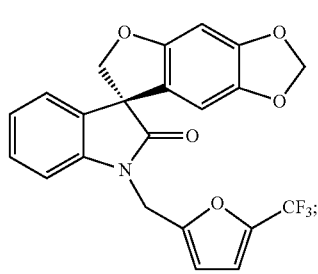

as an isolated (S)-enantiomer or a non-racemic mixture of enantiomers having an enantiomeric excess of the (S)-enantiomer of greater than 80%, or a pharmaceutically acceptable salt thereof.

4. The method of claim 1 wherein the compound of formula (13) is a compound of formula (13a):

(13a)

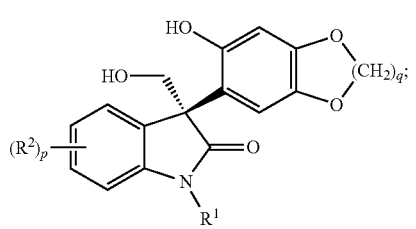

where q is 1 or 2 and p, R¹ and R² are each as defined above in claim 1 for the compounds of formula (I), as an isolated (S)-enantiomer or a non-racemic mixture of enantiomers having an enantiomeric excess of the (S)-enantiomer of greater than 80%, or a pharmaceutically acceptable salt thereof.

5. The method of claim 4 wherein the compound of formula (13a) is a compound of formula (13a1):

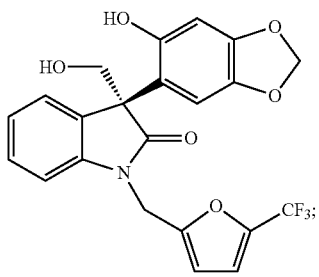

(13a1)

as an isolated (S)-enantiomer or a non-racemic mixture of enantiomers having an enantiomeric excess of the (S)-enantiomer of greater than 80%, or a pharmaceutically acceptable salt thereof.

6. The method of claim 1 wherein the compound of formula (12) is a compound of formula (12a):

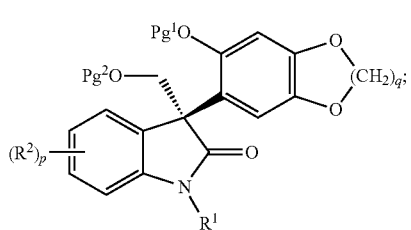

(12a)

where q is 1 or 2, $Pg^1$ and $Pg^2$ are each independently an oxygen protecting group and p, $R^1$ and $R^2$ are each as defined above in claim 1 for the compounds of formula (I), as an isolated (S)-enantiomer or a non-racemic mixture of enantiomers having an enantiomeric excess of the (S)-enantiomer of greater than 80%, or a pharmaceutically acceptable salt thereof.

7. The method of claim 6 wherein the compound of formula (I2a) is a compound of formula (12a1):

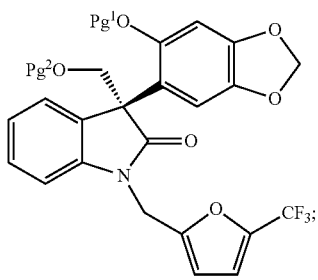

(12a1)

where $Pg^1$ and $Pg^2$ are each independently an oxygen protecting group, as an isolated (S)-enantiomer or a non-racemic mixture of enantiomers having an enantiomeric excess of the (S)-enantiomer of greater than 80%, or a pharmaceutically acceptable salt thereof.

8. The method of claim 1 wherein the compound of formula (11) is a compound of formula (11a):

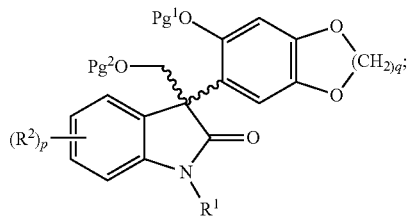

(11a)

where q is 1 or 2 and p, $R^1$ and $R^2$ are each as defined above in claim 1 for the compounds of formula (I) and $Pg^1$ and $Pg^2$ are each independently an oxygen protecting group, as a racemic mixture of enantiomers or as a non-racemic mixture of enantiomers, or a pharmaceutically acceptable salt thereof.

9. The method of claim 8 wherein the compound of formula (11a) is a compound of formula (11a1):

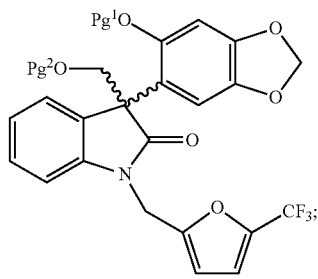

(11a1)

where $Pg^1$ and $Pg^2$ are each independently an oxygen protecting group, as a racemic mixture of enantiomers or as a non-racemic mixture of enantiomers, or a pharmaceutically acceptable salt thereof.

10. The method of claim 1 wherein the compound of formula (9) is a compound of formula (9a):

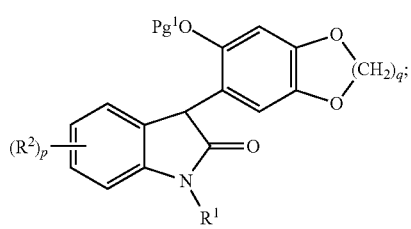

(9a)

where q is 1 or 2 and p, $R^1$ and $R^2$ are each as defined above in claim 1 for the compounds of formula (I) and $Pg^1$ is an oxygen protecting group, as a racemic mixture of enantiomers or as a non-racemic mixture of enantiomers, or a pharmaceutically acceptable salt thereof.

11. The method of claim 10 wherein the compound of formula (9a) is a compound of formula (9a1):

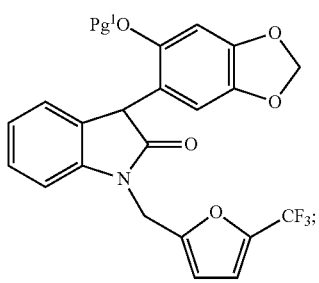

(9a1)

where Pg$^1$ is an oxygen protecting group, as a racemic mixture of enantiomers or as a non-racemic mixture of enantiomers, or a pharmaceutically acceptable salt thereof.

12. The method of claim 1 further comprising a dehydoxylation step prior to treating the compound of formula (9) with a compound of formula (10), wherein the dehydroxylation step comprises treating a compound of formula (8):

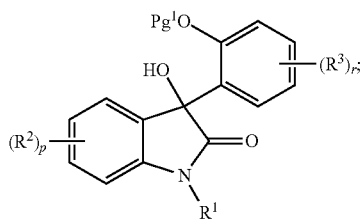

(8)

where p, r, R$^1$, R$^2$ and R$^3$ are each defined above in claim 1 for the compounds of formula (I) and Pg$^1$ is an oxygen protecting group, as a racemic mixture of enantiomers or as a non-racemic mixture of enantiomers, or a pharmaceutically acceptable salt thereof, under suitable dehydroxylation conditions to provide a compound of formula (9), as described above.

13. The method of claim 12 wherein the compound of formula (8) is a compound of formula (8a):

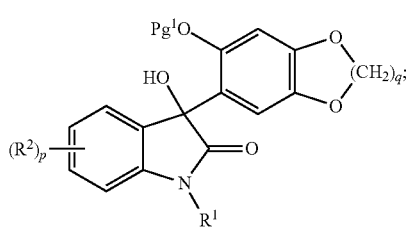

(8a)

where q is 1 or 2, p, R$^1$ and R$^2$ are each as defined above in claim 1 for the compounds of formula (I) and Pg$^1$ is an oxygen protecting group, as a racemic mixture of enantiomers or as a non-racemic mixture of enantiomers, or a pharmaceutically acceptable salt thereof.

14. The method of claim 13 wherein the compound of formula (8a) is a compound of formula (8a1):

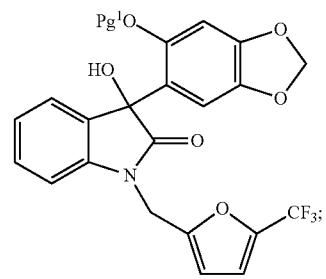

(8a1)

where Pg$^1$ is an oxygen protecting group, as a racemic mixture of enantiomers or as a non-racemic mixture of enantiomers, or a pharmaceutically acceptable salt thereof.

15. The method of claim 12 further comprising a protecting step prior to treating the compound of formula (8) under suitable dehydroxylation conditions, wherein the protecting step comprises treating a compound of formula (6):

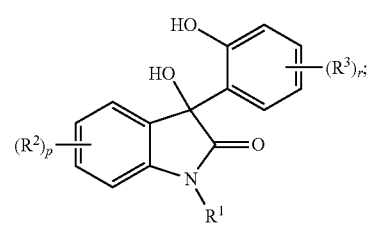

(6)

where p, r, R$^1$, R$^2$, and R$^3$ are each as defined above in claim 1 for the compounds of formula (I), as a racemic mixture of enantiomers or as a non-racemic mixture of enantiomers, or a pharmaceutically acceptable salt thereof, with a compound of formula (7):

Pg$^1$X (7);

where X is halo and Pg$^1$ is an oxygen protecting group under suitable protecting conditions to provide a compound of formula (8), as described above.

16. The method of claim 15 wherein the compound of formula (6) is a compound of formula (6a):

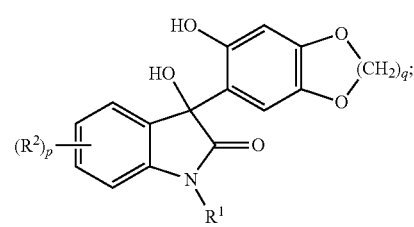

(6a)

where q is 1 or 2 and p, R$^1$ and R$^2$ are each as defined above in claim 1 for the compounds of formula (I), as a racemic mixture of enantiomers or as a non-racemic mixture of enantiomers, or a pharmaceutically acceptable salt thereof.

17. The method of claim 16 wherein the compound of formula (6a) is a compound of formula (6a1):

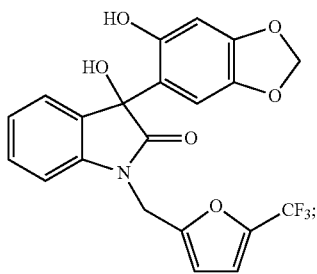
(6a1)

as a racemic mixture of enantiomers or as a non-racemic mixture of enantiomers, or a pharmaceutically acceptable salt thereof.

18. The method of claim 15 further comprising a Grignard addition step prior to treating the compound of formula (6) with a compound of formula (7), wherein the Grignard addition step comprises the following substeps:
(a) treating a compound of formula (4):

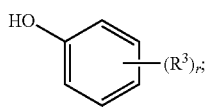
(4)

where r and $R^3$ are as described above for the compound of formula (I), with a Grignard reagent of formula (5):

RMgX    (5);

where X is iodo, bromo or chloro and R is alkyl, under suitable conditions to form an intermediate Grignard addition product;
(b) treating a compound of formula (3):

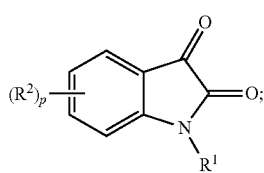
(3)

where p, $R^1$, $R^2$ are each as defined above in claim 1 for the compounds of formula (I), or a pharmaceutically acceptable salt thereof, with the intermediate Grignard addition product formed in substep a) above under suitable Grignard reaction conditions to provide a compound of formula (6), as described above.

19. The method of claim 18 wherein the compound of formula (3) is a compound of formula (3a):

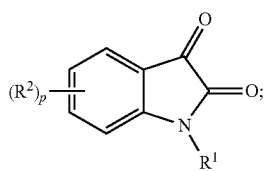
(3a)

where p, $R^1$ and $R^2$ are each as defined above in claim 1 for the compounds of formula (I), or a pharmaceutically acceptable salt thereof.

20. The method of claim 19 wherein the compound of formula (3a) is a compound of formula (3a1):

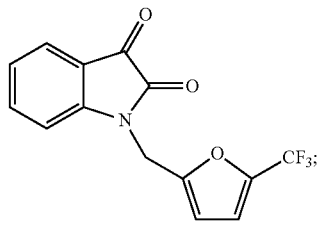
(3a1)

or a pharmaceutically acceptable salt thereof.

21. The method of claim 18 wherein the compound of formula (4) is a compound of formula (4a):

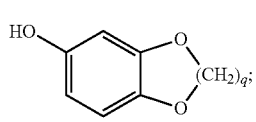
(4a)

where q is 1 or 2.

22. The method of claim 21 wherein the compound of formula (4a) is a compound of formula (4a1):

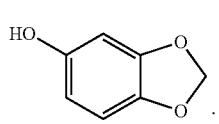
(4a1)

23. The method of claim 18 further comprising a N-alkylation step prior to treating a compound of formula (3) with the intermediate Grignard addition product, wherein the N-alkylation step comprises treating a compound of formula (1):

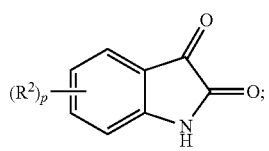
(1)

where p and $R^2$ are each as defined above in claim 1 for the compounds of formula (I), or a pharmaceutically acceptable salt thereof, with a compound of formula (2):

X—$R^1$    (2);

where X is halo and $R^1$ is as defined above in claim 1 for the compounds of formula (I), under suitable N-alkylation conditions to provide a compound of formula (3), as described above.

24. The method of claim 23 wherein the compound of formula (1) is a compound of formula (1a):

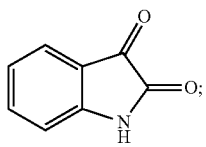

(1a)

or a pharmaceutically acceptable salt thereof.
25. The method of claim 23 wherein the compound of formula (2) is a compound of formula (2a):

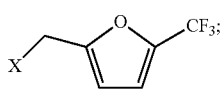

(2a)

where X is halo.
26. A method of preparing a compound of formula (I):

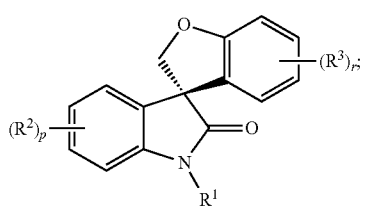

(I)

as an isolated (S)-enantiomer, or a non-racemic mixture of enantiomers having an enantiomeric excess of the (S)-enantiomer of greater than 80%, or a pharmaceutically acceptable salt thereof;
wherein:
p and r are each independently 1, 2, 3 or 4;
$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —$R^8$—C(O)N($R^4$)$R^5$, —S(O)$_2$—$R^5$, —$R^9$—S(O)$_m$—$R^5$ (where m is 0, 1 or 2), —$R^8$—O$R^5$, —$R^8$—CN, —$R^9$—P(O)(O$R^5$)$_2$, or —$R^9$—O—$R^9$—O$R^5$;
or $R^1$ is aralkyl substituted by —C(O)N($R^6$)$R^7$ where:
  $R^6$ is hydrogen, alkyl, aryl or aralkyl; and
  $R^7$ is hydrogen, alkyl, haloalkyl, —$R^9$—CN, —$R^9$—O$R^5$, —$R^9$—N($R^4$)$R^5$, aryl, aralkyl, cycloalkyl, cycloalkylalkyl, heterocyclyl, heterocyclylalkyl, heteroaryl or heteroarylalkyl;
  or $R^6$ and $R^7$, together with the nitrogen to which they are attached, form a N-heterocyclyl or a N-heteroaryl;
  and wherein each aryl, aralkyl, cycloalkyl, cycloalkylalkyl, heterocyclyl, heterocyclylalkyl, heteroaryl and heteroarylalkyl groups for $R^6$ and $R^7$ may be optionally substituted by one or more substituents selected from the group consisting of alkyl, cycloalkyl, aryl, aralkyl, halo, haloalkyl, —$R^8$—CN, —$R^8$—O$R^5$, heterocyclyl and heteroaryl;
or $R^1$ is aralkyl optionally substituted by one or more substituents selected from the group consisting of —$R^8$—O$R^5$, —C(O)O$R^5$, halo, haloalkyl, alkyl, nitro, cyano, aryl, aralkyl, heterocyclyl and heteroaryl;
or $R^1$ is —$R^9$—N($R^{10}$)$R^{11}$, —$R^9$—N($R^{12}$)C(O)$R^{11}$ or —$R^9$—N($R^{10}$)C(O)N($R^{10}$)$R^{11}$ where:
  each $R^{10}$ is hydrogen, alkyl, aryl, aralkyl or heteroaryl;
  each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN; and
  $R^{12}$ is hydrogen, alkyl, aryl, aralkyl or —C(O)$R^5$;
  and wherein each aryl, aralkyl, cycloalkyl, cycloalkylalkyl, heterocyclyl, heterocyclylalkyl, heteroaryl and heteroarylalkyl for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;
or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—O$R^5$, —$R^8$—C(O)O$R^5$, —$R^8$—N($R^4$)$R^5$, —$R^8$—C(O)N($R^4$)$R^5$, —$R^8$—N($R^5$)C(O)$R^4$, —$R^8$—S(O)$_m$$R^4$ (where m is 0, 1 or 2), —$R^8$—CN, or —$R^8$—NO$_2$;
each $R^2$ is independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N═C($R^4$)$R^5$, —S(O)$_m$$R^4$, —OS(O)$_2$CF$_3$, —$R^8$—C(O)$R^4$, —C(S)$R^4$, —C($R^4$)$_2$C(O)O$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(═N$R^5$)N($R^4$)$R^5$, and —N($R^5$)C(═N—CN)N($R^4$)$R^5$, wherein each m is independently 0, 1, or 2 and each n is independently 1 or 2;
  and wherein each of the cycloalkyl, cycloalkylalkyl, aryl, aralkyl, aralkenyl, heterocyclyl, heterocyclylalkyl, heteroaryl and heteroarylalkyl groups for $R^2$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)O$R^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;
or any two adjacent $R^2$'s, together with the adjacent carbon ring atoms to which they are directly attached, may form a fused ring selected from cycloalkyl, aryl, heterocyclyl and heteroaryl, and the other $R^2$'s, if present, are as defined above;
each $R^3$ is independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N═C($R^4$)$R^5$, —S(O)$_m$$R^4$, —OS(O)$_2$CF$_3$, —$R^8$—C(O)$R^4$, —C(S)$R^4$, —C($R^4$)$_2$C(O)O$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C (S)N(R⁴)R⁵, —N(R⁵)S(O)ₙR⁴, —N(R⁵)S(O)ₙN(R⁴)R⁵, —R⁸—S(O)ₙN(R⁴)R⁵, —N(R⁵)C(=NR⁵)N(R⁴)R⁵, and —N(R⁵)C(N=C(R⁴)R⁵)N(R⁴)R⁵, wherein each m is independently 0, 1, or 2 and each n is independently 1 or 2;

or any two adjacent R³'s, together with the adjacent carbon ring atoms to which they are directly attached, may form a fused ring selected from cycloalkyl, heterocyclyl, aryl or heteroaryl, and the other R³'s, if present, are as defined above;

each R⁴ and R⁵ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R⁴ and R⁵ are each attached to the same nitrogen atom, then R⁴ and R⁵, together with the nitrogen atom to which they are attached, may form a N-heterocyclyl or a N-heteroaryl;

each R⁸ is a direct bond or a straight or branched alkylene chain, a straight or branched alkenylene chain or a straight or branched alkynylene chain; and each R⁹ is a straight or branched alkylene chain, a straight or branched alkenylene chain or a straight or branched alkynylene chain;

wherein the method comprises the following steps:

(a) treating a compound of formula (1):

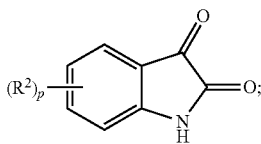

(1)

where p and R² are as described above for the compound of formula (I), or a pharmaceutically acceptable salt thereof, with a compound of formula (2):

X—R¹ (2);

where R¹ is as defined above for the compound of formula (I) and X is halo, under suitable N-alkylation conditions to provide a compound of formula (3):

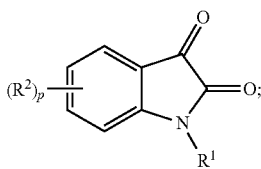

(3)

where p, R¹ and R² are as described above for the compound of formula (I), or a pharmaceutically acceptable salt thereof;

(b) treating the compound of formula (3) under suitable Grignard reaction conditions with an intermediate Grignard addition product formed from the treatment of a compound of formula (4):

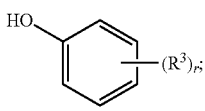

(4)

where r and R³ are as defined above for the compound of formula (I), with a Grignard reagent of formula (5):

RMgX (5);

where R is alkyl and X is iodo, bromo or chloro, under suitable conditions to form a compound of formula (6):

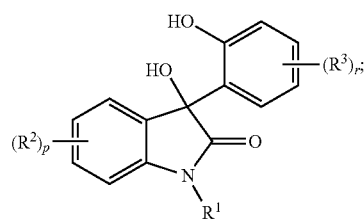

(6)

where p, r, R¹, R² and R³ are as defined above for the compound of formula (I), as a racemic mixture of enantiomers or as a non-racemic mixture of enantiomers, or a pharmaceutically acceptable salt thereof;

(c) treating the compound of formula (6) with a compound of formula (7):

Pg¹X (7);

where X is halo and Pg¹ is an oxygen protecting group under suitable protecting conditions to provide a compound of formula (8):

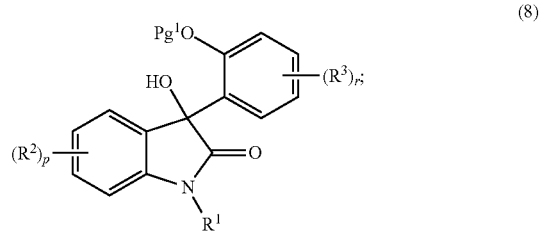

(8)

where p, r, R¹, R² and R³ are as defined above for the compound of formula (I) and Pg¹ is an oxygen protecting group, as a racemic mixture of enantiomers or as a non-racemic mixture of enantiomers, or a pharmaceutically acceptable salt thereof;

(d) treating the compound of formula (8) under suitable dehydroxylation conditions to provide a compound of formula (9):

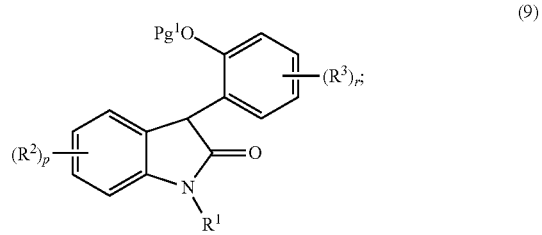

(9)

where p, r, R¹, R² and R³ are as defined above for the compound of formula (I) and Pg¹ is an oxygen protecting group, as a racemic mixture of enantiomers or as a non-racemic mixture of enantiomers, or a pharmaceutically acceptable salt thereof;

(e) treating the compound of formula (9) with a compound of formula (10):

Pg²OCH₂X (10);

where Pg² is an oxygen protecting group and X is halo, under suitable C-alkylation conditions comprising the presence of a phase transfer catalyst selected from a quaternary ammonium salt of quinidine or a quaternary ammonium salt of cinchonine to provide a compound of formula (11):

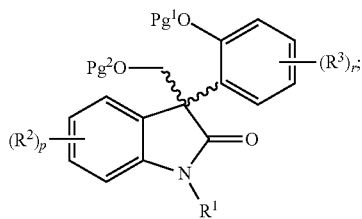

(11)

where p, r, R$^1$, R$^2$ and R$^3$ are each as defined above for the compound of formula (I) and Pg$^1$ and Pg$^2$ are each independently an oxygen protecting group, as a racemic mixture of enantiomers or as a non-racemic mixture of enantiomers, or a pharmaceutically acceptable salt thereof;

(f) treating the compound of formula (11) under suitable recrystallization conditions to provide a compound of formula (12):

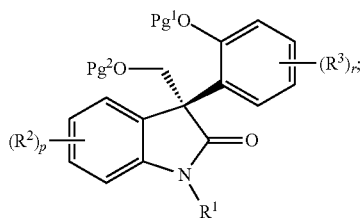

(12)

where p, r, R$^1$, R$^2$ and R$^3$ are as defined above for the compounds of formula (I) and Pg$^1$ and Pg$^2$ are each independently an oxygen protecting group, as an isolated (S)-enantiomer or a non-racemic mixture of enantiomers having an enantiomeric excess of the (S)-enantiomer of greater than 80%, or a pharmaceutically acceptable salt thereof;

(g) treating the compound of formula (12) under suitable deprotecting conditions to provide a compound of formula (13):

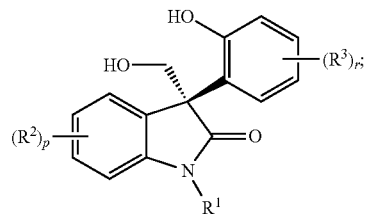

(13)

where p, r, R$^1$, R$^2$ and R$^3$ are as defined above for the compounds of formula (I), as an isolated (S)-enantiomer or a non-racemic mixture of enantiomers having an enantiomeric excess of the (S)-enantiomer of greater than 80%, or a pharmaceutically acceptable salt thereof;

(h) treating the compound of formula (13) under suitable Mitsunobu reaction conditions to provide the compound of formula (I), as defined above, as an isolated (S)-enantiomer or a non-racemic mixture of enantiomers having an enantiomeric excess of the (S)-enantiomer of greater than 80%, or a pharmaceutically acceptable salt thereof.

* * * * *